US006933362B1

(12) United States Patent
Belfort et al.

(10) Patent No.: US 6,933,362 B1
(45) Date of Patent: Aug. 23, 2005

(54) GENETIC SYSTEM AND SELF-CLEAVING INTEINS DERIVED THEREFROM, BIOSEPARATIONS AND PROTEIN PURIFICATION EMPLOYING SAME, AND METHODS FOR DETERMINING CRITICAL, GENERALIZABLE AMINO ACID RESIDUES FOR VARYING INTEIN ACTIVITY

(75) Inventors: Marlene Belfort, Slingerlands, NY (US); Georges Belfort, Slingerlands, NY (US); Vicky Derbyshire, Slingerlands, NY (US); David Wood, Plainsboro, NJ (US); Wei Wu, Albany, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 281 days.

(21) Appl. No.: 09/641,808

(22) Filed: Aug. 17, 2000

Related U.S. Application Data

(60) Provisional application No. 60/149,257, filed on Aug. 17, 1999.

(51) Int. Cl.$^7$ ............................ C07K 1/00; C07K 14/00
(52) U.S. Cl. ....................................... 530/300; 530/350
(58) Field of Search ................................ 530/300, 350

(56) References Cited

U.S. PATENT DOCUMENTS

| 5,496,714 A | 3/1996 | Comb et al. |
| 5,795,731 A | 8/1998 | Belfort |
| 5,834,247 A | 11/1998 | Comb et al. |

OTHER PUBLICATIONS

Shingledecker et al. (2000) "Reactivity of the cysteine residues in the protein splicing active center of the Mycobacterium tuberculosis RecA intein" Arch. Biochem. Biophys. 375:138–144.
Noren et al. (2000) "Dissecting the chemistry of protein splicing and its applications" Angewandte Chemie Int. Ed. 39:450–466.
Smith et al. (1981) "Comparison of Biosequences" Adv. App. Math. 2:482–489.
Shao et al. (1995) "Protein splicing characterization of the aminosuccinimide residue at the carboxyl terminus of the excised intervening sequence" Biochem. 34:10844–50.
Wu et al. (1998) "Protein trans–splicing and functional mini–inteins of a cyanobacterial dnaB intein" Biochim. Biophys. Acta 1387:422–32.
Cooper et al. (1993) "Protein splicing: excision of intervening sequences at the protein level" Bioessays 15:667–674.
Fish et al. (1984) "The interaction between fermentation and protein recovery" BioTech. 2:623–627.
Horton et al. (1990) "Gene splicing by overlap extension: Tailor–made genes using the polymerase chain reaction" BioTech. 8:528–536.

Southworth et al. (1999) "Purification of proteins fused to either the amino or carboxy terminus of the *Mycobacterium xenopi* gyrase A intein" BioTech. 27:110–120.
Linder et al. (1998) "Improved immobilization of fusion proteins via cellulose–binding domains" Biotech. & Bioeng. 60:642–647.
Myers et al. (1988) "Optimal Alignments in Linear Space" CABIOS 4:11–17.
Higgins et al. (1989) "Fast and sensitive multiple sequence alignment of a microcomputer" CABIOS 5:151–153.
Cussler (1984) "Values of Diffusion coefficients" Diffusion: Mass transfer in fluid systems Cambridge University Press pp 105–143.
Davis et al. (1992) "Protein splicing in the maturation of the M. tuberculosis recA protein: A mechanism for tolerating a novel class of intervening sequence" Cell 71:201–210.
Duan et al. (1997) "Crystal structure of PI–SceI, a homing endonuclease with protein splicing activity" Cell 89:555–564.
Gimble. (1998) "Putting protein splicing to work" Chemistry & Biology 5:R251–R256.
Beachy et al. (1997) "Multiple roles of cholesterol in hedgehog proteins biogenesis and signaling" Cold Spring Harbor Symp. Quant. Biology 62:191–204.
LaVallie et al. (1995) "Gene fusion expression systems in *Escherichia coli*" Curr. Opin. Biotech. 6:501–506.
Shao et al. (1996) "Engineering new functions and altering existing functions" Curr. Opin. Struct. Biol. 6:513–518.
Ghim et al. (1998) "An 8 kb nucleotide sequence at the 3' flanking region of the sspC gene (184°) on the *Bacillus subtilis* 168 chromosome containing an intein and an intron" DNA Res. 5:121–6.

(Continued)

*Primary Examiner*—Mark Navarro
(74) *Attorney, Agent, or Firm*—Frommer Lawrence & Haug; Thomas J. Kowalski; William S. Frommer

(57) ABSTRACT

A self-cleaving element for use in bioseparations has been derived from a naturally occurring, 43 kDa protein splicing element (intein) through a combination of protein engineering and random mutagenesis. A mini-intein (18 kDa) previously engineered for reduced size had compromised activity and was therefore subjected to random mutagenesis and genetic selection. In one selection a mini-intein was isolated with restored splicing activity, while in another, a mutant was isolated with enhanced, pH-sensitive C-terminal cleavage activity. The enhanced cleavage mutant has utility in affinity fusion-based protein purification. The enhanced splicing mutant has utility in purification of proteins such as toxic proteins, for example, by inactivation with the intein in a specific region and controllable splicing. These mutants also provide new insights into the structural and functional roles of some conserved residues in protein splicing. Thus, disclosed and claimed are: a genetic system and self-cleaving inteins therefrom; bioseparations employing same; protein purification by inactivation with inteins in specific regions and controllable intein splicing; methods for determining critical, generalizable residues for varying intein activity; and products.

31 Claims, 28 Drawing Sheets

OTHER PUBLICATIONS

Ryan et al. (1994) "Foot–and–mouth disease virus 2A oligopeptide mediated cleavage of an artificial polyprotein" EMBO J. 13:928–933.

Xu et al. (1996) "The mechanism of protein splicing and its modulation by mutation" EMBO J. 15:5146–5153.

Southworth et al. (1998) "Control of protein splicing by intein fragment reassembly" EMBO J. 17:918–26.

Chong et al. (1997) "Single–column purification of free recombinant proteins using a self–cleavage affinity tag derived from a protein splicing element" Gene 192:271–281.

Shingledecker et al. (1998) "Molecular dissection of the Mycobacterium tuberculosis RecA intein: design of a minimal intein and of a trans–splicing system involving two intein fragments" Gene 207:187–195.

Mathys et al. (1999) "Characterization of a self–splicing mini–intein and its conversion into auto–catalytic N– and C–terminal cleavage elements: facile production of protein binding blocks for protein ligation" Gene 231:1–13.

Belfort et al. (1984) "A genetic system for analyzing E. coli thymidylate synthase" J. Bact. 160:371–378.

Davis et al. (1991) "Novel structure of the recA locus of Mycobacterium tuberculosis implies processing of the gene product" J. Bact. 173:5653–5662.

Telenti et al. (1997) "The Mycobacterium xenopi GyrA protein splicing element: characterization of a minimal intein" J. Bact. 179:6378–82.

Hirata et al. (1990) "Molecular structure of a gene, VMA1, encoding the catalytic subunit of H+–translocating adenosine triphosphatase from vacuolar membranes of Saccharomyces cerevisiae" J. Biol. Chem. 265:6726–6733.

Chong et al. (1996) "Protein splicing involving the Saccharomyces cerevisiae VMA intein: the steps in the splicing pathway, side reactions leading to protein cleavage and establishment of an in vitro splicing system" J. Biol. Chem. 271:22159–2168.

Wang et al. (1997) "Identification of an unusual intein in chloroplast ClpP protease of Chlamydomonas eugametos" J. Biol. Chem. 272:11869–73.

Chong et al. (1997) "Protein splicing of the Saccharomyces cerevisiae VMA intein without the endonuclease motifs" J. Biol. Chem. 272:15587–15590.

Chong et al. (1998) "Modulation of protein splicing of the Saccharomyces cerevisiae vacuolar membrane ATPase intein" J. Biol. Chem. 273:10567–10577.

Lew et al. (1998) "Protein splicing in vitro with a semisynthetic two–component minimal intein" J. Biol. Chem. 273:15887–90.

Evans et al. (1999) "The in vitro ligation of bacterially expressed proteins using an intein from Methanobacterium thermoautotrophicum" J. Biol. Chem. 274:3923–3926.

Evans et al. (1999) "The cyclization and polymerization of bacterially expressed proteins using modified self–splicing inteins" J. Biol. Chem. 274:18359–18363.

Pradhan et al. (1999) "Recombinant human DNA (Cystosine–5) methyltransferase I. Expression, purification, and comparison of de novo and maintenance methylation" J. Biol. Chem. 274:33002–33010.

Evans et al. (2000) "Protein trans–splicing and cyclization by a naturally split intein of the dnaE gene of Synechocystis species PCC6803" J. Biol. Chem. 275:9091–9094.

Poland et al. (2000) "Structural insights into the protein splicing mechanism of PI–SceI" J. Biol. Chem. 275:16408–16413.

Chen et al. (2000) "Protein splicing in the absence of an intein penultimate histidine" J. Biol. Chem. 275:20431–20435.

Dalgaard et al. (1997) "Statistical modeling, phylogenetic analysis and structure prediction of a protein splicing domain common to inteins and hedgehog proteins" J. Comput. Biol. 4:193–214.

Ryan et al. (1991) "Cleavage of foot–and–mouth disease virus polyprotein is mediated by residues located within 19 amino acid sequence" J. Gen. Virol. 72:2727–2732.

Needleman et al. (1970) "A general method applicable to the search for similarities in the amino acid sequences of two proteins" J. Mol. Biol. 48:444–453.

Volkin et al. (1996) "The characterization, stabilization, and formulation of acidic fibroblast growth factor" Pharma Biotech. 9:181–217.

Wilbur et al. (1983) "Rapid similarity searches of nucleic acid and protein data banks" Proc. Natl. Acad. Sci. USA. 80:726–30.

Clarke. (1994) "A proposed mechanism for the self–splicing of proteins" Proc. Natl. Acad. Sci. USA 91:11084–8.

Liu et al. (1997) "DnaB intein in Rhodothermus marinus: indication of recent intein homing across remotely related organisms" Proc. Natl. Acad. Sci. USA. 94:7851–6.

Derbyshire et al. (1997b) "Genetic definition of a proteins-plicing domain: functional mini–inteins support structure predictions and a model for intein evolution" Proc. Natl. Acad. Sci. USA 94:11466–11471.

Mills et al. (1998) "Protein splicing in trans by purified N– and C–terminal fragments of the Mycobacterium tuberculosis RecA intein" Proc. Natl. Acad. Sci. USA. 95:3543–8.

Pietrokovski et al. (1994) "Conserved sequence features of inteins (protein introns) and their use in identifying new inteins and related proteins" Prot. Sci. 3:2340–2350.

Evans et al. (1998) "Semisynthesis of cytotoxic proteins using a modified protein splicing element" Prot. Sci. 7:2256–2264.

Daugelat et al. (1999) "The Mycobacterium tuberculosis recA intein can be used in an ORFTRAP to select for open reading frames" Prot. Sci. 8:644–653.

Kapust et al. (1999) "Escherichia coli maltose–binding protein is uncommonly effective at promoting the solubility of polypeptides to which it is fused" Prot. Sci. 8:1668–1674.

Kane et al (1990) "Protein splicing converts the yeast TFP1 gene product to the 69–kD subunit of the vacuolar H+–adenosine triphosphatase" Science 250:651–657.

Cooper et al. (1995) "Protein splicing: self–splicing of genetically mobile elements at the protein level" TIBS 20:351–356.

Jackson (1986) "A detailed kinetic analysis of the in vitro synthesis and processing of encephalomyocarditis virus products" Virol. 149:114–127.

|  | Val67 | Asp422 |  |
|---|---|---|---|
| Sce vma1 | FTCNATHEL | DYYGIT SDD.SDHQ FLLA | SEQ ID NOS: 9, 18 |
| Mle recA | FAA PN LI | SMNRFD EVE.GNHMY.FVD | SEQ ID NOS: 10, 19 |
| Mxe gyrA | VTG AN PL | VQPVYSLRVD TADHAF.IT | SEQ ID NOS: 11, 20 |
| PGB Pol | IT EG SL | DGYVYD SVD.EDENF.LAG | SEQ ID NOS: 12, 21 |
| Ppu.c dnaB | LELTSN KI | FQNVFD AAN.PIPNF.IA | SEQ ID NOS: 13, 22 |
| Mtu recA | VMA PD KV | RARTFD EVE.ELHTL.VAE | SEQ ID NOS: 14, 23 |
| Cel hh1 | LR IS R FM | TG YSPL NN.GR..I.IV | SEQ ID NOS: 15, 24 |
| Dme hp | LTV PAH LV | KGVVAPL RE.GT..I.VV | SEQ ID NOS: 16, 25 |
| Xla vhh | IRL AA LL | TGAYAPL AH.GT..V.MD | SEQ ID NOS: 17, 26 |
|  | Block B | Block F |  |

B

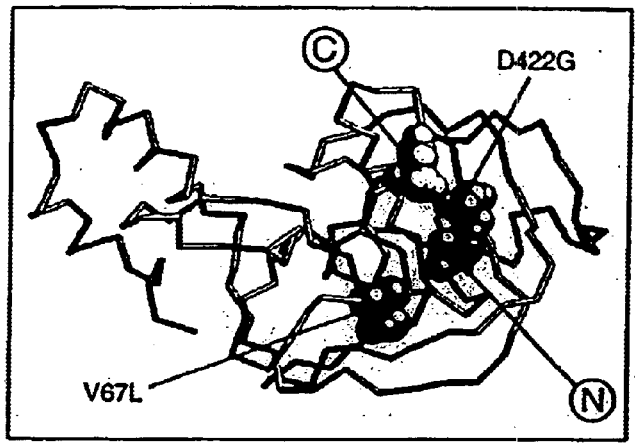

C

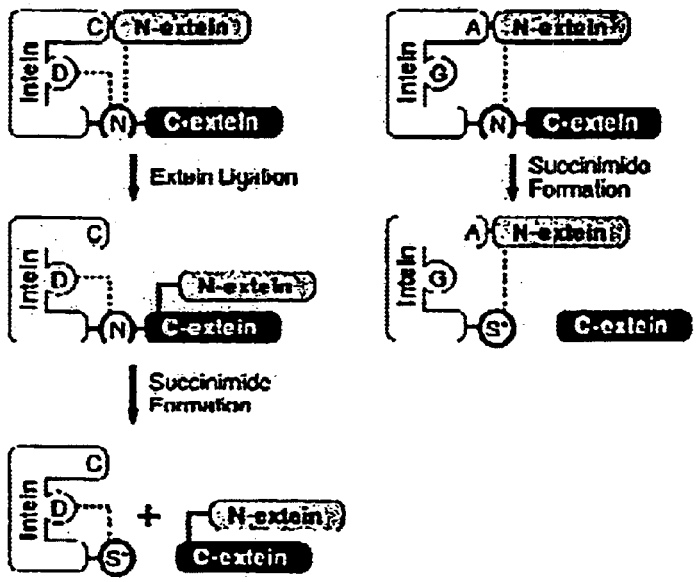

Figure 3
A
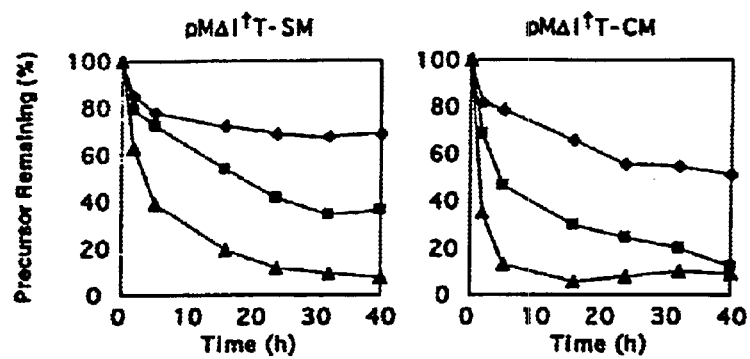
B
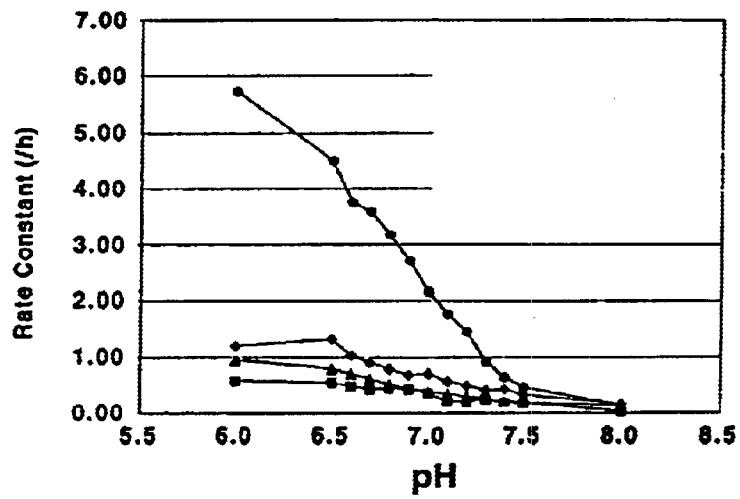
C
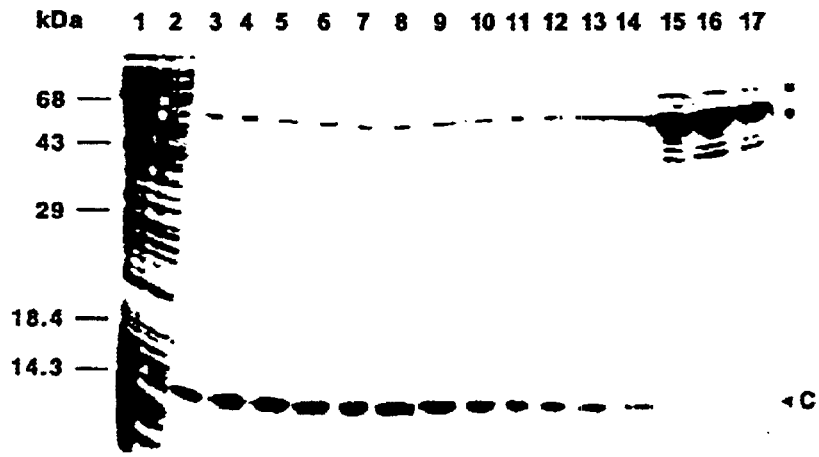

I-TevI [N-terminal catalytic domain — Cys164 — C-terminal DNA binding domain] Joining segment    lethal Insertion of SM::CBD into linker region of I-TevI

B.

I-TevI::SM::CBD    non-toxic

- Prevents Initial Acyl Shift

- Cleavage Mediated by Succinimide Formation

- Miniature Intein Mutant Derived From M.tu. RecA Intein (18 kDa)

A

B Figure 10
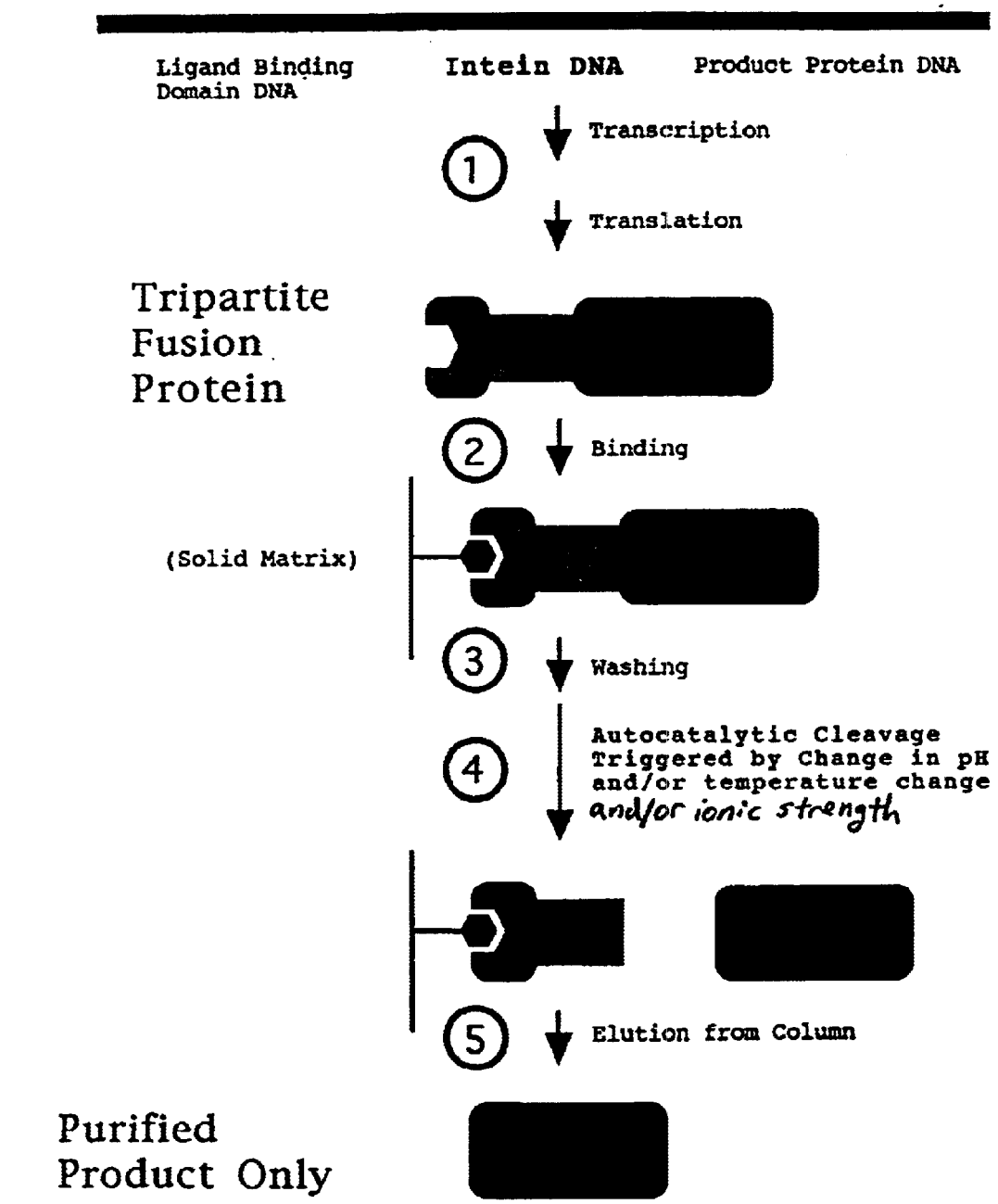

Figure 11
A
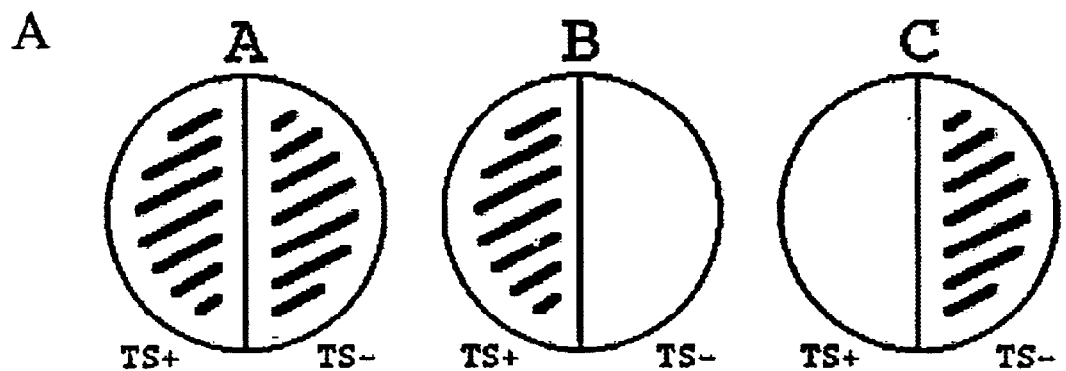
B
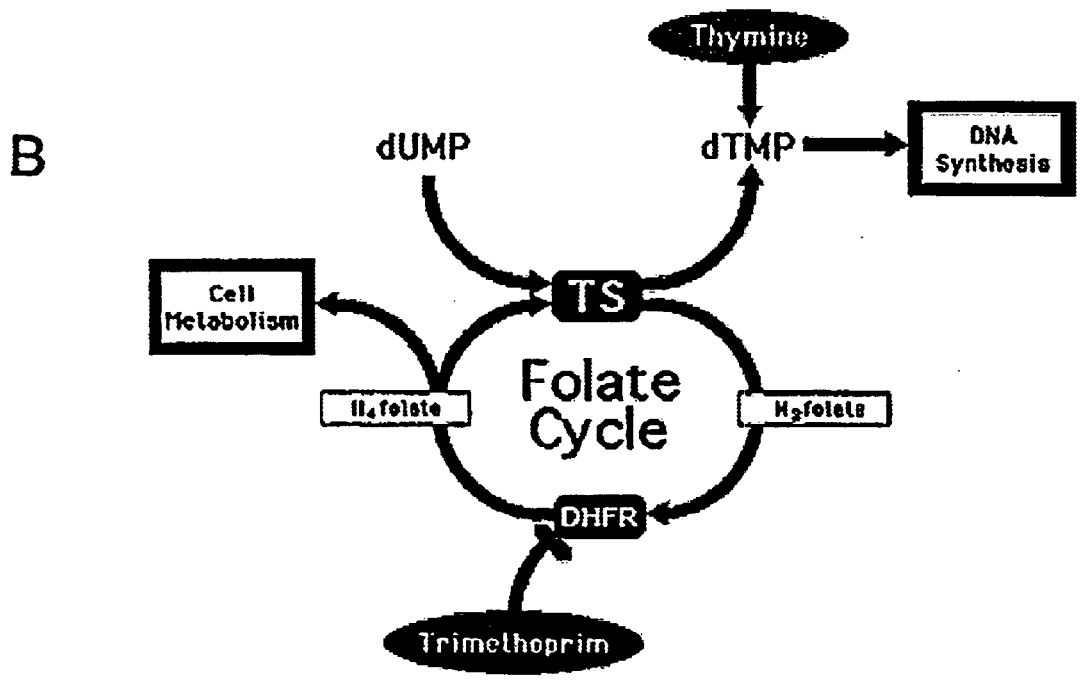

Figure 13
Splicing Activity
(Non Splicing)
Thy−
(Splicing)
Cleaving Activity
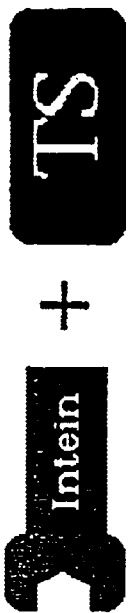
(Non Cleaving)
Thy+
(Cleaving)

Figure 17
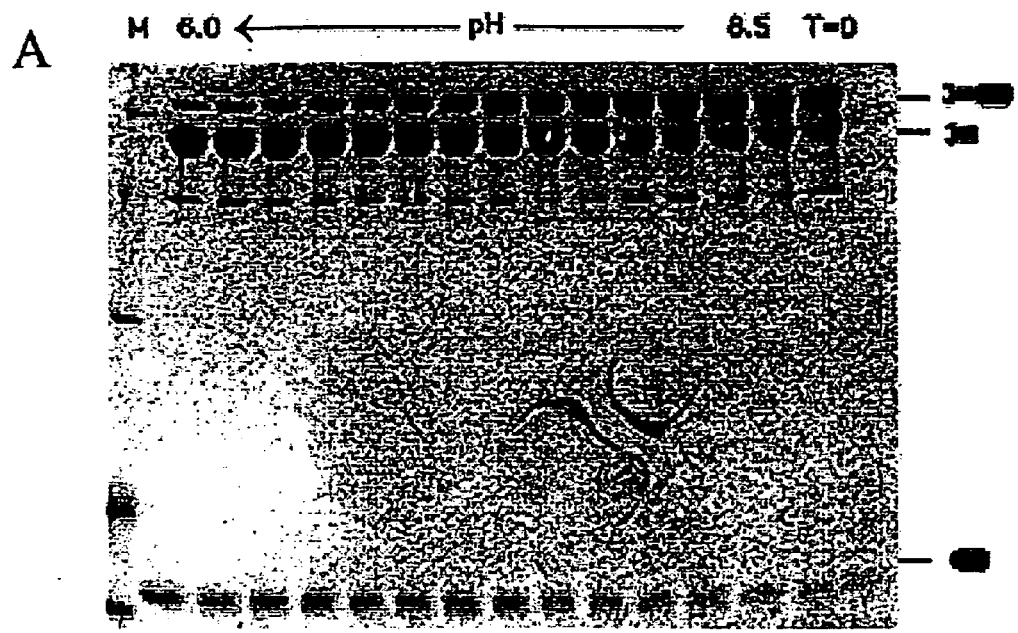
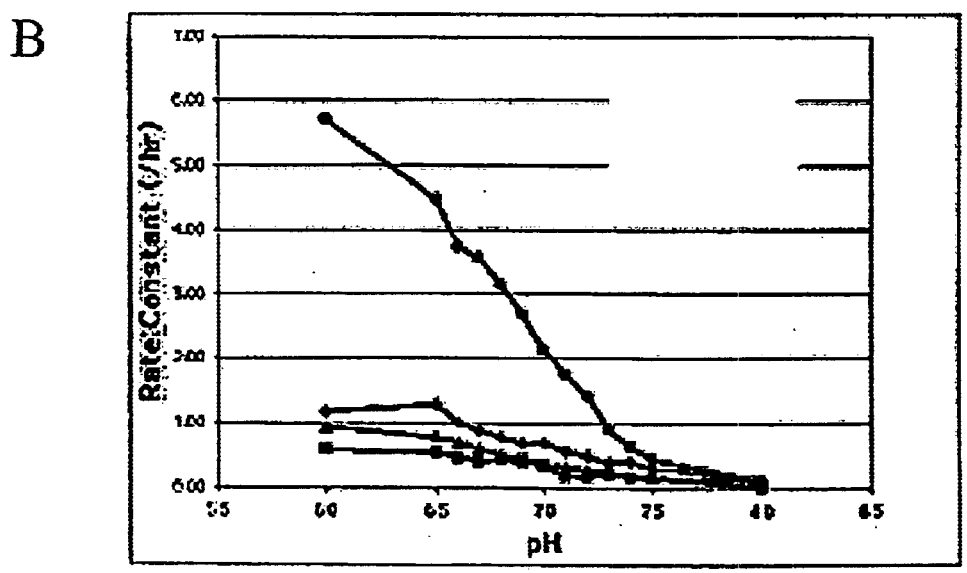

Figure 18
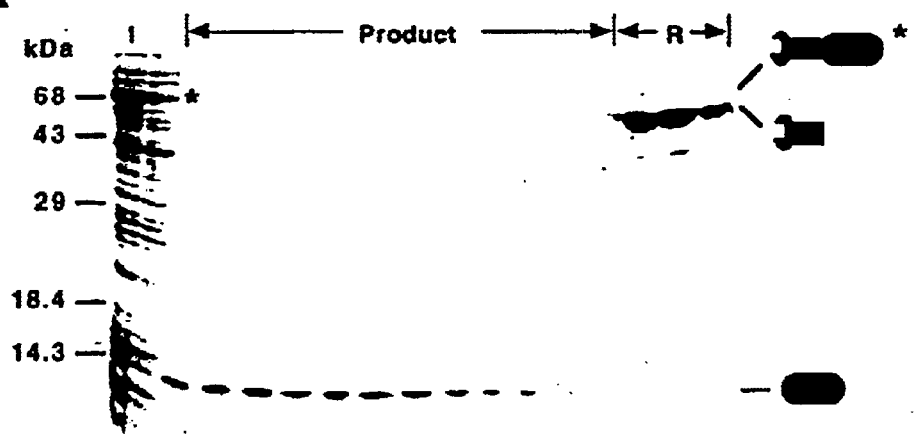
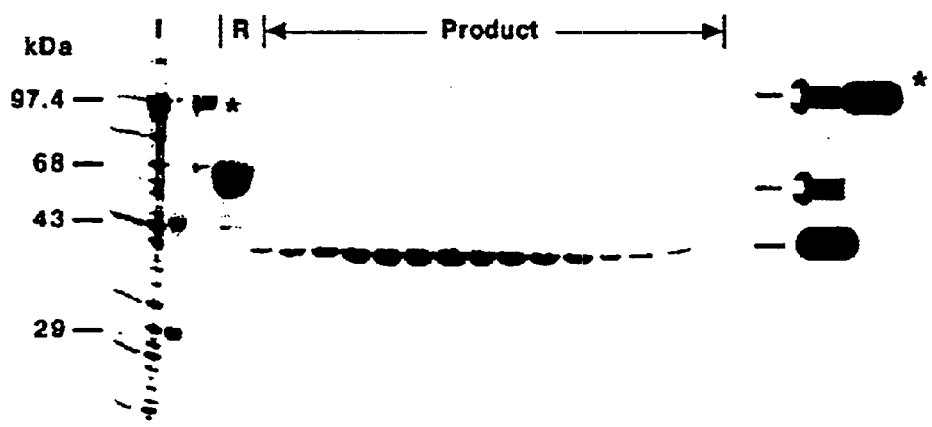
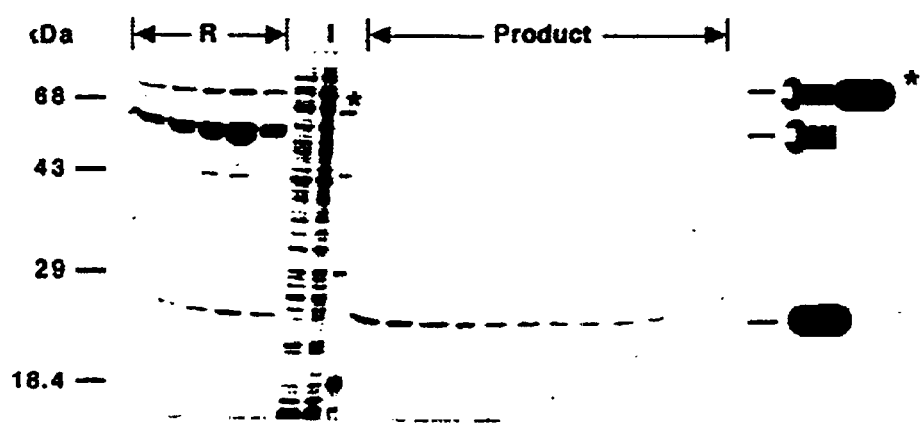

Figure 22
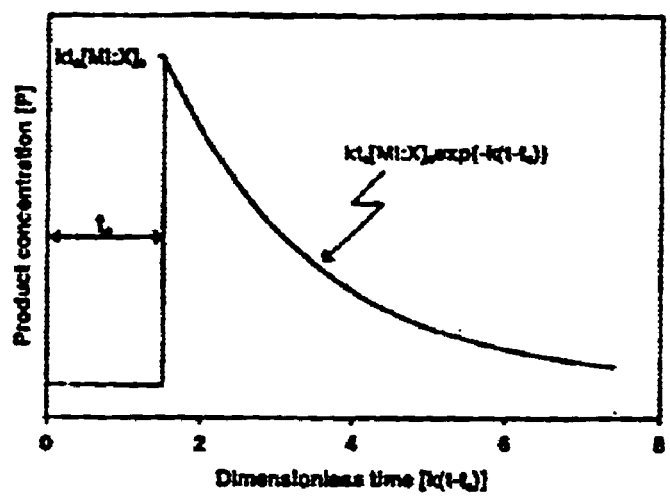
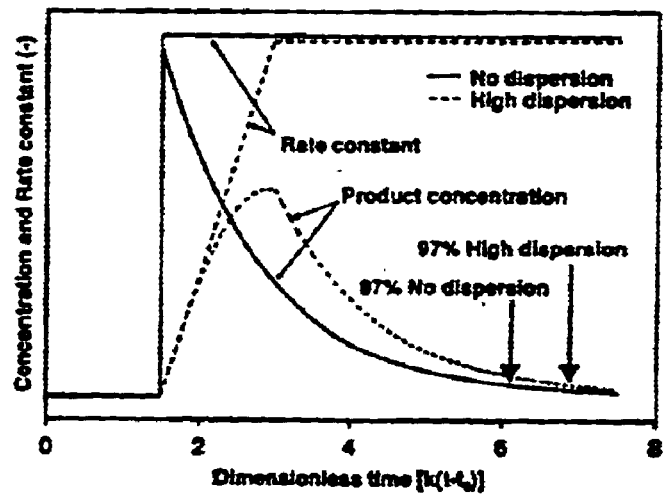

Figure 23
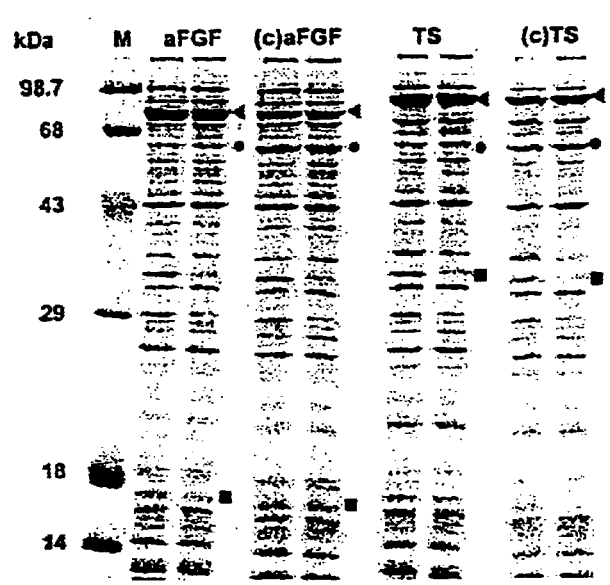
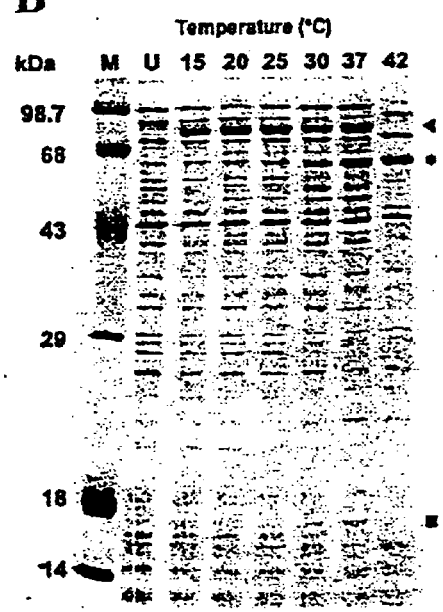

Figure 24
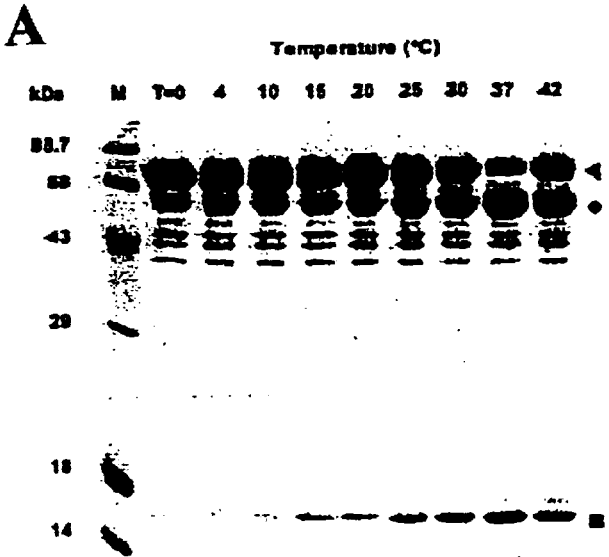
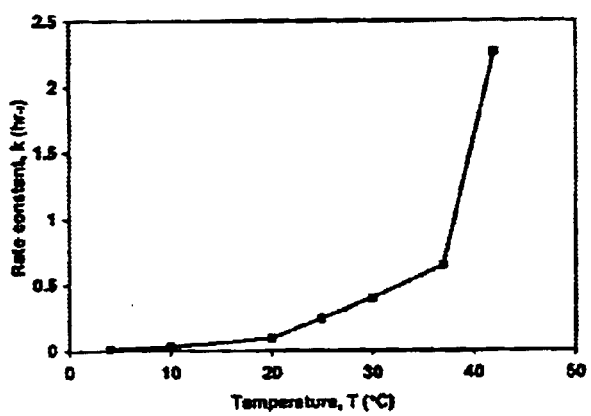
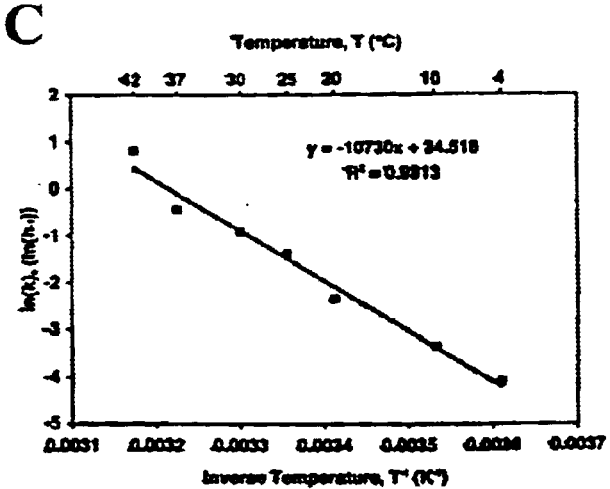

Figure 26
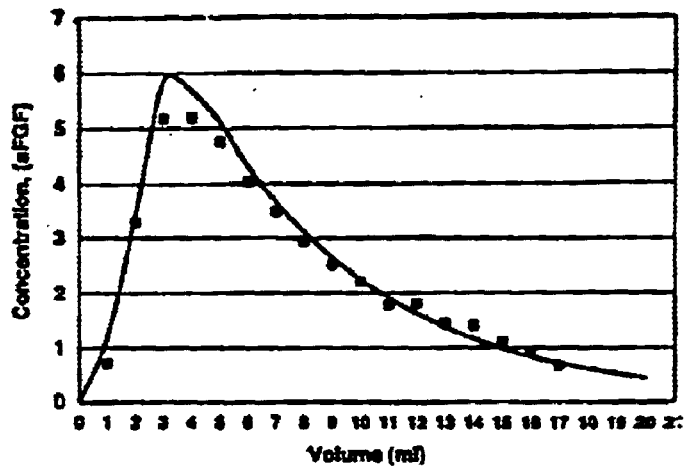
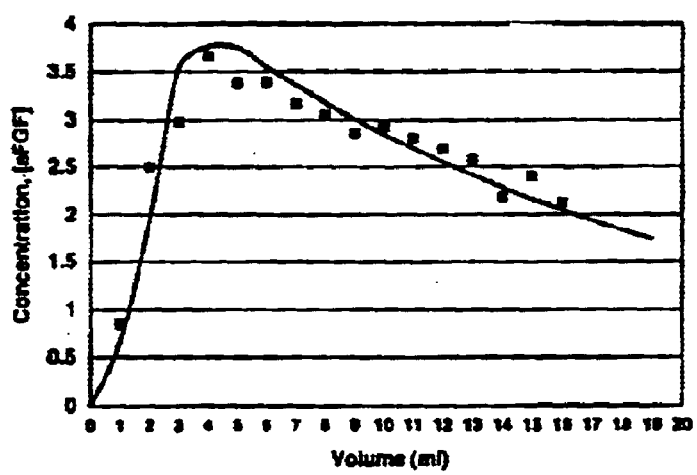

GENETIC SYSTEM AND SELF-CLEAVING INTEINS DERIVED THEREFROM, BIOSEPARATIONS AND PROTEIN PURIFICATION EMPLOYING SAME, AND METHODS FOR DETERMINING CRITICAL, GENERALIZABLE AMINO ACID RESIDUES FOR VARYING INTEIN ACTIVITY

CROSS-REFERENCE TO RELATED APPLICATIONS

This application claims priority from U.S. application Ser. No. 60/149,257, filed Aug. 17, 1999.

SUPPORT

Without any admission, prejudice, intention of creating any estoppel, and the like, especially without any admission as to ownership or rights and without any prejudice to or estoppel against any ownership or rights position, it is stated that this work was supported by NIH grants GM39422 and GM44844, a Howard P. Isermrann fellowship through the Department of Chemical Engineering, Rensselaer Polytechnic Institute and a gift from Baxter Healthcare.

FIELD OF THE INVENTION

The invention relates to one or more of: a genetic system that yields highly active, controllable, self-cleaving inteins; products therefrom; methods for using such products; inteins for bioseparations; purification of proteins, such as toxic proteins (e.g., toxic to host expressing such proteins) by inactivation with inteins, e.g., inteins in specific regions and/or pH-controllable intein splicing; methods for determining critical, generalizable residues for varying intein activity; and products from such methods and processes using such products, inter alia.

INCORPORATION BY REFERENCE

Each of the applications and patents cited in this text, as well as each document or reference cited in each of these applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text; and, each of these documents or references as well as each document or reference cited in each of the herein-cited documents or references (including any manufacturer's specifications, instructions, etc.), is hereby expressly incorporated herein by reference. Various references are cited by their WWW addresses and the contents of these references are also expressly incorporated herein by reference.

There is no admission that any of the various documents cited in this text are prior art as to the invention. Any document having as an author or inventor person or persons named as an inventor herein is a document that is not by another as to the inventive entity herein.

BACKGROUND OF THE INVENTION

In process biotechnology, purification of proteins from complex biological mixtures involves a series of complicated recovery steps, each of which can compromise the purity and yield of the desired product Fish et al. (1984) BioTech. 2:263.

Reducing the number of such unit processes and their complexity would significantly improve product purity and yield while reducing costs. Fusion based affinity separations provide a simple means of isolating target proteins from complex cell extracts by making use of highly specific interactions between fused peptides and small, easily immobilized ligands. LaVallie et al. (1995) Curr. Opin. Biotechnol. 6:501–506; and Linder et al. (1998) Biotech. Bioeng. 60:642–647. Although fusion-based affinity systems have been known for some time and used extensively in the laboratory, their limitations have precluded their wide use in large scale applications.

In the conventional technique, the DNA coding sequence of a target protein is joined to the DNA sequence of one of a number of binding proteins to form a single open reading frame. Expression results in a two-domain fusion protein that can be easily purified via the affinity of the binding domain for its immobilized ligand. The use of optimized affinity resins minimizes the nonspecific binding of contaminant proteins, ensuring that the fusion product is recovered at high purity. Following purification, the target protein is cleaved from the binding domain at the fusion joint, where the recognition of an appropriate protease has been inserted. The product stream of this purification is a relatively simple mixture consisting of the highly purified protein of interest, the cleaved binding domain, and a small amount of protease.

The potential of this technique for use in large scale pharmaceutical production is limited in part by complications arising from the addition of protease to the purified fusion protein solution. The primary limitation is nonspecific cleavage within the product protein by the protease, leading to the destruction of the desired protein. A second disadvantage is cost; as scales increase, more protease is required, dramatically increasing production costs. Finally, the addition of protease necessitates an additional purification step, and can complicate drug approval due to the highly bioactive nature of these enzymes.

A recent advance in this area has been the introduction of self-cleaving protein linkers, achieved by combining binding domains with modified self-splicing protein elements known as inteins. Discovered in 1990, inteins are naturally occurring internal interruptions in a variety of host proteins. Hirata et al. (1990) J. Biol. Chem. 265:6726–6733; Kane et al. (1990) Science 250:651–657; Perler et al. (1994) Nucl. Acids Res. 22:1125–1127; and Noren et al. (2000) Angew. Chem. Int. Ed. 39:450–466.

Following translation of the host protein-intein precursor sequence, the intein excises itself and ligates the flanking host protein segments (exteins) to form the native host protein and released intein. A major advantage of the claimed method is that the cleavage reaction can take place on the column, eliminating the need for any further purification. Additionally the cleavage reaction only affects the target protein, thus, nonspecifically bound contaminant proteins are not affected and are not released into the product stream. This strategy forms the foundation of the commercially available IMPACT-CN system (New England Biolabs, Beverly, Mass.). (FIG. 1A). Perler et al. (1994). Because the structural information required for splicing exists entirely within the inteins they can be used in a variety of applications involving intein insertion into foreign contexts. The ability to construct intein fusions to proteins of interest has broad potential application. Gimble (1998) Chemistry & Biology 5:R251–R256. One of these is affinity fusion-based protein purification, where an intein is used in conjunction with an affinity group to purify a desired protein. Chong et al. (1997b) Gene 192:271–281; and Chong et al. (1998b)

Nucl. Acids Res. 26:5109–5115. Self-cleavage, rather than splicing of the intein releases the desired protein (FIG. 1B), thereby eliminating the need for protease addition and simplifying overall processing. However, this system has drawbacks. First, in the configuration where the product protein is released by N-terminal cleavage, the cleavage reaction requires the addition of thiol containing compounds that modify the C-terminus of the product protein. Native protein is recovered only after subsequent hydrolysis of the cleavage-inducing reagent. Chong et al. (1997a) J. Biol. Chem. 272:15587–15590. Second, where the product protein is released by C-terminal cleavage in the IMPACT-CN system, the reaction is accompanied by unwanted N-terminal cleavage, requiring the N-terminal fragment to be removed in an additional purification step (described in product literature). Third, the large size of the 56-kDa *Saccharomyces cerevisiae* intein in the IMPACT system can diminish solubility and purification efficiency. For this application to be more attractive, the intein must be altered to yield optimized controllable cleavage rather than splicing. Furthermore, the intein should be as small as possible for this strategy to be attractive for scaleup.

Recent studies have determined that large inteins are bipartite elements consisting of a protein splicing domain interrupted by an endonuclease domain. Dalgaard et al. (1997a) Nucl. Acids Res. 25:4626–4638; Duan et al. (1997) Cell 89:555–564; and Derbyshire et al. (1997a) Proc. Natl. Acad. Sci. USA 94:11466–11471. Because endonuclease activity is not required for protein splicing, mini-inteins with accurate but reduced splicing activity can be generated by deletion of this central domain. Derbyshire et al. (1997b); Chong et al (1997a); and Shingledecker et al. (1998) Gene 207:187–195. Mechanistic studies have also determined the roles of highly conserved residues near the intein/extein junctions in the splicing reaction (FIG. 1A). Chong et al. (1996) J. Biol. Chem. 271:22159–22168; Xu et al. (1996) EMBO J. 15:5146–5153; and Stoddard et al. (1998) Nat. Struct. Biol. 5:3–5. These residues include the initial Cys, Ser or Thr of the intein, which initiates splicing with an acyl shift, the conserved Cys, Ser or Thr immediately following the intein, which ligates the exteins through nucleophilic attack, and the conserved C-terminal His and Asn of the intein, which release the intein from the ligated exteins through succinimide formation. Mutation of these residues can be used to alter intein activity to yield isolated cleavage at one or both of the intein-extein junctions. Chong et al. (1998b) J. Biol. Chem. 273:10567–10577.

Despite insights into intein structure and function, modifications often resulted in unacceptably low activity, poor precursor stability, or insolubility. Derbyshire et al. (1997b); Chong et al. (1997b); Shingledecker et al. (1998); and Chong et al. (1998a).

U.S. Pat. No. 5,795,731 (the '731 patent), explicitly stated to be not by "another" as to the present inventive entity, relates to inteins as anti-microbial targets and genetic screens for intein function. Wood et al. AIChE (American Institute of Chemical Engineers) National Meeting, Nov. 17, 1997, Wood et al. ACS (American Chemistry Society) National Meeting, Aug. 22–27, 1998; and Wood et al., AIChE (American Institute of Chemical Engineers) National Meeting, November 1998, are also explicitly stated to be not by "another" as to the present inventive entity. These Abstracts and presentations failed to teach or suggest various methods and products of the invention, including, without limitation, purification by inactivation with intein in specific regions, pH-controllable intein splicing, and methods for determining critical, generalizable residues for varying intein activity. Furthermore, these references failed to provide sufficient details for one skilled in the art to make or use inteins or mutant inteins of the invention. The Wood 1997 Abstract and presentation also failed to teach or suggest pH sensitivity or ion sensitivity by inteins or mutant inteins. Thus, the '731 patent and the Wood Abstracts and presentations fail to teach or suggest the invention.

The N-terminal (acyl shift) and C-terminal (succinimide formation) cleavage activities of the intein are separable. A great deal of work has been done to examine the N-terminal cleavage reaction, primarily because it is very similar to the cleavage reaction exhibited by hedgehog signal proteins. The N-terminal cleavage takes place in two separate steps. In the first step, the peptide bond between the intein and the N-extein is converted to a thioester (or ester in some cases). In the second step, the thioester bond is cleaved by some sort of accessory molecule. In the case of IMPACT, a commercially available affinity system from New England BioLabs, Inc. (NEB) the accessory molecule is a strong nucleophile such as P-mercaptoethanol or dithiothreitol (DTT) both of which are strong reducing agents. The nucleophile cleaves the thioester bond, i.e., a chemical mediated cleavage and not an enzyme mediated cleavage. Thus, although the initial thioester formation is mediated by the intein, the actual cleavage of the product protein is a simple chemical cleavage of a thioester bond by a small nucleophilic molecule. Thus, the N-terminal cleavage reaction can not be accelerated beyond what can be achieved through the simple chemical thioester cleavage reaction (intein structure does not play a role) and enzymatic rates of cleavage can not be attained. That is, despite changes to the intein, cleavage will always be rate-limited by the thioester cleavage reaction. IMPACT cleavage only allows for N-terminal cleavage, thereby eliminating most of the solubility and expression level advantages associated with affinity fusion. A newly available IMPACT-CN system allows N- or C-terminal cleavage, but requires an additional purification step in the case of C-terminal cleavage. Both IMPACT ND IMPACT-CN rely on N-terminal cleavage as part of the protein purification process. Even the C-terminal cleavage reaction of IMPACT-CN is modulated by the thioester mediated N-terminal cleavage reaction as cleavage takes place at both ends of the intein.

More generally, information, documents and products cited herein show that inteins and uses thereof are known. However, prior to the invention, inteins, modifications thereof and uses thereof have suffered from unacceptably low activity, poor precursor stability, and/or insolubility; and, there has been a failure heretofore to teach or suggest addressing these problems by way of any one or any combination of: a genetic system that yields self-cleaving inteins; products therefrom; methods for using such products; inteins for bioseparations; purification of proteins, such as toxic proteins (e.g., toxic to host expressing such proteins) by inactivation with inteins, e.g., inteins in specific regions and/or pH-controllable intein splicing; methods for determining critical, generalizable residues for varying intein activity; and products from such methods and processes using such products, inter alia.

The technique of in vitro protein ligation in which a protein is generated with an N-terminal Cys residue and is then used to cleave the thoiester intermediate of another protein fusion has been shown. Evans et al. (1999a) J. Biol. Chem. 274:3923–3926; Mathys et al. (1999) Gene 231:1–13; and Evans et al. (1999b) J. Biol. Chem. 274:18359–18363. The result is a simple fusion protein in which the two subunits can theoretically be from different expression systems. Although this technique is unique and interesting, it has nothing to do with the purification of native peptides. More importantly, in cases, where C-terminal cleavage is used, several amino acids are added to the beginning of the product protein. The added amino acids are described as "specific" with the sequence (CGEQPTG (SEQUENCE ID NO:1)). Evans et al. (1999a). The first five of these amino acids are the native extein sequence for the intein and appear to be required for efficient cleavage although all this is not explicitly discussed. The studies either included 5 native C-extein residues (SIEQD (SEQ ID NO:2)), or another specific (CRAMG (SEQ ID NO:3) used to allow the addition of a Cys to the beginning of the product protein. Mathys et al. (1999). If the first of the 5 native amino acids following the intein is mutated to Met (MIEQD(SEQ ID NO:4)), then cleavage takes place rapidly in vivo, preventing the efficient purification of uncleaved precursor. Again it is not discussed whether native proteins can be purified using this system, and apparently was not attempted as part of this work. The pTWIN technique of using a two-intein system to make cyclic proteins was described by Evans et al. (1999b). Again, this has nothing to do with the purification of native peptides, and again all of the proteins have the CRAMG (SEQ ID NO:3) specific included to allow efficient C-terminal cleavage. Southworth et al. (1999) Biotech. 27:110–120.

It has been claimed that the intein systems can be used to purify native product proteins through isolated C-terminal cleavage. However, the publication does not support this conclusion and does not provide details of vector construction. In the examples shown, substantial in vivo cleavage has taken place before protein purification. See, Table 2. It is also likely that the proteins being purified here begin with a non-native Ser residue. This is not specified in the paper, but is instead based on a reference to a paper published in 1997, which also does not specify the junction but instead refers to a paper published in 1993, which also does not specify the junction residues. The 1993 paper mentions that a Ser is added to the beginning of the product protein to allow splicing, but it is not clear that it was retained or might have been removed for cleavage experiments.

SUMMARY OF THE INVENTION

The invention provides, without limitation, a genetic system that yields self-cleaving inteins; products therefrom; methods for using such products; inteins for bioseparations; purification of proteins, such as toxic proteins (e.g., toxic to host expressing such proteins) by inactivation with inteins, e.g., inteins in specific regions and/or pH-controllable intein splicing; methods for determining critical, generalizable residues for varying intein activity; products obtained from such methods and processes using such products.

The invention encompasses a non-naturally occurring intein having splicing activity and controllable cleavage activity; or, a non-naturally occurring compound having cleaving and/or cleaving and splicing activity, that is controllable; and, uses thereof. The intein can comprise a truncated intein. The cleavage activity can be controllable by varying at least one physical condition or by varying at least one chemical condition or by varying both at least one physical condition and at least one chemical condition. The cleavage activity can be controllable by varying pH. The cleavage activity is controllable by varying temperature. The cleavage activity can be controllable by varying ion concentration, presence or absence. The cleavage activity can be controllable by varying oxidative potential. The cleavage activity can be controllable by at least two of varying pH, temperature, oxidative potential, and ion concentration, presence or absence. Advantageously, the cleavage activity is controllable by varying pH or by varying temperature and pH.

The intein can also be a mutant intein. The intein can be obtained from random mutagenesis of a truncated intein, followed by selection based on growth phenotype. The intein can have C-terminal cleavage. The intein can be a truncated Mtu intein. The intein can have the endonuclease domain deleted. The intein can be a truncated Mtu intein with the endonuclease domain deleted, and V67L and/or D422G mutation(s) (relative to full-length Mtu intein). The intein can contain the C-terminal histidine-asparagine. (The presence of the C-terminal histidine residue is believed to confer pH sensitivity and thus it is advantageous that the C-terminal histidine be present; the final asparagine is believed useful for cleavage activity.)

The invention further encompasses a protein including an inventive intein. The protein can include a polypeptide of interest and the intein.

The protein can have the intein in an inter-domain region of the polypeptide of interest.

The protein can include a binding protein portion, the intein, and a reporter protein portion. In the protein the intein can separate the binding protein portion and the reporter protein portion. The reporter protein can be an enzymatic assay protein, a protein conferring antibiotic resistance, or a protein providing a direct colorimetric assay. The reporter protein can be selected from the group consisting of thymidylate synthase, β-galactosidase, galactokinase, alkaline phosphatase, β-lactamase, luciferase, and green fluorescent protein.

The protein can include a binding protein portion, the intein, and a protein of interest portion. The intein can separate the binding protein portion and the protein of interest portion.

The protein can be an external fusion of a polypeptide and the intein.

The protein can be an internal fusion of a polypeptide and the intein.

The protein can be a fusion of a desired polypeptide and the intein, as either an internal fusion or an external fusion, wherein the intein is located before a serine, threonine or cysteine residue of the desired polypeptide.

The protein can include a desired polypeptide and the intein, wherein the intein and the desired polypeptide are separated by a serine, threonine or cysteine residue.

The protein can include a desired polypeptide and the intein, wherein the C-terminal histidine or asparagine or histidine-asparagine of the intein is immediately followed by the initial methionine of the desired polypeptide.

The protein can include a desired polypeptide and the intein, wherein the initial methionine of the desired polypeptide has been eliminated. The eliminated methionine can be replaced with cysteine.

The protein can include a desired polypeptide and the intein, wherein the C-terminal histidine or asparagine or histidine-asparagine of the intein is immediately followed by the second amino acid of the desired polypeptide. The second amino acid of the desired polypeptide can be lysine.

The presence of the penultimate C-terminal histidine residue may confer pH sensitivity. Thus, it may be advantageous that the C-terminal histidine be present. Preferably the C-terminal asparagine is present for cleavage activity. More in particular, without necessarily wishing to be bound by any one particular theory, it is believed that the mechanism of intein cleavage requires that the final residue of the intein be asparagine (not histidine). The C-terminal histidine referred to herein can be the highly conserved histidine that immediately precedes the final asparagine. If the C-terminal histidine of the intein is immediately followed by the reporter molecule (or the desired polypeptide or a portion thereof), then if there is no asparagine residue at the final residue, cleavage may not always be possible. The mention herein of a dipeptide at the end of the intein sequence can be interpreted as "Z-asparagine", to show that the final asparagine residue of the intein is advantageously present for any cleavage, while the histidine residue that precedes it is thought to be responsible for the pH sensitivity of the intein, i.e., "Z" can be histidine. However, "Z" can be any suitable amino acid, such as an amino acid that confers pH sensitivity, e.g., pH sensitivity outside of the range of when "Z" is histidine; for instance, to shift the range of pH sensitivity of the intein.

Thus, in embodiments of the invention, one can make mutant or modified inteins or truncated portions thereof wherein "Z" is other than histidine, and then subjecting the product therefrom to screening/selection as herein described (e.g., varying pH) to ascertain pH sensitivity or a pH sensitivity range conferred by "Z." Advantageously, when an intein or truncated portion thereof is in embodiments of the invention, it has the final, C-terminal, asparagine amino acid, e.g., followed by the reporter molecule or the polypeptide of interest or the portion of the polypeptide of interest (e.g., when the intein or portion thereof is within a desired polypeptide such as in a joining segment or folded to domain of a desired polypeptide), with or without the conserved cysteine, methionine or both. But, it is also noted that the invention encompasses molecules or moieties other than inteins as the cleaving and/or cleaving and splicing entity (e.g., the IS), such as, for example, hedgehog proteins or the 2A protein of the *cardiovirus* encephalomyocarditis virus or the 2A region of the foot-and-mouth-disease virus (FMDV) (for instance, a portion of the 2A region including the 19 amino acid sequence spanning the 2A of FMDV (LLNFDLLKLAGDVESNPGP (SEQ ID NO:5)); (see also infra), and, in those instances, it may be possible that the final C-terminal residue be other than asparagine, e.g., if in those other cleaving and/or cleaving and splicing entities the mechanism involves a residue other than asparagine for the cleavage and/or cleavage and splicing.

The skilled artisan, from this disclosure and knowledge in the art can, without undue experimentation, select a suitable amino acid for the C-terminal end of the cleaving and/or cleaving and splicing moiety for there to be the desired cleavage and/or cleavage and splicing. For instance, if the moiety is an intein or truncated portion thereof, advantageously the C-terminal amino acid is asparagine to obtain cleavage, and if the moiety is other than an intein or truncated portion of an intein, the C-terminal amino acid is advantageously an amino acid that facilitates cleavage and/or cleavage and splicing, e.g., based on the cleavage and/or cleavage and splicing mechanism of the moiety.

The invention yet further encompasses an isolated nucleic acid molecule encoding the inventive intein or the inventive protein. The invention still further encompasses a vector containing the isolated nucleic acid molecule of claim. The invention also encompasses a host cell transformed with the vector. The vector can be a plasmid. The cell can be *E. coli*.

The invention additionally encompasses a method for producing a protein comprising subjecting an inventive protein to cleavage conditions. The invention likewise encompasses a method for producing a protein comprising preparing an inventive protein and subjecting the protein to cleavage conditions. Similarly, the invention encompasses a method for producing a protein comprising preparing a fusion of a polypeptide and an inventive intein and subjecting the fusion to cleavage conditions. The protein or fusion can be prepared recombinantly (or by other known means to prepare a protein or fusion protein, e.g., chemical synthesis).

The protein or fusion can be prepared by preparing a vector containing nucleic acid sequences and/or DNA encoding the protein or the fusion, transforming a host cell with the vector, and expressing the nucleic acid sequences and/or DNA in the host cell.

The invention also encompasses a method for purifying a desired protein comprising preparing a fusion polypeptide comprising a binding protein portion, an inventive intein portion, and a desired protein portion, binding the fusion to a binding moiety, subjecting the intein to cleavage conditions, and separating the desired protein. The binding of the fusion to the binding moiety can be by binding the fusion to an affinity matrix (e.g., beads, membrane, column or material in a column), and the separating can include subjecting the matrix (e.g., column contents) to a chemical and/or physical change such as a pH and/or temperature shift and eluting the desired protein.

The invention further encompasses a one-step protein purification method. The protein is synthesized as a protein/intein hybrid and the intein contains a moiety recognized by and retained on a column. Cells are lysed or cell supermatant is collected after a suitable amount of protein production and the lysate or supernatant is applied to the column and washed. The intein is then induced to cleave itself from the protein and the protein is released from the column to be collected as an eluate.

Even further still, the invention encompasses a method for preparing an inventive intein comprising subjecting intein DNA to random mutagenesis, expressing the intein DNA with a reporter and screening for elevated intein cleavage activity using growth medium and varying conditions. The random mutagenesis can include amplifying intein DNA using a polymerase, such a Taq. The intein DNA can code for a truncated intein.

The invention yet further encompasses a method for screening for enhanced intein cleavage activity including subjecting intein DNA to random mutagenesis, expressing the intein DNA with a reporter and screening for elevated intein cleavage activity using growth medium and varying conditions. The random mutagenesis can include amplifying intein DNA using a polymerase, such as Taq. The intein DNA can encode a truncated intein.

In another aspect, the invention encompasses a method for screening for reduced intein cleavage activity comprising subjecting intein DNA to random mutagenesis, expressing the intein DNA with a reporter and screening for reduced intein cleavage activity using an assay with a chemical that plays a part in a cell metabolic and/or biochemical cycle. The random mutagenesis can comprise amplifying intein DNA using a polymerase, such as Taq. The intein DNA can code for a truncated intein. The chemical can be trimethoprim, the assay can be a trimethoprim gradient, and the cycle can be the folic acid cycle.

In yet a further aspect, the invention encompasses a method for determining amino acid residues in an intein that play a role in cleavage activity comprising deleting and/or changing amino acid(s) (such as for instance any amino acid(s) throughout the intein and/or conserved amino acid(s)

or amino acid(s) that precede conserved amino acid(s) such as amino acid(s) that immediately precede conserved amino acid(s)) in the intein to obtain an altered intein (e.g., an altered intein without splicing activity), preparing a fusion of the altered intein and a reporter and screening or selecting for altered (e.g., reduced or enhanced) intein cleavage activity using an assay e.g., an assay which indicates active reporter, such as an assay which indicates an active reporter including a chemical that plays a part in a cell metabolic and/or biochemical cycle and/or screening or selecting for elevated intein cleavage activity using growth medium (e.g., selective growth medium) and varying conditions. The fusion can be prepared by expressing the altered intein with the reporter. The deleting and/or changing amino acid(s) in the intein can be by random mutagenesis. And, in inventive methods and products, the reporter can be thymidylate synthase.

The term "comprising" in this disclosure can mean "including" or can have the meaning commonly given to the term "comprising" in U.S. Patent Law. Other aspects of the invention are described in or are obvious from (and within the ambit of the invention) the following disclosure.

BRIEF DESCRIPTION OF THE FIGURES

FIG. 1 is discussed in Example 1 and the Specification.

FIG. 2 shows structure/function analysis of mutations. (A) Sequence alignment of the Mtu intein (middle), other inteins (top) and hedgehog proteins (bottom). Mutation locations of the ΔI-SM and ΔI-CM mutants are indicated relative to conserved intein sequence blocks. Highly conserved residues are white on black, while hydrophobic residues are boxed. Peptide sequences are shown in SEQ ID Nos. 9–26, by column, respectively. (B) Mutation locations relative to the Mxe gyrA intein structure. Mutated residues based on alignments in panel (A) are indicated on the Mxe gyrA intein backbone. N and C indicate the N— and C-terminal intein residues. (C) Model for ΔI-CM mini-intein cleavage. In the wild type, H-bonds or electrostatic interactions (. . .) inhibit the C-terminal Asn 441 (N) from succinimide formation until after extein ligation (left). By removing such a bond (drawn here to the terminal Asn but in principle could be to any residue critical for cleavage), the D422G mutant facilitates succinimide formation and C-terminal cleavage (right). In C, C is Cys 1, A is Ala 1 mutant, D is Asp 422, G is Gly 422 mutant, N is Asn 441 and S* is succinimide ring. FIG. 2 is discussed in the Specification.

FIG. 3 shows temperature and pH effects on intein cleavage. (A) Effect of temperature on cleavage rates of ΔI-SM and ΔI-CM in the pMΔI$^\dagger$T context. In A, ♦ is 20° C., ■ is 30° C. and σ is 37° C. (B) Effect of pH on cleavage activity in the MI$^\dagger$C context. Plotted rate constant is that for a fitted first order decay of precursor to products. In B, ♦ is I, ■ is ΔI and σ is ΔI-SM and ● is ΔI-CM. (C) Purification of C-I-TevI using inducible on-column cleavage of the pMΔI$^\dagger$C-CM precursor. Lanes: (1) cleared lysate; (2) flowthrough; (3–14) cleaved C-terminal domain; (15–17) bound, cleaved fusion protein released during column regeneration. In C, ■ is MΔI$^+$C-CM and ● is MΔI$^+$ and Y is C-CM. FIG. 3 is discussed in Example 1.

FIG. 4 shows inactivation of I-TevI by inserting an affinity-tagged mini-intein preceding Cys164. FIG. 4 is discussed in the Specification.

FIG. 5 is discussed in the Specification.

FIG. 6 is discussed in Example 2.

FIG. 7 is discussed in the Specification.

FIG. 8 is discussed in the Specification.

FIG. 9 is discussed in the Specification.

FIGS. 10A and 10B show the FIG. 8 protocol, more generally.

FIGS. 11A, 11B and 11C show (A) and (C) the thymidylate synthase reporter system, and (B) the folate cycle.

FIG. 12 is discussed in the Specification.

FIG. 13 shows the intein screening premise based on thymidylate synthase reporter. FIG. 13 is discussed in the Specification.

FIG. 14 is discussed in the Specification.

FIG. 15 is discussed in the Specification.

FIG. 16 is discussed in the Specification.

FIG. 17 shows pH effect on cleavage activity (A) product conversion vs. pH, during a 15 minute incubation, pH 8.5 to 6.0 and (B) cleavage rate constant vs. pH. FIG. 17B shows: Cleavage rate constant vs. pH, similar to the presentation in FIG. 3B. FIG. 17 is discussed in the Specification.

FIG. 18 shows a reproduction of SDS PAGE gels to demonstrate purification of proteins from tripartite precursors. FIG. 18 is discussed in the Specification.

FIG. 19 is discussed in Example 2.

FIG. 20 is discussed in Example 2.

FIG. 21 is discussed in Example 4.

FIG. 22 shows model predictions of product protein peak shape arising from flow mode operation of intein cleavage. In each case, low pH buffer is introduced into the top of the column at zero time. (A) Predicted peak shape for an ideal (flat) pH front in the absence of dispersion. $[MI:X]_0$=bound precursor column capacity; t=time; k=cleavage reaction rate constant; $t_0$=column residence time. (B) Predicted effects of pH front dispersion on peak shape during elution. Higher dispersion in the pH front leads to an increasingly gradual acceleration of the cleavage reaction as the pH front moves through the column. Product concentration curves are marked where 97% recovery of product protein is achieved for cases of no dispersion and high dispersion. FIG. 22 is discussed in Example 6.

FIG. 23 shows expression of soluble precursor proteins. Post-induction cell lysates were analyzed by SDS-PAGE to determine precursor expression level, solubility and premature cleavage during induction. (A) Fusion precursors with the product proteins indicated at the top of each lane. In all cases, expression was induced at 20° C. for four hours. Lanes: M=molecular weight markers; aFGF=acidic human fibroblast growth factor; TS-thymidylate synthase; (c) denotes the inclusion of a cysteine residue at the beginning of the product protein; ▲=precursor protein; =cleaved binding domain; ■=expected position of cleaved product protein. (B) Effect of induction temperature on precursor expression with cysteineless aFGF as the product protein. Precursor expression was induced at the temperatures indicated at the top of each lane for four hours. Products are labeled as in (A). FIG. 23 is discussed in Example 7.

FIG. 24 shows determination of cleavage kinetics of native MI:aFGF precursor protein. (A) SDS-PAGE gel of cleavage products after 1 hour incubation at pH 6.0 and temperatures indicated at the top of each lane. M=molecular weight markers; T=0=precursor sample at time zero; (B) MI:aFGF cleavage rate constant as a function of temperature at pH 6.0; (C) Plot of ln(k) vs. inverse temperature for determination of activation energy for MI:aFGF cleavage at pH 6.0. FIG. 24 is discussed in Example 7.

FIG. 25 is discussed in Example 7.

FIG. 26 shows comparison of purification data and model predictions. (A) Flow mode purification at 37° C. (B) Flow mode purification at 25° C. Smoothed line in both cases is the model prediction, while symbols represent the actual concentration (measured by scanning densitometry) of the fractions exiting the column. FIG. 26 is discussed in Example 7.

DETAILED DESCRIPTION OF THE INVENTION

Figure 1:
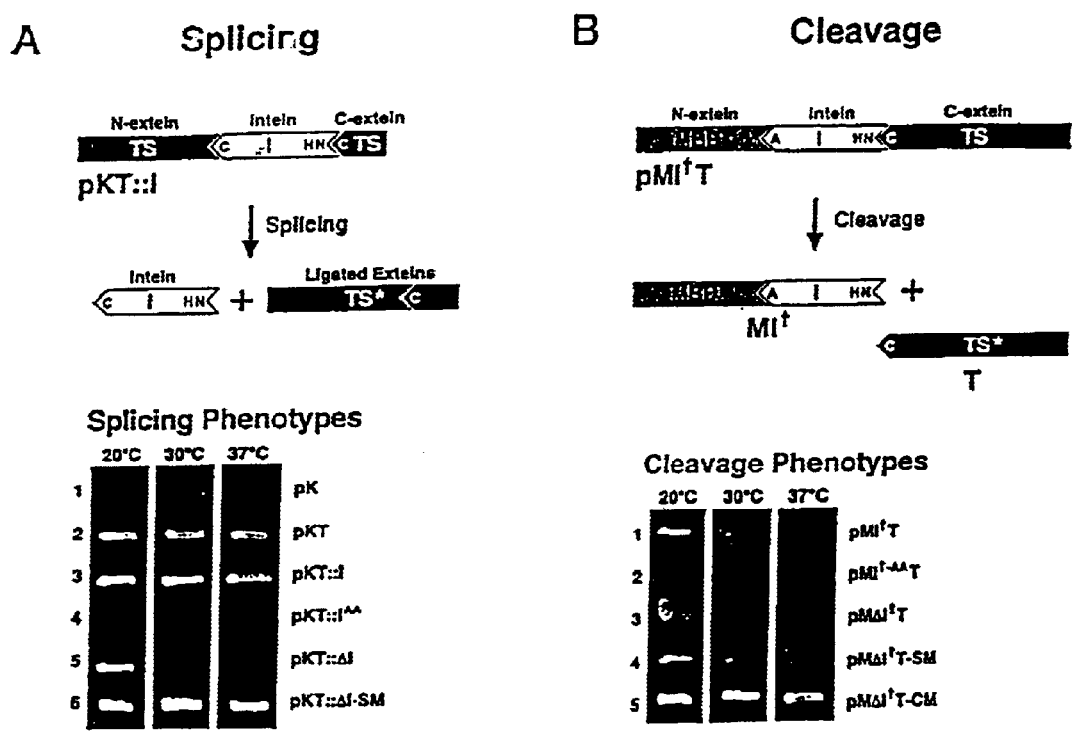
FIG. 1 shows intein-thymidylate synthase (TS) fusions and fusion phenotypes. (A) Splicing. Internal fusion to TS (pKT::I) produces active TS (TS*) upon splicing. (B) Cleavage. External fusion to TS (pMI$^\dagger$T) with the C1A mutation ($^\dagger$) produces TS* upon cleavage. M=maltose binding domain; I=intein; T=TS.

The invention combines protein engineering with random mutagenesis and, by linking intein activity to a selectable growth phenotype, isolate small mutant inteins with desirable splicing or cleaving properties suitable for application in affinity separations. This approach has simultaneously yielded insight into roles of specific residues in intein function and yielded inteins that would not have been available by any other approach. The genetic selection process described herein has provided inteins with rapid C-terminal cleavage (heretofore unavailable) that could not have been found by to rational directed mutagenesis of specific intein residues.

The system provides a way to accelerate the C-terminal cleavage reaction without N-terminal cleavage. In this case, the cleavage reaction is a true enzymatic reaction, where the structure of the mutant intein is responsible for the reaction. Not only have individual superior inteins been identified, but also key cleavage residues and method to generate inteins that are not subject to the limitations of commercially available intein cleavage systems.

As shown in Example 1, through the development of a genetic screen, mutant mini-inteins were isolated with restored splicing activity and enhanced, controllable cleavage activity. Because incubation temperature strongly affects the phenotype of the growing cells, selection for rapid in vivo cleavage was possible. Mutant mini-inteins isolated using this screen have elevated activities in vivo and in vitro, and form the basis of a pH— and temperature-dependent protein purification system. Methods of random mutagenesis are known in the art. Shao et al. (1996) Curr. Opin. Struct. Biol. 6:513–518; and Belfort et al. (1984) J. Bacteriol. 160:371–378.

An important requirement for the application of inteins to protein purification is the acceleration of intein cleavage reactions. Previous work has shown that non-native cleavage can be induced at either end of the intein, but typically the cleavage rate is slow. Chong et al. (1997a); Chong et al. (1998a); Chong et al. (1996); Xu et al. (1996) and Chong et al. (1998b). In these systems, where inteins have been modified for C-terminal cleavage, the reactions can take several days at 4° C., require the addition of a thiol reagent, and are accompanied by N-terminal cleavage, necessitating an additional purification step. Chong et al. (1998a). Furthermore, these inteins are about three times the size of ΔI-CM. By selecting mini-inteins that display rapid, isolated C-terminal cleavage, the inventive system generated a pH-sensitive mutant intein, which obviates the need for reducing reagents and additional purification steps, and has advantageous size and stability characteristics. Most importantly, C-terminal cleavage-based affinity separation times can decrease to several hours at 4° C., or to minutes at higher temperatures, making this technique more attractive for scaleup of intein-based protein purifications.

The specific pH behavior of the inteins is further advantageous in exhibiting a 20- to 40-fold increase in activity between pH 8.5 and 6.0. These pH values are relatively mild, decreasing the potential for damage to the product protein due to pH-induced denaturation, and thus allowing the recovery of pure protein with minimal damage. This small pH change also decreases the possibility that the binding domain will lose affinity during cleavage.

Sequence alignment of 41 inteins and 23 closely related hedgehog proteins indicates that the residue corresponding to Val-67 in the Mtu intein is always hydrophobic (FIG. 2A). Dalgaard et al. (1997a). Crystallographic data from the *Mycobacterium xenopi* (Mxe) gyrA intein (Klabunde et al. (1998) Nature Struct. Biol. 5:31–36) indicate that this residue lies within a hydrophobic core(FIG. 2B). When the endonuclease domain of the Mtu intein was deleted to create ΔI, this hydrophobic core was likely disturbed, leading to loss of stability and activity. Derbyshire et al. (1997a). The V67L mutation appears to restore stability in ΔI-SM and ΔI-CM, in effect acting as an intragenic suppressor of the deletion mutation. This is supported by the fact that the intein is unstable in ΔI constructs, and is stabilized in both the ΔI-SM and ΔI-CM mutants in vivo.

Revertant analysis of individual mutations revealed that while V67L restores intein stability, D24G is of no phenotypic consequence. A double revertant containing the D422G mutation alone indicated that this substitution is responsible for the elevated cleavage activity of the ΔI-CM intein. Phylogenetic data indicate that this residue is 75% conserved as an Asp in inteins, and is always polar (FIG. 2A). Pietrokovski et al. (1994) Prot. Sci. 3:2340–2350; and Dalgaard et al. (1997b) J. Comput. Biol. 4:193–214. In closely related hedgehog proteins, which do not exhibit C-terminal cleavage, this residue is usually a Pro, (Dalgaard et al. (1997a)) suggesting that the Asp plays a role in C-terminal cleavage. Crystallographic data further indicate that this residue is located very near the intein/extein junctions in the tertiary structure of other inteins (FIG. 2B). Duan et al. (1997); and Klabunde et al. (1998). Furthermore, analysis of the Mxe gyrA intein suggests that the backbone carbonyl of the critical C-terminal Asn of the intein is initially hydrogen-bonded to this residue. Klabunde et al. (1998). The location of this conserved Asp and the effect of its elimination suggest a model wherein this residue helps ensure orderly splicing by preventing premature succinimide formation, thereby minimizing isolated cleavage side reactions (FIG. 2C).

The inventors propose that the C-terminal splice junction of the wild-type intein is held initially in a conformation that inhibits succinimide formation by both the last residue of the N-extein and Asp422. Klabunde et al. (1998). Extein ligation releases the N-extein hydrogen bond, freeing the Asn backbone to allow cleavage only after ligation (FIG. 2C, left). The Asp to Gly mutation in the ΔI-CM mutant allows rapid C-terminal cleavage in the absence of ligation by eliminating the Asp422 interaction, thus imparting to the Asn the flexibility required for succinimide formation and C-terminal cleavage (FIG. 2C, right).

A key feature of the ΔI-CM mutant is its extreme pH sensitivity, which allows purification of intact precursor followed by rapid C-terminal cleavage. Although the conserved His immediately preceding the final Asn of native inteins may be responsible for this effect (Chong et al. (1998a); Duan et al. (1997); and Klabunde et al. (1998)), it is now possible to use pH-related cleavage sensitivity to accelerate cleavage to a useful rate. In slow inteins, the overall cleavage rate is not sufficient to allow effective use of this native sensitivity. In the D422G mutant, where the normal controls of the splicing reaction have been disabled, the pH effect becomes dominant in controlling cleavage.

With available structural data on related inteins, (Duan et al. (1997); and Klabunde et al. (1998)) prior to the invention, the specific steps of the splicing reaction were only partially clarified so that prior to the invention it was difficult to predict the effect of any of these mutations on an engineered intein, and virtually impossible to choose residues and mutations for generating these properties. For this reason, the invention, e.g., as illustrated in Example 1, employs a combination of rational protein design and random selection to acquire the desired characteristics for a proposed intein application. The invention thus provides a powerful genetic selection that allows isolation of inteins with desirable properties and also yields mechanistic insights into intein function.

With respect to protein purification, certain proteins cannot be cloned in *E. coli* or other living expression systems, presumably because their expression is lethal to the host cells. Inteins, auto-catalytic protein-splicing elements, provide a novel avenue to the expression and purification of these cytotoxic proteins. This can involve the inactivation of a cytotoxic protein by inserting a modified intein to produce a large amount of innocuous fusion protein, followed by controllable splicing to restore the native conformation of the toxic protein.

If the protein structure is known, the intein is advantageously inserted into specific regions or domains; and, if the protein structure is not yet known, specific regions can be identified through techniques known in the art (e.g., structural, and/or crystallographic, and/or charge, and/or spectroscopic (e.g., NMR) and/or hydrophobicity, and the like analyses for determination of folded domains). Appropriate insertion sites can be determined empirically by testing several different sites and screening for controllable intein activity. Advantageously, the inteins are inserted N-terminal to one or more cysteine residues. More advantageously, the inteins are inserted N-terminal to a zinc finger region. Further still, an aspect of the invention is inserting the intein into a desired polypeptide in a region such that folding, and/or solubility, of the desired polypeptide is not unduly disturbed. A means to achieve this can be by inserting the intein into a specific region. In the case of toxic proteins, the intein can be inserted into a portion of the desired polypeptide where steric or other factors lead to reduction of toxicity (activity); for instance, as exemplified herein.

Most inteins consist of two functionally and structurally distinct domains, a protein-splicing domain and an endonuclease domain. Mini-inteins from the *Mycobacterium tuberculosis* (Mtu) RecA intein with the entire endonuclease domain removed, retain compromised but significant splicing activity. Derbyshire et al. (1997b). Starting from a Mtu RecA mini-intein parent, the thymidylate synthase screen has yielded a splicing mutant (SM) with a Val67 to Leu mutation, which has restored wild-type level splicing activity. Example 1; and Wood et al. (1999a) Nature Biotech. 17:889–892.

I-TevI, the T4 td intron-encoded endonuclease, is lethal to *E. coli*. Expression of wild-type I-TevI has remained impossible till the advent of this novel intein-mediated approach of the invention. I-TevI consists of a N-terminal catalytic domain and a C-terminal DNA-binding domain separated by a flexible unstructured joining segment (FIG. 4A). Derbyshire et al., (1997a) J. Mol. Biol. 265:494–506.

Figure 19:
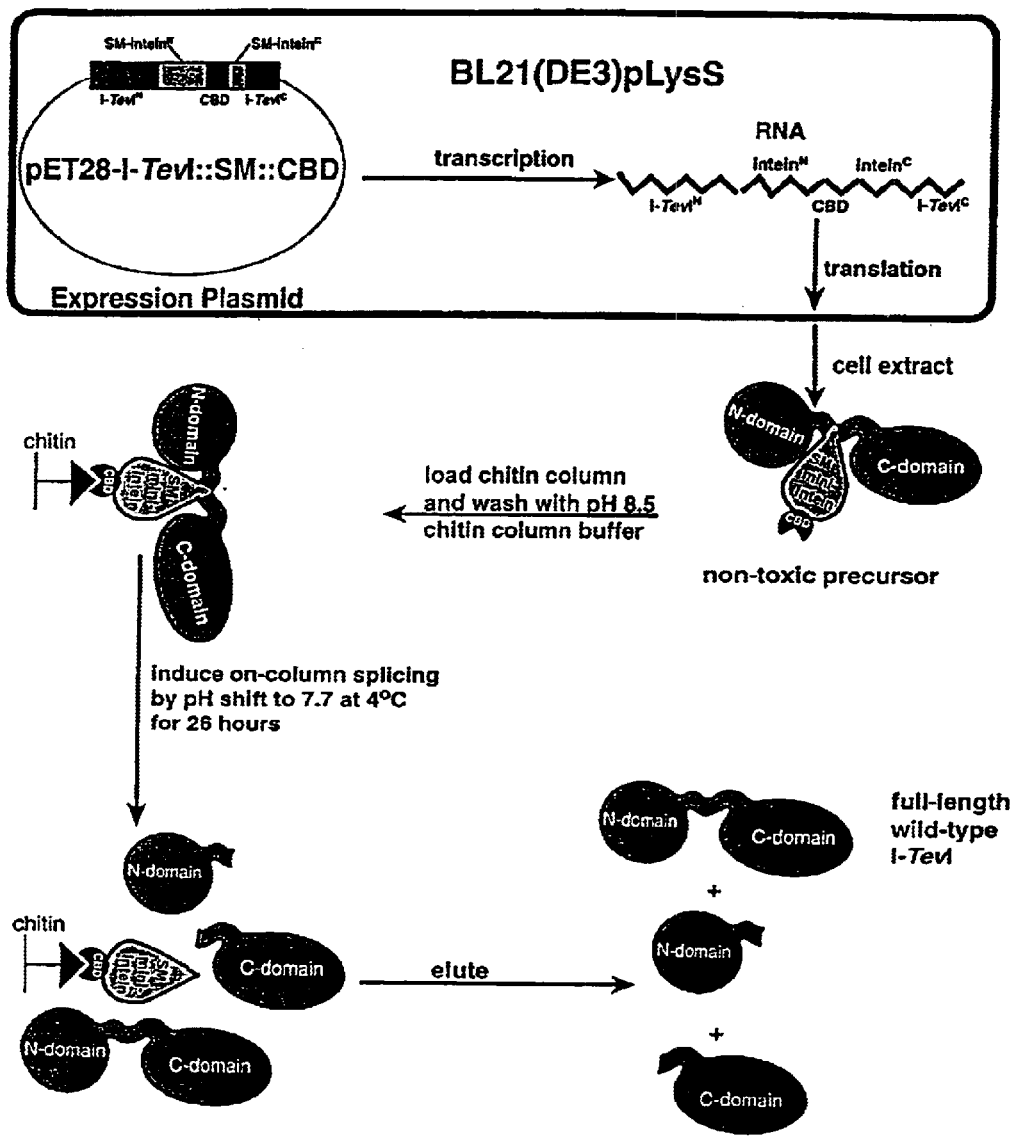
FIG. 19 shows purification scheme of toxic I-TevI by intein-mediated pH-controllable on-column splicing of non-toxic precursor.
Figure 20:
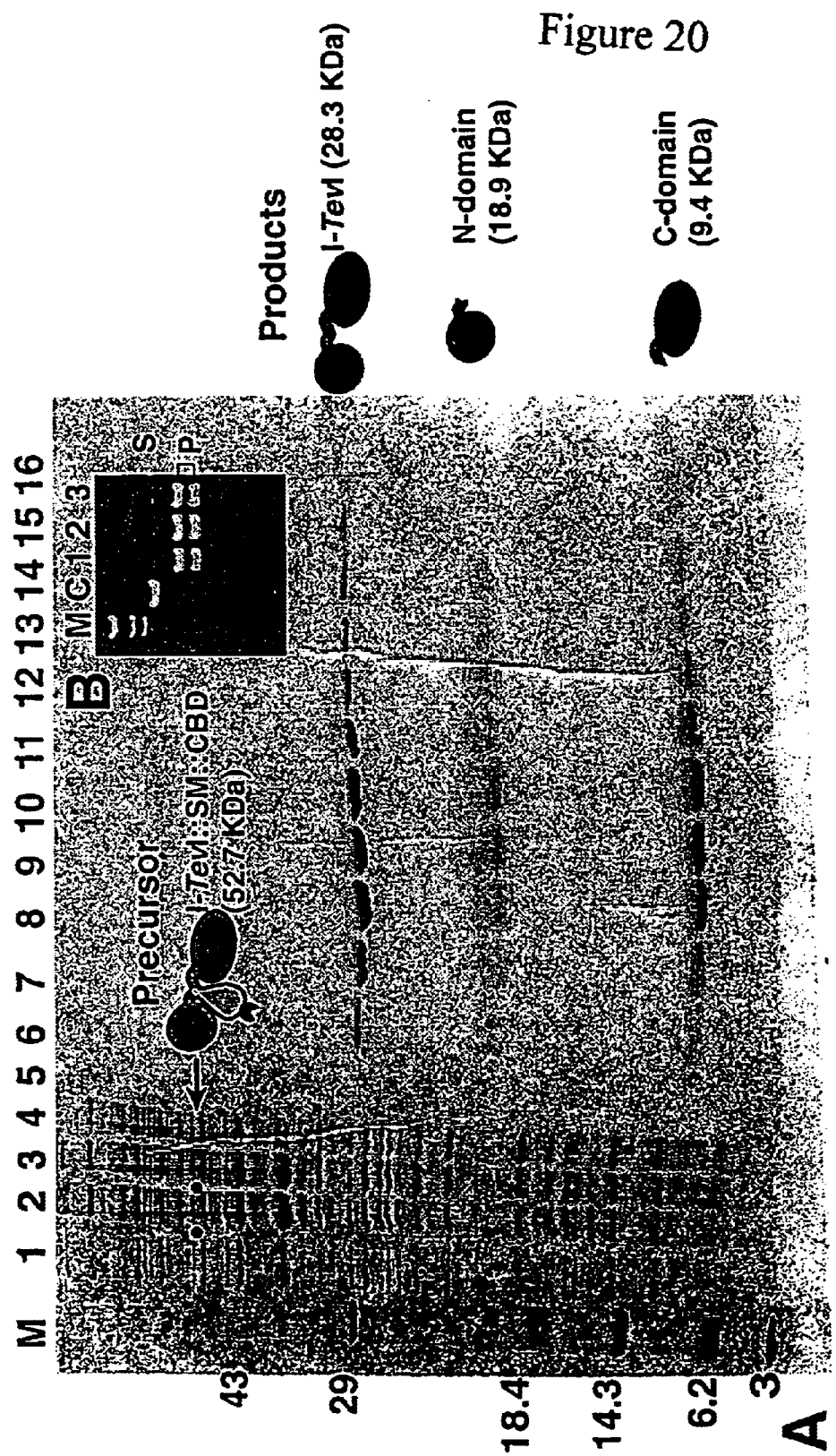
FIG. 20 shows (A) Intein-mediated purification of cytotoxic protein (I-TevI) from the construct depicted in FIG. 4B; and (B) cleavage assays that show that the purified I-TevI is active. In A, Lane M protein molecular weight marker sizes are denoted in kDa. Lane 1 is uninduced sample. Lane 2 is induced sample. is the unspliced fusion precursor I-TevI::SM::CBD. Lane 3 is cleared cell lysate. Lane 4 is chitin column flowthrough. Lanes 5–16 are eluted fractions after on-column splicing at pH 7.7 for 26 hours at 4° C. In B, lane M is lambda HindIII DNA markers. C is control cleavage assay with no enzyme. Lanes 1–4 are cleavage assays performed on purified I-TevI fractions. S is substrate DNA. P is cleavage products.

As illustrated in Example 2, I-TevI, the lethally toxic T4 td intron-encoded homing endonuclease with known domain structure, was used to explore the invention, and is an exemplified embodiment. I-TevI has been inactivated by inserting a modified intein N-terminal to Cys164 and purified the wild-type protein by pH-controllable on-column splicing. FIGS. 4, 19 and 20. This technique can be generalized to other locations in the protein and to apply to other proteins such as toxic proteins. The invention thus encompasses a recombinant molecule encoding I-TevI fused with an intein such that, upon expression of the fusion construct, I-TevI is expressed in amounts suitable for protein purification. This is only possible because, the intein reduces toxicity of I-TevI to a level that allows expression of the protein. After cleavage, intact I-TevI is obtained. Preferably, the construct is that described herein.

Because the Mtu RecA intein occurs naturally before a cysteine residue, which is involved in splicing, the inventors inserted the SM mini-intein in front of Cys 164 at the interface of the joining segment and C-terminal DNA binding domain of I-TevI. This was to reduce the toxicity of I-TevI to a manageable level without severely interfering with proper protein folding (FIG. 4B). To allow rapid purification of the unspliced precursor, the inventors also inserted a chitin-binding domain (CBD) into the SM mini-intein in place of the deleted native endonuclease domain to generate SM::CBD. Although the intein leaves the catalytic domain intact, steric effects of the 220 amino acid SM::CBD cartridge reduce I-TevI function and relieve its lethality. Variability in cell viability possibly due to steric effects and the inverse relation of viability to splicing efficiency are depicted in FIG. 5.

Figure 5:
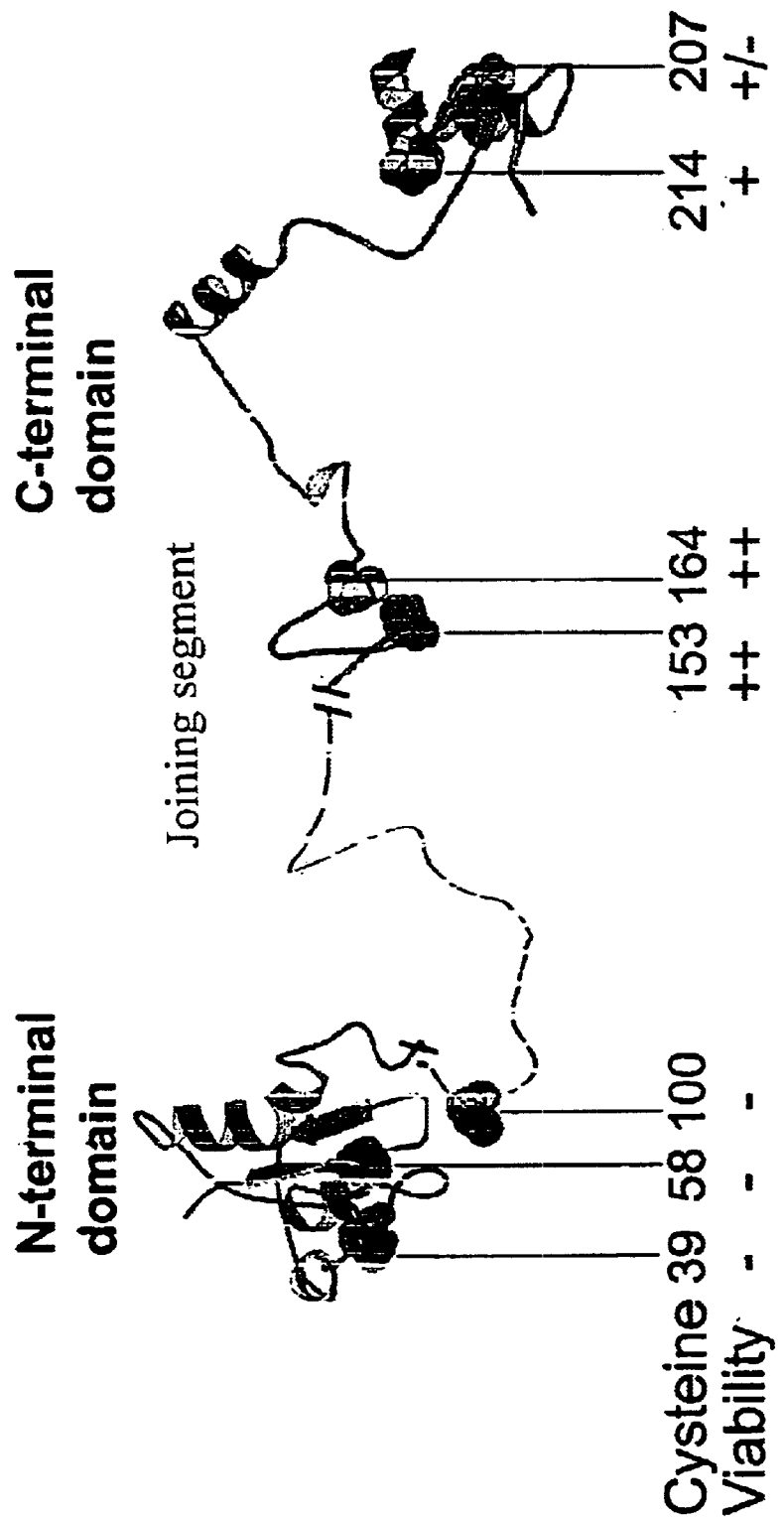
FIG. 5 shows a schematic depicting effect of intein insertions at different specific regions in a toxic protein I-TevI and variability in viability. Viability is proposed to be related to steric effects and inversely related to splicing efficiency.

As illustrated in FIG. 5, intein insertion has region-specific effects. Controllable inteins are more effective in some specific regions or folds and less so in others. Specific regions include, without limitation, the N-terminal domain, the C-terminal domain, flanking segments between the domains and the interfaces between the flanking segments and N-terminal and C-terminal domains. Specific regions can also be identified or characterized by specific conformation such as zinc finger regions, helix-turn-helix, beta-pleated sheets or any other known functional or conformational region. Although these inteins can be more effective if inserted N-terminal to a zinc finger or Cys rich region, other regions or domains of the protein are suitable. In the case of I-TevI, insertion of the intein was most effective in a control-specific manner when placed at the joining segment/C-terminal interface, just N-terminal to a zinc finger region. Such tight control may not always be necessary, I-TevI is an extremely toxic protein, thus other regions may be preferable for different proteins and purification schemes. Suitable regions can be determined empirically; effectiveness of a particular insertion site can be readily assayed for activity as described herein.

The splicing of the SM mini-intein and its derivative SM::CBD was quite slow in this fusion context, especially at low temperatures, which allowed the inventors to maximize the production of non-toxic unspliced precursor by induction at 20° C. for 2 hours. The splicing of the SM mini-intein and its derivative was also pH-sensitive. At pH 8.5 and 4° C., both the splicing rate and C-terminal cleavage rate were extremely slow. When the pH was lowered from 8.5 to 7.4, both the splicing rate and C-terminal cleavage rate increased. When the pH was lowered from 7.4 to 6.0, the C-terminal cleavage rate increased dramatically, exceeding the splicing rate and causing loss of spliced product. The optimal pH range for splicing was between 7.4 and 7.7. The pH-sensitivity of this splicing reaction allowed the inventors to develop a protocol to purify wild-type I-TevI by a pH-shift.

The Examples provided herein show a genetic system that provides self-cleaving inteins; and that the inteins are useful in protein purification; e.g., by inactivation with an intein pH-controllable intein splicing. The invention more broadly provides a method for determining critical, generalizable residues for varying intein activity.

The invention provides a genetic selection system where activity of a modified intein results in a selectable phenotype, allowing rapid generation of useful intein mutants through a combination of rational and random mutagenesis. The screen further provides a variable selection scheme, wherein specific splicing or cleavage rates can be screened at various temperatures. Ultimately, the screen allows the generation of mutant inteins with specific cleaving activities for use in a variety of applications. This method can be used to identify specific amino acid substitutions (and combinations thereof) within the intein that promote desirable activities. In cases where these residues are conserved among inteins, mutant derivatives of other inteins can be generated with substitutions in corresponding residues yielding similar modifications to the wild-type activity. ("Conserved" is used as it is understood in the art; see also FIG. 2 and descriptions thereof herein, where "conserved" is also used.)

More in particular, inteins are phylogenetically widespread, having been found in all three biological kingdoms, eubacteria, archaea and eukaryotes. Inteins undergo autocatalytic splicing at the protein level. Cooper et al. (1993) Bioessays 15:667–674; Colston et al. (1994) Mol. Microbiol. 12:359–363; Perler et al. (1994); and Cooper et al. (1995) TIBS 20:351–356. A nomenclature parallel to that for RNA splicing has been developed, whereby the coding sequences of a gene (exteins) are interrupted by a sequence that specifies the protein-splicing element (intein). Perler et al. (1994). The terms extein and intein refer to both the genetic material and corresponding protein products.

A precursor protein is synthesized comprising exteins interrupted by an intein. Protein splicing then results in intein excision and extein ligation, which restores the uninterrupted sequence to the now intein-less protein. Highly conserved residues appear at the junction of the inteins and the exteins. His (H) and Asn (N) occur at the C-terminal end of the intein and Ser (S), Thr (T) or Cys (C) occur immediately downstream of each splice junction.

Inteins can be used in a variety of applications wherein intein fusion to a desired target protein facilitates the expression, purification or study of the target protein. In these applications, modified inteins are usually required. Heretofore, difficulties arose when all available inteins could not fulfill the requirements for the desired application, either due to lack of appropriate activity, uncontrollable activity or low activity. In these cases, rational mutagenesis typically cannot provide the required activity and an additional mutagenic strategy is required. Intein splice junction residues can be modified to prevent the natural splicing activity from occurring, leaving only the C-terminal cleavage activity. However, the resulting activity is too slow for utility in biotechnology applications. Random mutagenesis coupled with a genetic screen are herein combined with rational mutagenesis to isolate intein mutants with optimum combinations of engineered traits and desirable activity.

For this strategy to work desirably it should allow rapid evaluation of intein mutants, and therefore requires an effective screen for linking intein activity to an easily observable or selectable phenotype. Furthermore, the screen should allow selection of desired traits under conditions that are relevant for the proposed application. An earlier screen (U.S. Pat. No. 5,795,731), based on internal fusion of the M tuberculosis intein to the thymidylate synthase enzyme provides a method for linking intein splicing activity to growth phenotype on thymineless media. However, this system does not link cleavage activity to phenotype and does not provide a method for selecting specific levels of activity at various temperatures. Thus, methods of the '731 patent, can be modified by using inteins of the invention; and, the invention encompasses modifications thereof using embodiments herein.

An intein derivative exhibiting controllable cleavage activity has been isolated using rational and random mutagenesis followed by a genetic screen. The screen is based on the ability to select for and against thymidylate synthase function in *E. coli*. A plasmid was constructed to overexpress a tripartite fusion of maltose binding protein/intein/thymidylate synthase. Previous systems for mutant selection were based on interruption of the reporter by internal fusion with the intein. Here the selection for cleavage mutants is achieved by external fusion to the reporter. This tripartite reporter is useful to the selection of controllably cleaving inteins. The basis of the selection is that the tripartite fusion has no TS activity, while C-terminal intein cleavage yields active thymidylate synthase assayable both in vivo and in vitro.

For the work described herein the starting intein was a 168 amino acid mini-intein derivative of the Mtu RecA intein (Derbyshire et al. (1997b) with a mutation of Cys1 to Ala to preclude N-terminal cleavage and splicing. A pool of randomly mutated PCR fragments encoding the mini-intein derivative was cloned into the reporter plasmid to generate a pool of plasmids expressing randomized copies of the tripartite fusion. The pool was transformed into *E. coli* D1210ΔthyA and colonies were grown on defined medium plates in the absence of thymine at 30° C. These culture conditions select for cells with functional TS activity derived from C-terminal cleavage of the intein contained in the tripartite fusion. Further screening for growth on minimal plates at a variety of temperatures combined with in vitro experiments to detect temperature-sensitive cleavage of overexpressed fusion protein, confirmed that a controllably cleaving intein had been obtained. In vitro experiments were also used to demonstrate that the intein was pH sensitive with cleavage being induced upon shifting from pH 8.5 to pH 6.0. The mini-intein mutant described herein (ΔI-CM) displays elevated cleavage activity compared to both the full-length Mtu intein and its mini-intein parent making it particularly useful for application in affinity separations. This increased activity is the result of an amino acid substitution (Asp 422 to Gly) that could not have been predicted based on current knowledge of intein structure and function (Wood et al. (1999a); Example 1).

Indeed, Applicants have sequenced six additional high cleavage mutants and have found that all have the D422G mutation. Thus, the invention encompasses any non-naturally occurring intein, either truncated or full-length, with a D to G mutation or more generally with G, a location corresponding to residue 422 of the full-length Mtu intein, by sequence homology, as well as nucleic acid molecules, e.g., DNA, encoding such inteins with such a D to G mutation or G in that location. For instance, a DNA molecule having a codon for G rather than D in the position corresponding by sequence homology to the codon for residue 422; e.g., instead of GAU or GAC there is GGU, GGC, GGA or GGG in the DNA sequence for the amino acid corresponding to residue 422 of the full-length Mtu intein. Such a DNA molecule that has sequence homology to the DNA sequence for the Mtu intein can also hybridize to the DNA for the Mtu intein; for instance under stringent conditions.

Similarly, the invention encompasses any non-naturally occurring intein, either truncated or full-length, with a V to L mutation or more generally with L, in a location corresponding to residue 67 of the full-length Mtu intein, by sequence homology, as well as nucleic acid molecules, e.g., DNA, encoding such inteins with such a V to L mutation or L in that location. For instance, a DNA molecule having a codon for V rather than L in the position corresponding by sequence homology to the codon for residue 67; e.g., instead of GUU, GUC, GUA or GUG there is AAA or AAG in the DNA sequence for the amino acid corresponding to residue 67 of the full-length Mtu intein. Such a DNA molecule that has sequence homology to the DNA sequence for the Mtu intein can also hybridize to the DNA for the Mtu intein; for instance under stringent conditions.

"Sequence homology" can refer to the situation where nucleic acid or protein sequences are similar because they have a common evolutionary origin. "Sequence homology" can indicate that sequences are very similar. Sequence similarity is observable; homology can be based on the observation. "Very similar" can mean at least 70% identity, homology or similarity, advantageously at least 75% identity, homology or similarity, more advantageously at least 80% identity, homology or similarity, even more advantageously at least 85% identity, homology or similarity, yet even more advantageously at least 90% identity, homology or similarity, such as at least 93% or at least 95% or even at least 97% identity, homology or similarity. The nucleotide sequence similarity or homology or identity can be determined using the "Align" program of Myers et al. (1988) CABIOS 4:11–17 and available at NCBI. Additionally or alternatively, amino acid sequence similarity or identity or homology can be determined using the BlastP program (Altschul et al. Nucl. Acids Res. 25:3389–3402), and available at NCBI. Alternatively or additionally, the terms "similarity" or "identity" or "homology", for instance, with respect to a nucleotide sequence, is intended to indicate a quantitative measure of homology between two sequences. The percent sequence similarity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC (SEQ ID NO:6) will have a sequence similarity of 75% with the sequence AATCAATC (SEQ ID NO:7) ($N_{ref}=8$; $N_{dif}=2$).

Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm. (1983) Proc. Natl. Acad. Sci. USA 80:726. For instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity with DNA sequences, thymidine (T) in the DNA sequence is considered equal to uracil (U) in the RNA sequence. The following references also provide algorithms for comparing the relative identity or homology or similarity of amino acid residues of two proteins, and additionally or alternatively with respect to the foregoing, the references can be used for determining percent homology or identity or similarity. Needleman et al. (1970) J. Mol. Biol. 48:444–453; Smith et al. (1983) Advances App. Math. 2:482–489; Smith et al. (1981) Nuc. Acids Res. 11:2205–2220; Feng et al. (1987) J. Molec. Evol. 25:351–360; Higgins et al. (1989) CABIOS 5:151–153; Thompson et al. (1994) Nuc. Acids Res. 22:4673–480; and Devereux et al. (1984) 12:387–395. "Stringent hybridization conditions", is a term which is well known in the art; see, for example, Sambrook, "Molecular Cloning, A Laboratory Manual" second ed., CSH Press, Cold Spring Harbor, 1989; "Nucleic Acid Hybridization, A Practical Approach", Hames and Higgins eds., IRL Press, Oxford, 1985; See also FIG. 2 and description thereof herein wherein there is a sequence comparison.

An additional refinement of TS reporter screens (either with internal fusion as described by the '731 patent or in external fusion as described herein) is the application of the drug trimethoprim to select for inteins with reduced activity as part of a strategy to generate controllable intein mutants. Suitable strategies are illustrated in Example 3 and FIG. 6.

The inventors, in Example 1, have taken advantage of the thymidylate synthase (TS) reporter system in a number of gene fusion contexts with derivatives of the Mtu RecA intein. However, the invention is not limited to (1) the TS reporter system or (II) the Mtu RecA intein.

(I) The invention is applicable to any reporter system. Many alternate reporter systems can be used in similar internal and external gene fusion contexts to provide screen (s) for inteins with desirable properties. Advantageously, the reporter genes should be easily assayable in vivo and/or in vitro and include, but are not limited to, β-galactosidase, galactokinase, luciferase and alkaline phosphatase, as examples of reporters with enzymatic assays, β-lactamase as an example of a reporter conferring antibiotic resistance, and green fluorescent protein as an example of a reporter providing a direct calorimetric assay.

(II) The invention is applicable to all inteins, both naturally occurring and modified for size, insertion of other proteins (or protein domains) and for desirable functional attributes; e.g., any intein can be used in the practice of the invention, with external or internal fusion contexts with TS or other reporter genes (examples of which are given in (I) above).

Controllable intein mutants derived from the Mtu RecA intein can have amino acid substitutions in residues conserved in all inteins. For example, the ΔI-CM mutant intein described above has a mutation in a residue conserved among inteins (Wood (1999); Example 1). In principle, one skilled in the art, from this disclosure and the knowledge in the art, without undue experimentation, can construct mutant derivatives of other inteins with substitutions in corresponding residues which will have similar activities but which may prove superior for specific applications.

Details for the genetic scheme used to isolate a controllable self-cleaving intein (ΔI-CM) and its utility in protein purification are given in Wood et al. (1999) and Examples 1, 2 and 3; and, FIG. 6 describes the trimethoprim screen.

Figure 7:
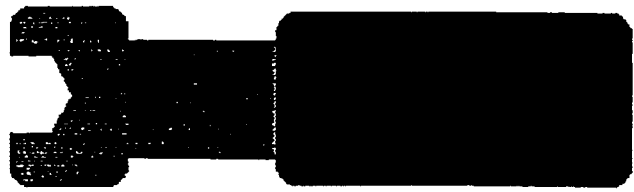
FIG. 7 shows highlights of the advantages of the invention, e.g., preventing initial acyl shift, cleavage mediated by succinimide formation, and providing a miniature intein mutant derived from Mtu RecA intein (18 kDa).

FIGS. 7 to 18 additionally illustrate the invention, and further show that the invention is broader than the exemplified embodiments, inter alia. FIG. 7 provides highlights of the advantages of the invention, e.g., preventing initial acyl shift, cleavage mediated by succinimide formation, and providing a miniature intein mutant derived from Mtu RecA intein (18 kDa). FIG. 7 introduces a graphic representation of a wrench. The handle portion of the wrench is to represent the reporter (e.g. TS). The wrench stem portion, between the wrench-head (where a nut or bolt head would matingly engage the wrench) and the handle, is to represent the intein. And, the wrench-head is to represent a binding domain (with the nut or bolt-head in other Figures representing that which binds to the binding domain).

Figure 8:
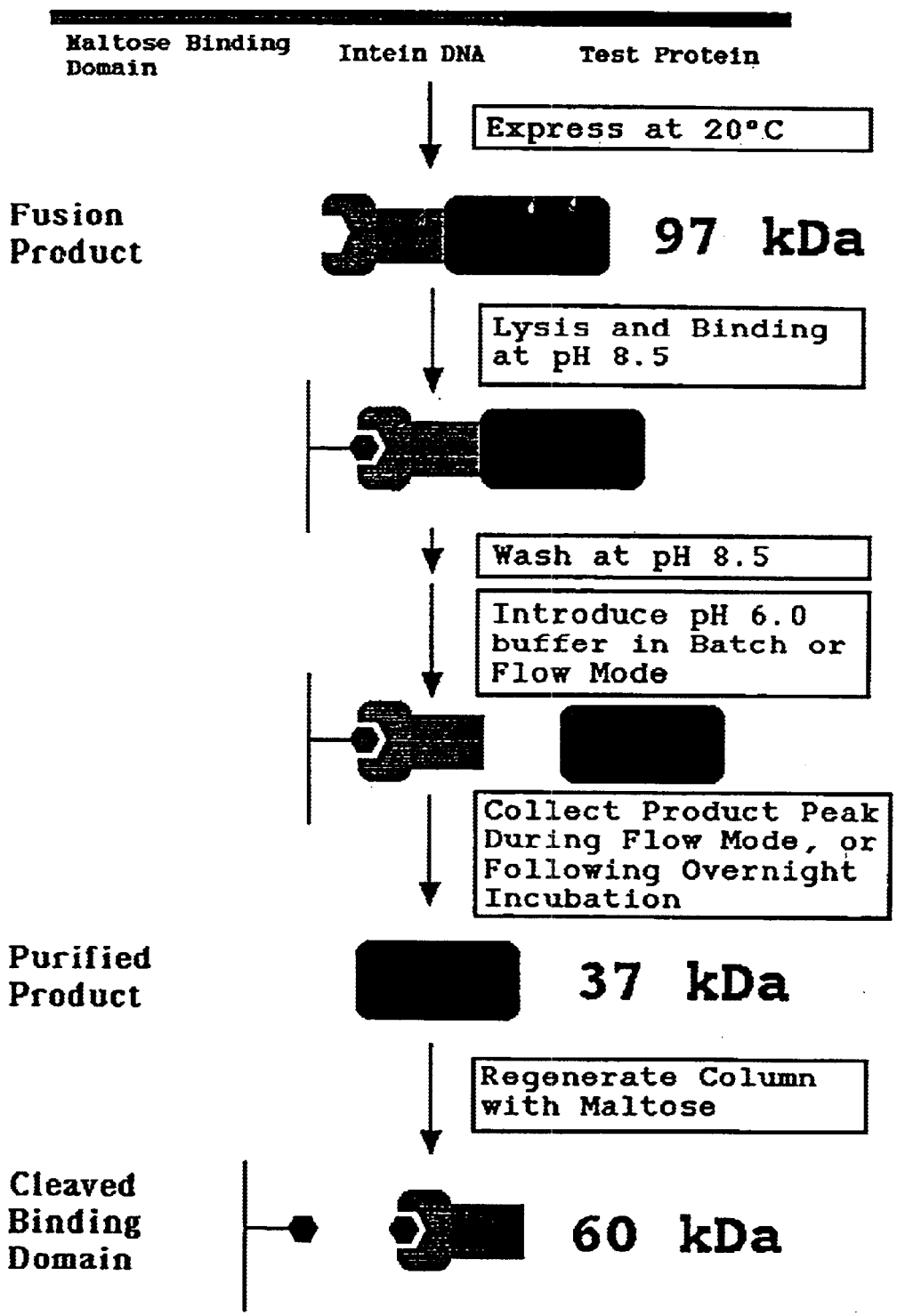
FIG. 8 shows an affinity protocol.
Figure 9:
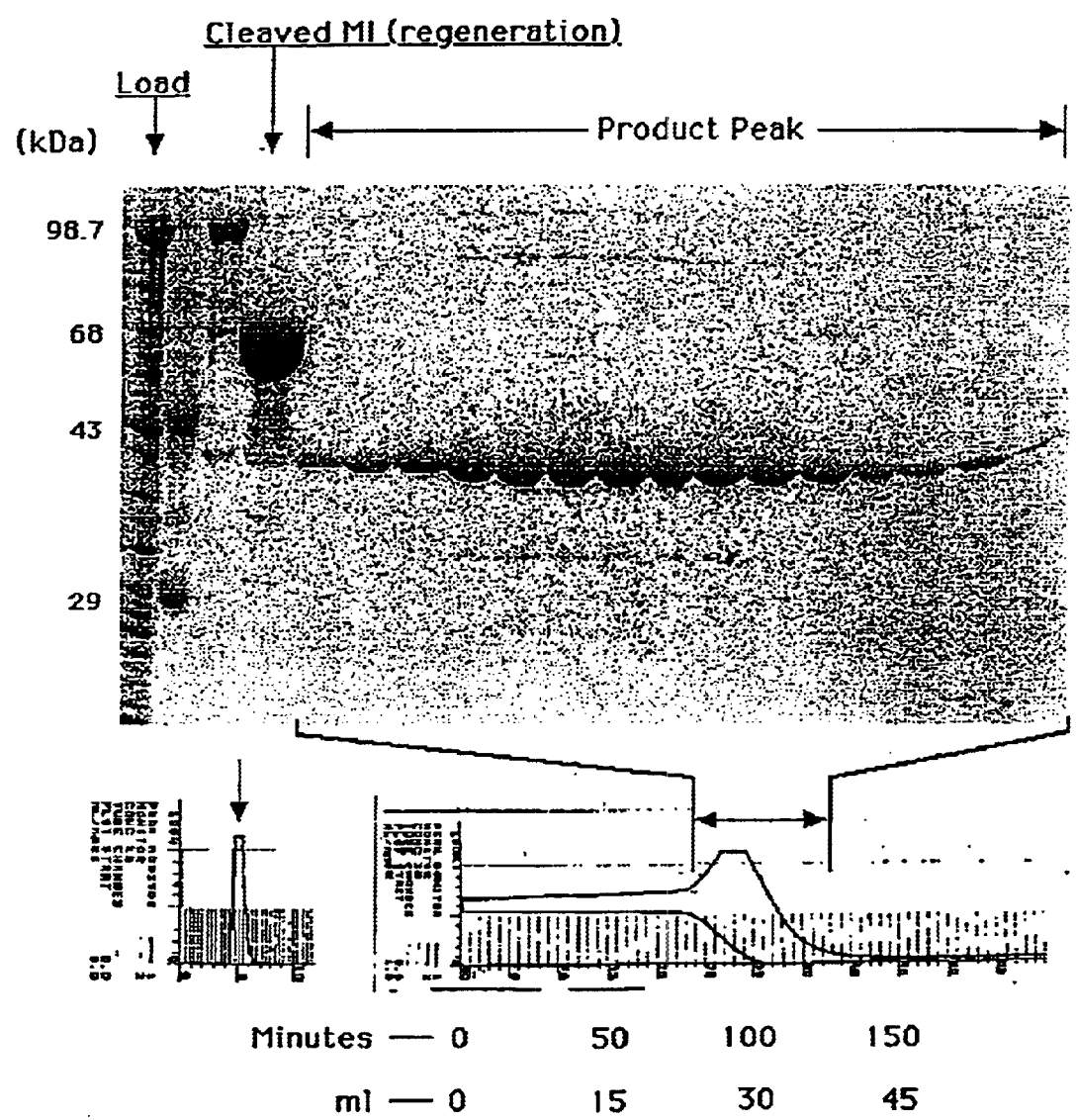
FIG. 9 shows an exemplified flow mode at 30° C. (column residence time, 1 hr).
Figure 10:
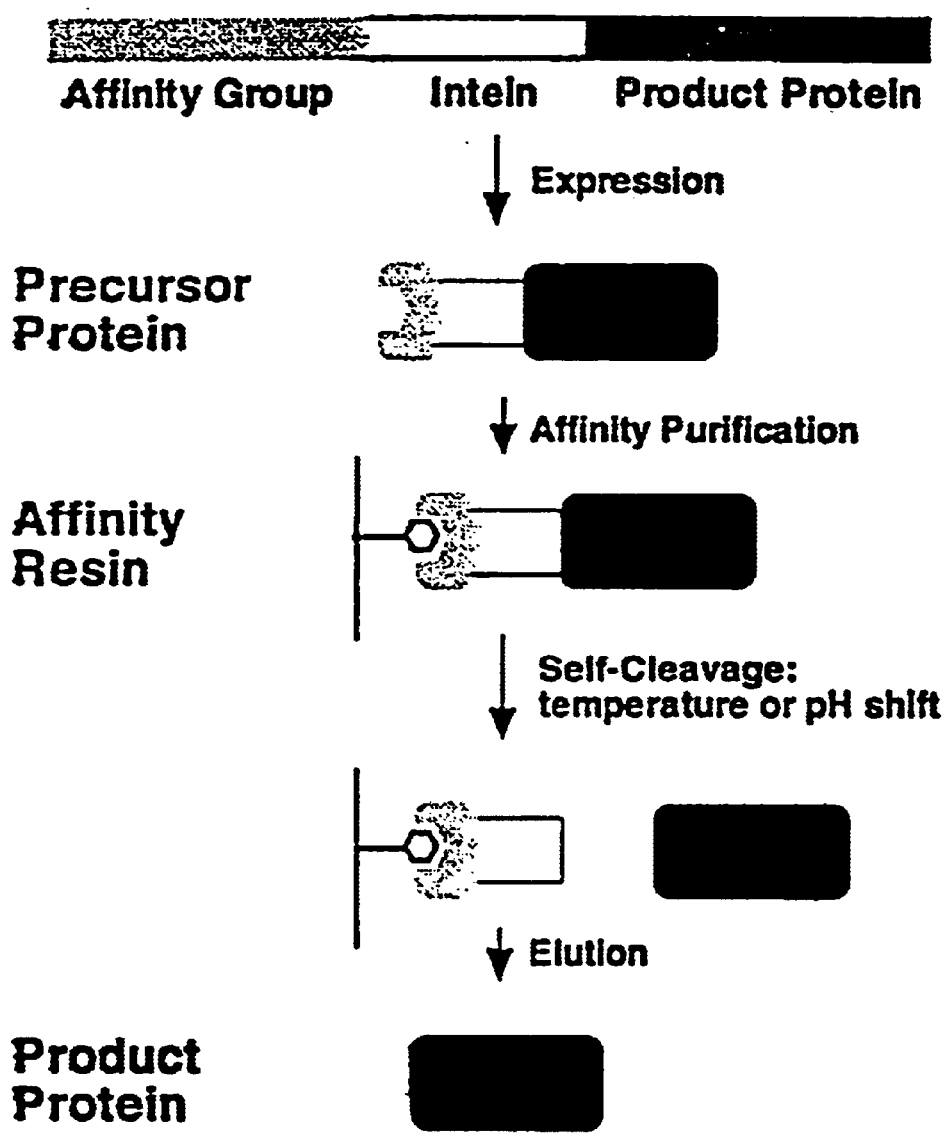
FIG. 10 is discussed in the Specification.
Figure 11:
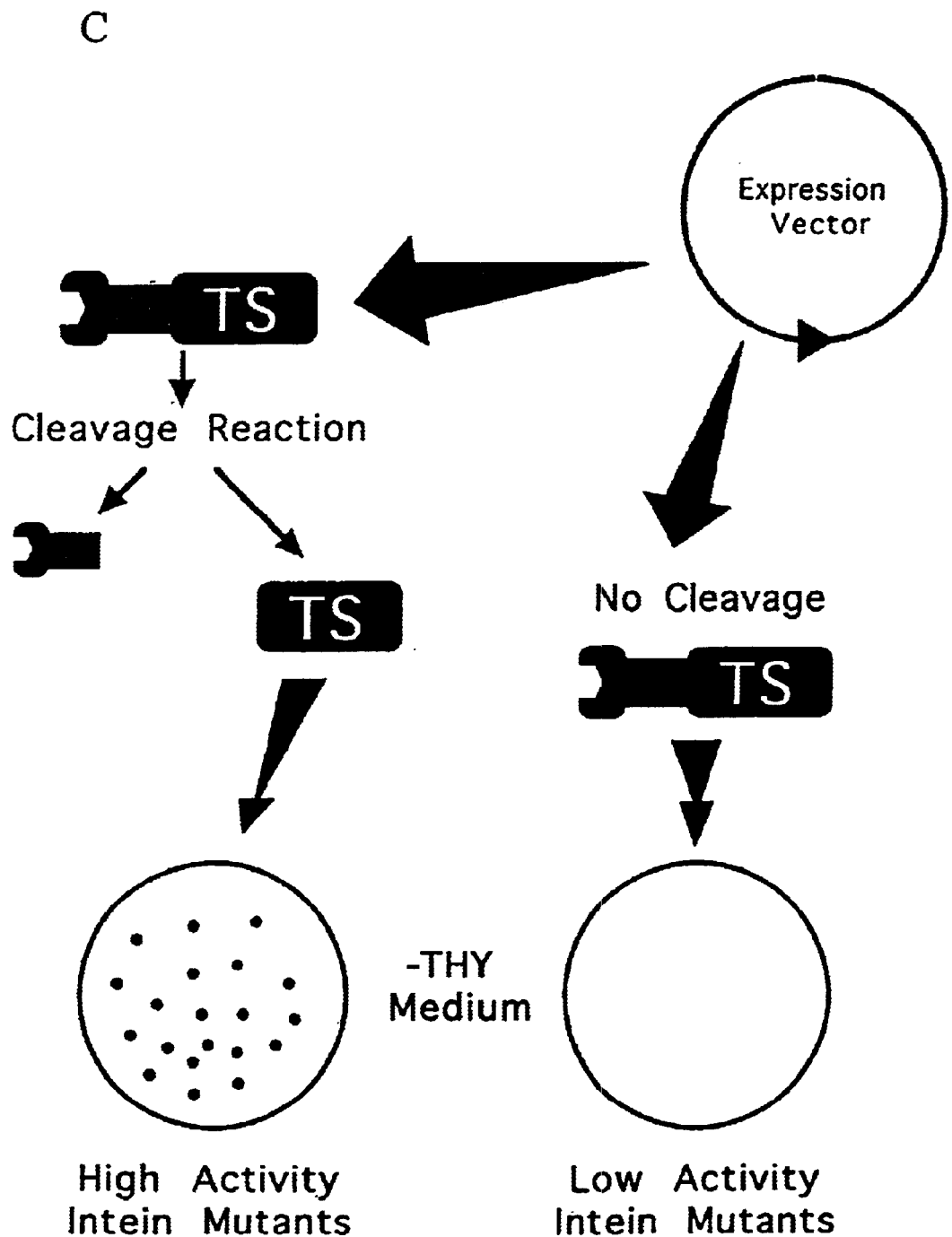
FIG. 11 is discussed in the Specification.
Figure 12:
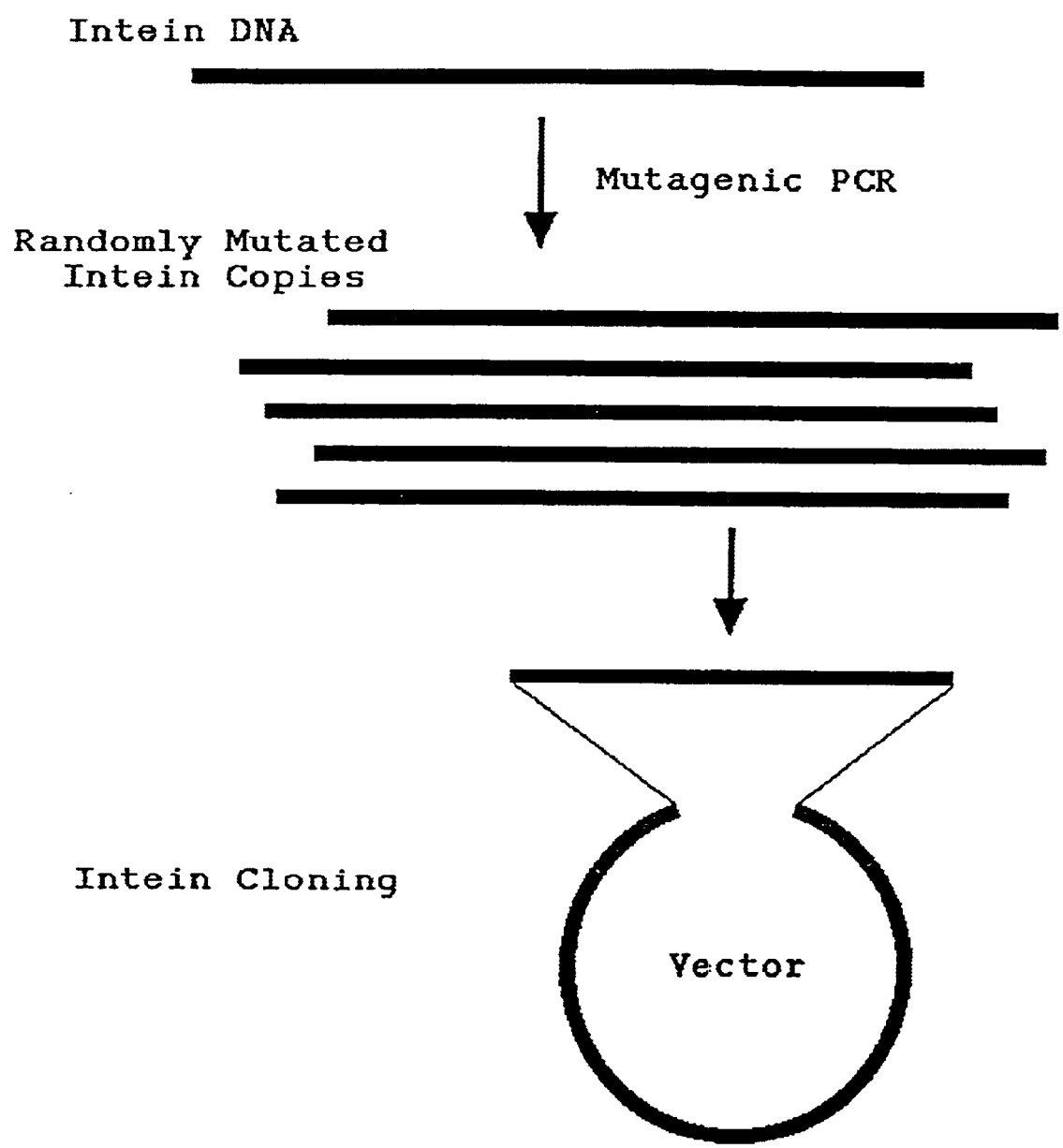
FIG. 12 shows the mutagenesis and cloning of inteins.

FIG. 8 provides an affinity protocol. At the top of the Figure, a bar represents a nucleic acid molecule, e.g., DNA, encoding a fusion product, such as a tripartite fusion protein, e.g., including a binding domain, such as a maltose binding domain, intein, and reporter system or test protein portion. The fusion product is expressed, e.g., at 20° C. In an exemplified embodiment, the product can have a molecular weight of 97 kDa. The fusion product is represented by a wrench. The fusion product can then be isolated from the expression system (e.g., lysis; for instance, at pH 8.5); and, the fusion product can be bound to that which binds to the binding domain (e.g., maltose; for instance, at a pH that does not cause separation of a portion or portions of the fusion product, e.g., pH 8.5). By being so bound, the fusion product can be bound to a column; for instance, that which binds to the binding domain of the fusion product ("the binding protein") can also be bound to a particle or to a column (e.g., a particle packed in a column). The bound fusion product can be washed; for instance, at pH 8.5. The bound fusion product can then be subjected to a pH change to cause a portion or portions of the fusion product to separate from the fusion product; e.g., to cause the test protein or reporter system to be separated (e.g., washed) from the fusion product. The separated portion, e.g., test protein, can then be collected as a purified product (exemplified as a 37 kDa protein). The remainder of the fusion product can then be contacted with an excess of that which binds to the binding domain; for instance, a column can be regenerated (e.g., with maltose), or to that which otherwise thereby causes the release of the remainder of the fusion product (with or without the binding protein) if it is bound via the finding protein. (See the Examples). FIG. 9 illustrates an exemplified flow mode at 30° C. (column residence time, 1 hr; see also the Examples).

FIGS. 10A and 10B more generally illustrate the protocol of FIG. 8. The DNA to express the fusion product includes DNA encoding an affinity group or ligand binding domain, the intein, and product protein. That DNA is expressed, e.g., in a vector system, such as E. coli; thus the DNA can be in the form of a plasmid. The DNA thus goes through transcription and translation and a fusion protein, e.g., a tripartite fusion protein is expressed. The expressed fusion protein is then bound to a solid matrix via the affinity group or ligand binding domain. The bound expressed fusion protein can then washed and subjected to cleavage or directly subjected to cleavage. Cleavage can be autocatalytic cleavage, for instance, triggered by a change in physical condition(s) and/or chemical condition(s) e.g., a change in one or more physical condition and/or one or more chemical condition (such that a combination of physical condition(s) and chemical condition(s) being possible), for instance, any one, or more, or a combination of any two or all, of change in pH, temperature, oxidative potential and ionic strength. The result can then be a cleavage of the product protein from the fusion product, with isolation of the purified product protein resulting therefrom (e.g., rinsing column after triggering autocatalytic cleavage or elution of product from column, to obtain purified protein).

Thus, the invention encompasses expression of a fusion protein including a ligand binding domain or affinity group, an intein and a product protein, advantageously with the ligand binding domain or the affinity group and the product protein separated by an intein. (The intein is advantageously an inventive intein that is a controllable self-cleaving intein; e.g., an intein obtained by random mutagenesis and a genetic screen. For instance, the intein can be obtained as discussed herein, e.g., with reference to other Figures or the Examples, the randomly mutated intein DNA encoding mutants, e.g., truncated mutants or mutants having amino acid substitutions or truncated mutants having amino acid substitutions, are expressed in a vector system as part of a tripartite fusion protein, with the product protein in that instance being a reporter protein and colonies grown for selection of the reporter protein being functional. Preferably, the reporter protein is functional from C-terminal cleavage of the intein within the tripartite fusion protein. The selection can show that the reporter protein is functional at a particular temperature, i.e., that cleavage occurs at a particular temperature or temperature range and ergo that the intein cleaves at a particular temperature or temperature range or that the intein is controllable at a particular temperature or temperature range. Optionally and advantageously, the tripartite fusion protein can be in vitro screened to ascertain pH sensitivity, e.g., pH ranges where the reporter protein is functional and ergo that intein cleavage occurs at a particular pH or pH range. Similar in vitro screening can be done to ascertain ionic strength or concentration or ranges thereof that obtains functional reporter protein activity and ergo intein cleavage. From this, one can select a mutant intein, such as the exemplified mutant intein, which can be controlled by varying one or more of pH, temperature, oxidative strength and ionic strength; and, such a controllable intein can be used in fusion proteins in processes for obtaining a desired product protein). Binding the expressed fusion protein to a particle or matrix such as a solid matrix, e.g., column, derivitized with the binding ligand. Optionally and advantageously washing the bound fusion protein to remove contaminants. Inducing cleavage of the product protein from the binding domain, e.g., with a pH shift and/or an increase in temperature and/or a change in ion concentration or presence or absence and/or change in oxidative potential (e.g., pH shift from 8.5 to 6.0 and/or change to room temperature, e.g., to about 20 or 25° C. and/or to about 30° C.); and collection of the product protein, e.g., from a column.

FIGS. 11A and 11B further describe the thymidylate synthase reporter system and the folate cycle (See the Examples). More in particular, FIGS. 11A and 11B illustrate a genetic scheme used to isolate a controllable self-cleaving intein. Tripartite fusion protein derivatives are expressed from the expression vector. High activity intein mutants cleave readily, rendering the E. coli host TS+ and able to grow on -THY medium, whereas low or no activity intein derivatives (no cleavage) render the host TS— and therefore unable to grow on -THY medium (see FIG. 11B top portion). As discussed herein, other reporter systems can be employed in the practice of the invention. FIG. 11A, in the lower portion illustrates the folate cycle. Optimization of enzymes in non-native synthesis pathways via directed evolution had heretofore been impractical; for instance, due to low throughput in isolating beneficial mutations. These limitations can be overcome by engineered folate consuming pathways; creating a link between growth phenotype and pathway folate consumption. Availability of the methylation cofactor tetrahydrofolate can be regulated by the drug trimethoprim, resulting in trimethoprim-dependent arrested cell growth due to metabolic competition for tetrahydrofolate. Efficiency of folate-consuming engineered pathways can thus be indicated by host sensitivity to trimethoprim. Accordingly, by tuning the trimethoprim level in selected media, cells harboring advantageous mutations in the engineered pathway can readily be differentiated by growth phenotype, eliminating the need for cumbersome analytical techniques in mutant evaluation. Differential folate consumption by engineered pathways is indicated by a simple growth phenotype in the presence of varying levels of trimethoprim. A screen for incremental increases in limiting enzyme activity based on mutation effects on overall pathway efficiency and resulting increases in folate consumption is provided herein (See also FIG. 6 and the Examples).

FIG. 13 illustrates the mutagenesis and cloning of inteins. The intein DNA is subjected to mutagenic PCR, generating randomly mutated intein copies (fragments). The fragments are inserted into a vector (e.g., plasmid); e.g., so as to be expressed as the middle piece of a tripartite fusion; and, the expression products are then screened; e.g., for reporter activity at varying temperatures, and/or pH and/or ion concentration/presence/absence and/or oxidative potential.

Figure 14:
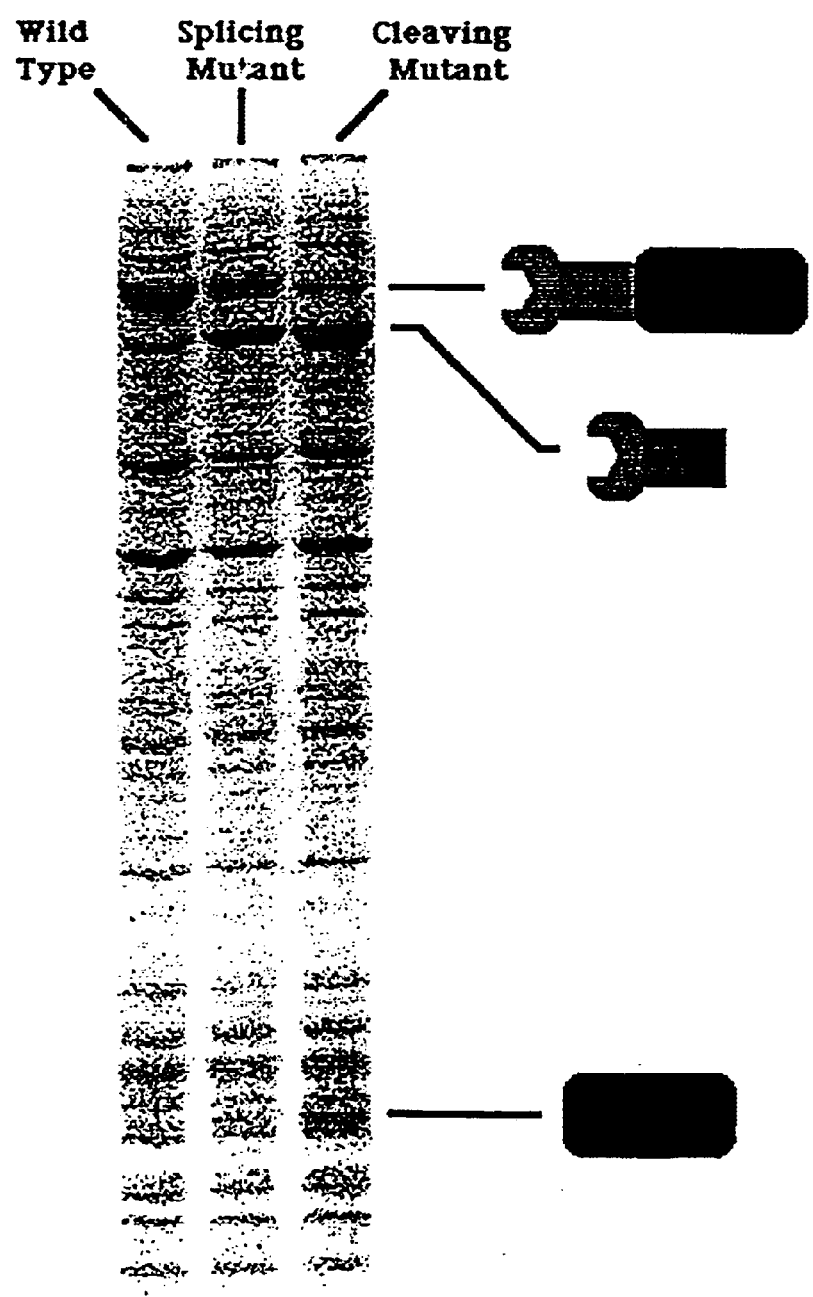
FIG. 14 shows enhanced splicing and cleavage mutant mini-inteins.

FIG. 14 illustrates the intein-screening premise. When the intein is within the reporter (TS) it interferes with its activity if there is no splicing, whereas there is activity if there is splicing. In a tripartite fusion, there is no activity if the intein is non-cleaving, whereas there is activity if the intein is cleaving.

Figure 15:
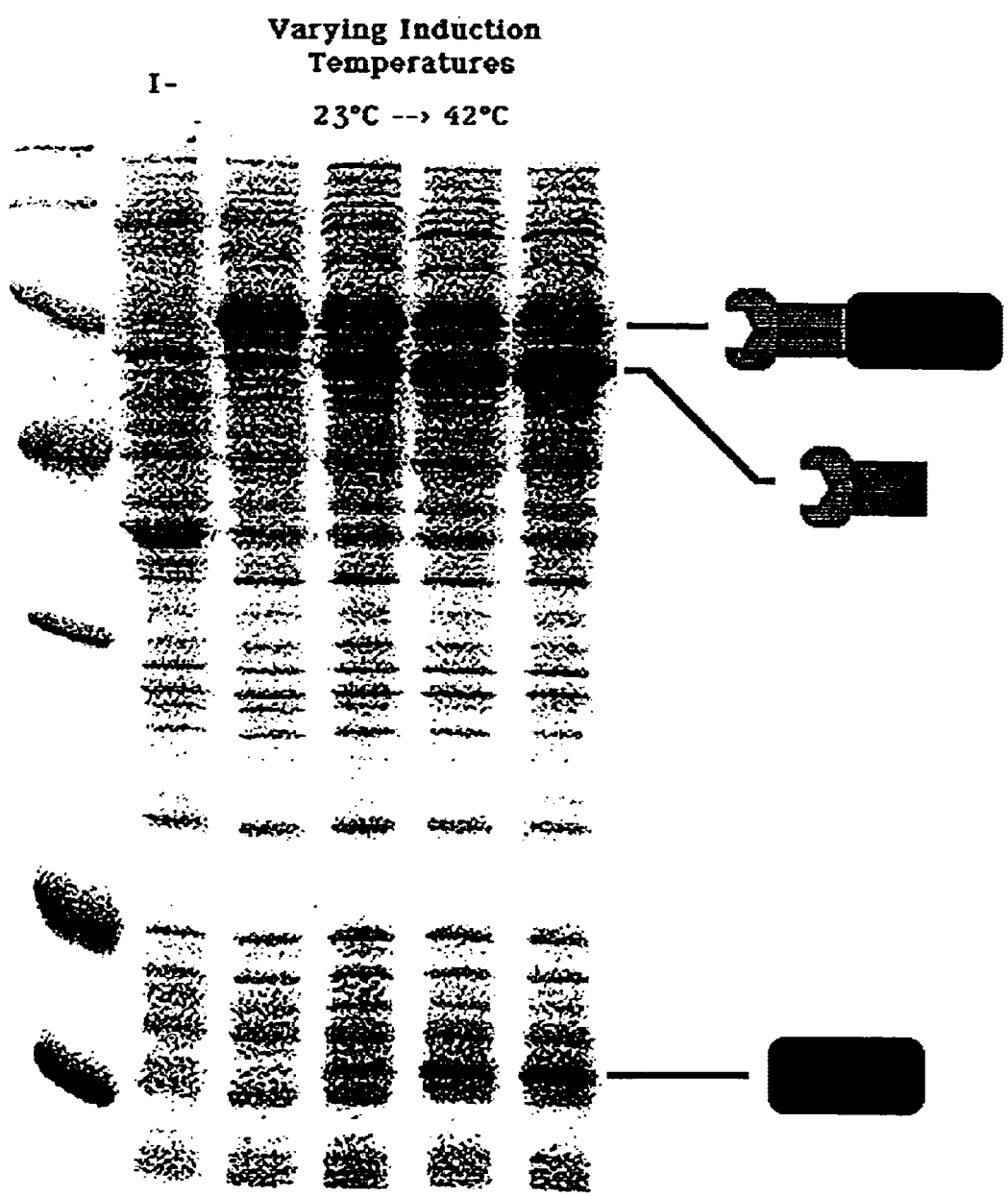
FIG. 15 shows temperature sensitive cleavage for the SM and CM mutants.

FIGS. 14 and 15 show enhanced cleavage mutant and temperature sensitive cleavage. These Figures employ the wrench and portion thereof illustration of other Figures. In FIG. 14, the left side is wild-type, the middle is splicing mutant (SM), and the right side is the cleaving mutant (CM). In both Figures, the product for the tripartite fusion is shown by the full wrench, the product from the product protein or reporter protein is shown by the wrench handle, and the wrench head and stem indicate the product of the binding moiety and intein (below the full tripartite fusion). FIG. 15 shows that induction temperatures were varied between 23° C. and 42° C. Thus, a range of temperatures useful in embodiments of the invention, e.g., screening embodiments or controlled intein activity (such as protein production embodiments) can be from about 4 to about 42° C., such as from about 4° C. to about room temperature. That is, about 20 to about 25° C. such as about 23° C., and/or from about room temperature, e.g., about 20 to about 25° C. such as about 23° C., to about 42° C. This includes, for example, from about 23° C. to about 30° C., about 23 to about 37° C. and about 37° C. to about 42° C., inter alia).

Figure 16:
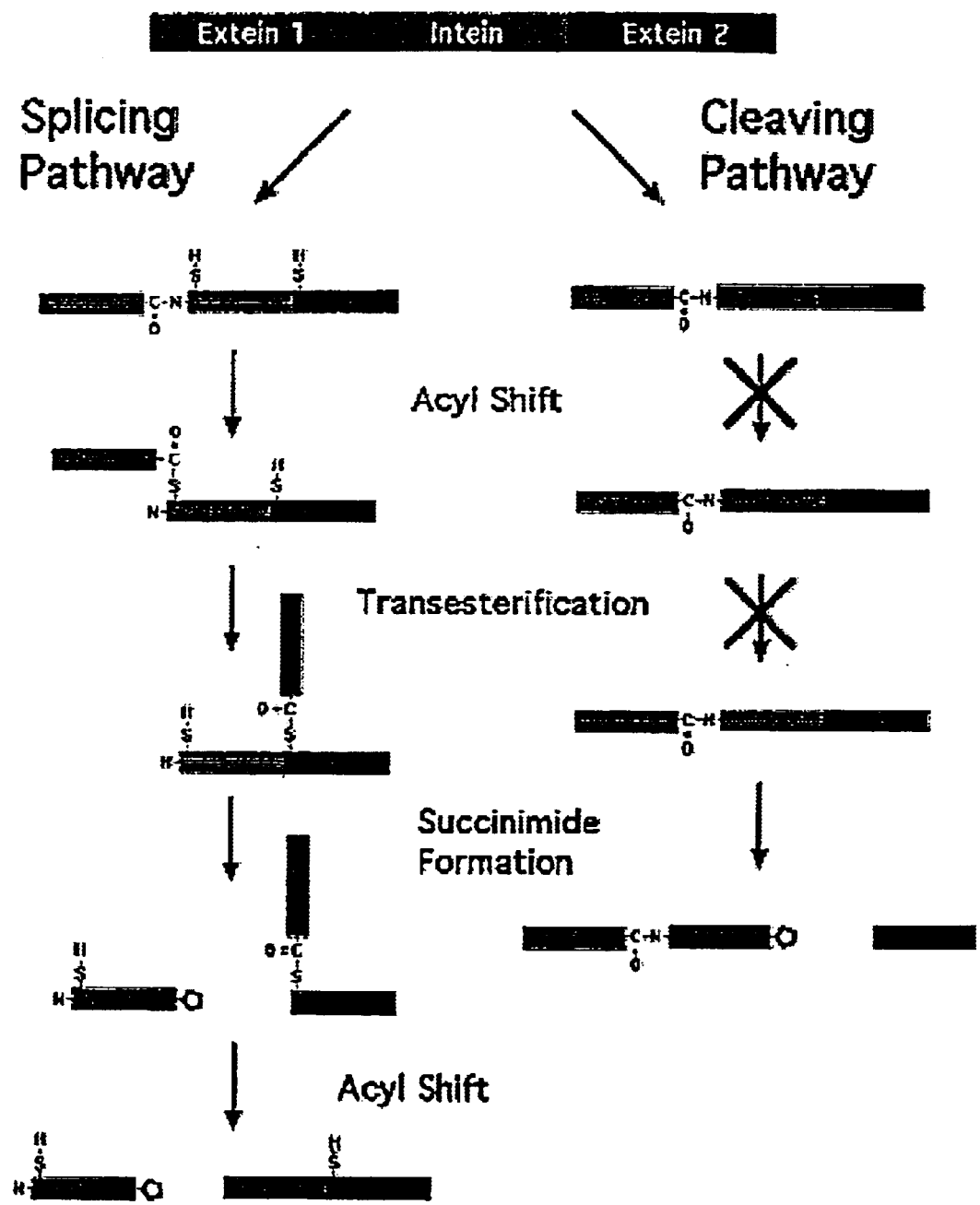
FIG. 16 shows cleaving modification; namely, the splicing pathway and the cleaving pathway.

FIG. 16 illustrates cleaving modification; namely, the splicing pathway and the cleaving pathway. Note, there is no acyl shift or transesterification in the cleaving pathway, whereas these are present in the splicing pathway, with succinimide formation in both pathways, with acyl shift following succinimide formation in the splicing pathway.

FIG. 17A illustrates pH effect on cleavage activity (product conversion vs. pH, during a 15 minute incubation, pH 8.5 to 6.0), using the wrench and portion thereof illustration of other Figures, with FIG. 17B providing cleavage rate constant vs. pH, similar to the presentation in FIG. 3

FIG. 18 also includes a portion of that which is also depicted in FIG. 3). More in particular, FIG. 18 provides a reproduction of SDS PAGE gels to demonstrate purification of proteins from tripartite precursors (using the wrench and portion thereof illustration of other Figures). The proteins are (A) 130C, the C-terminal DNA binding domain of I-TevI, an intron-encoded endonuclease of bacteriophage T4; (B) the alpha subunit of E. coli RNA polymerase; and (C) catabolite activator protein (CAP) of E. Coli. Cleavage of tripartite precursors to release 130C and CAP was achieved by a shift from pH 8.5 to pH 6, while release of the alpha subunit was achieved by an increase in temperature to 30° C. in addition to the pH shift. Thus, intein control can be by changing a physical parameter (e.g., temperature) or by changing a chemical parameter (e.g., pH or ion concentration/presence/absence or oxidative potential), or a combination of physical parameter(s) and chemical parameter(s) (e.g., temperature and pH). (Varying of other physical parameters for controlling intein cleavage and/or splicing is also possible; e.g., volume, pressure, etc.). In each panel, the lanes marked I are crude cell extracts containing induced tripartite precursor protein (*); lanes marked product show fractions containing eluted product protein after pH shifts; and, lanes marked R show MI eluted from the column during regeneration.

The invention thus encompasses a cleavage-based purification and products used therein and products therefrom such as: (i) A non-naturally occurring tripart protein with a controllable intervening sequence (IS), e.g., an intein, such as a modified intein, or a mutant intein, or a truncated and mutated intein screened/selected and/or an intein according to the invention, releasing the desired protein (DP), e.g., into solution. The IS advantageously can be located before a serine, threonine or cysteine residue of the DP or at the 3' end of the IS. (ii) A method for producing a modified protein, e.g., at the DNA level through DNA fusion (expressing a nucleic acid such as DNA encoding a fusion protein, e.g., a tripart protein; this translated fusion protein can contain a controllable IS for cleavage, e.g., with properties as in (i)). (iii) A method of producing a desired protein, e.g., at the DNA level through DNA fusion (expressing a nucleic acid such as DNA encoding a fusion protein, e.g., this translated fusion protein can contain a controllable IS for cleavage, for instance, with properties as in (i); the fusion protein can comprise a polypeptide having an amino acid sequence corresponding to that of the desired protein but additionally including the intein, e.g., wherein the intein is positioned at a specific region of the desired protein, wherein the capability of fast enzymatic cleavage under predetermined conditions (e.g., pH, temperature, salt, and the like, and combinations thereof) is employed to obtain the desired protein from the polypeptide. (iv) A method of producing a protein through assembly of separate components at the protein level wherein the protein contains a controllable IS for cleavage, such as an inventive intein (for instance, subjecting a fusion protein of any of the foregoing to conditions wherein the intein has cleavage).

The invention thus further encompasses a selection system for the creation of controllable cleavage proteins products used therein and products therefrom such as: (i) An intein in external fusion to the N-terminus of a reporter enzyme such as TS, for example, wherein the intein and reporter (e.g., TS) are separated by a cysteine, serine or threonine residue. (ii) An intein in external fusion to the N-terminus of the reporter (e.g., TS) enzyme; for instance, wherein the C-terminal asparagine or histidine or histidine-asparagine of the intein is immediately followed by, the initial methionine of the reporter (e.g., TS). It is believed that in an NEB commercial system the histidine is removed and/or not present, and the inventors have found that pH sensitivity is affected by that histidine. (iii) An intein in an external fusion to the N-terminus of the reporter (e.g., TS) enzyme; for instance where the initial methionine of the reporter (e.g., TS) has been eliminated so as to prevent polycistronic translation during screening. (iv) An intein in external fusion to the N-terminus of the reporter (e.g., TS) enzyme where the C-terminal histidine of the intein is immediately followed by the second amino acid of the reporter (e.g., TS), such as lysine. This can be used to screen for inteins that are capable of rapid splicing in the absence of conserved amino acid residues, such as cysteine, serine and/or threonine. (v) A method for creating the fusions described herein through DNA fusion using intein DNA. (vi) A method for creating the fusions using DNA through DNA fusion using intein DNA wherein the intein DNA is mutated intein DNA. (vii) A method of amplifying intein DNA to introduce random mutations using a polymerase such as Taq. (viii) A method for screening for elevated intein cleavage activity using growth medium and varying conditions (physical such as temperature and/or chemical such as pH and/or ion concentration/presence/absence) (e.g., -THY medium, and temperature elevation and/or pH screening as herein discussed). (ix) A method for screening for reduced intein cleavage activity using a drug which plays a part in a cell metabolic and/or biochemical cycle (e.g., trimethoprim gradient; folic acid cycle). (x) A method to incorporate deleted inteins into the screen using DNA fusion: for example, inteins in an internal fusion to the reporter (e.g., TS) enzyme, interrupting it at points such as points that precede or immediately precede a conserve such as serine, cysteine or threonine, and then testing for elevated and/or reduced cleavage activity.

The methods for selecting for elevated and reduced activity can be used to screen and/or select for high activity mini-inteins. Further, the invention encompasses a method for generating mutated DNA for the mini-inteins; mini-inteins are advantageously used in other aspects of the invention, such as in screens, fusions and the like. Intein embodiments of the invention can have more than one mutation; e.g., a first mutation for self-cleaving characteristics (e.g., enhancement thereof) and a second mutation for splicing characteristics (e.g., for facilitating and/or enhancing splicing); and, in this way, inteins or mini-inteins of the invention can have surprisingly superior activity in comparison to other inteins. Also, such inteins are advantageously controllable by varying a condition.

These and other embodiments and utilities are disclosed in, enabled by and are obvious from and encompassed by the invention. For instance, while the disclosure has mentioned compounds that cleave and/or cleave and splice in terms of "inteins" (such as in embodiments including linking the "intein" with a reporter or desired polypeptide portion and/or a binding protein portion), the invention is not necessarily limited to inteins. It is contemplated that other elements or moieties which have cleaving and/or cleaving and splicing activity can be used in the practice of the invention, e.g., as the IS; for instance, hedgehog proteins. See, e.g., FIG. 2 and Beachy et al. (1997) Cold Spring Harbor Symposium of Quantitative Biology Vol. 62, pp. 191–204. The 2A protein of the *cardiovirus* encephalomyocarditis virus can also be used. Jackson (1986) Virol. 149:114–127. The 2A region of the foot-and-mouth disease virus (FMDV) including the 19 amino acid sequence spanning FMDV 2A (LLNFDLLKLAGDVESNPGP—SEQ ID NO:8) is also suitable for use herein. See, e.g., Ryan et al. (1991) J. Gen. Virol. 72:2727–2732; Ryan et al. (1994) EMBO J. 13:928–933; and Hahn et al. (1996) J. Virol. 6870–6875.

The invention provides inteins that display a strong dependence on temperature, allowing uncleaved precursor to be expressed in host cells for purification. Although this requires that protein be expressed at low temperatures, nearly total precursor can be generated with almost no cleavage. This is a capability that has not been demonstrated to work adequately in the past as premature cleavage results. In the present invention, the isolated C-terminal cleavage reaction can be completed (about 90–95%) in about 4 hours at 37° C., in about 12 hours at 25° C., in about 30 hours at 20° C. or in about 150 hours at 4 C. This cleavage rate compares to that achieved with traditional protease steps in conventional protein fusion purifications (95% cleavage after 6 to 8 hours at 23° C., other temperatures can not be used due to loss of protease activity).

Amitai and Pietokovski (1999) describe the advantages of the claimed invention as "an elegant mutational strategy to engineer an intein with improved features to serve as a tool for protein purification. They further state that, the "use of a genetic selection strategy can refine the activities of engineered proteins to an extent not currently possible with rational design."

The invention shall be further described by way of the following Examples and Results, provided for illustration and not to be considered a limitation of the invention.

EXAMPLE 1

Genetic System Yielding Self-Cleaving Inteins and Protein Purification with Same Experimental Protocol Plasmid construction. Plasmid pK is pKK223-3 (Pharmacia) (Table 1). Plasmid pKT consists of the bacteriophage T4 td gene inserted into pK, while pKT::I contains the Mtu intein inserted N-terminal to Cys-238 such that TS sequence is restored by intein splicing. Derbyshire et al. (1997a). For cleavage selection, the intein and id genes were amplified separately by PCR and joined by overlap extension (SOEing) (Horton et al. (1990) BioTech. 8:528–536) to form IT fusion DNA with the external primers encoding the C1A mutation. This DNA was then cloned into pMal-c2 (New England Biolabs) to form pMIT. In both cases, inactive control inteins (superscript AA) were formed by replacing the conserved C-terminal His—Asn with Ala—Ala via PCR. The M$\Delta$I$^\dagger$C fusion was generated by replacing the id gene (T) in M$\Delta$I$^\dagger$T with C-I-TevI(C).

Generation and selection of mutant inteins. Inteins were amplified using error-prone Taq polymerase for 35 cycles of PCR with primers encoding the conserved residues of each splice junction. Pools of mutagenized inteins were cloned directly into either the pKT or pMI$^\dagger$T context, transformed into D1210$\Delta$thyA and selected on thymineless medium at 37° C.

Determination of in vitro cleavage kinetics. Expression of precursor protein was induced at mid-log phase in rich medium (2% tryptone, 1% yeast extract, 1% NaCl) (w/v). Purification was performed by the maltose affinity separation protocol (New England Biolabs) with a modified column buffer (20 mM Tris HCl pH 8.5, 500 mM NaCl, 5% glycerol, 2 mM EDTA, 1 mM DTT). Purified precursor was diluted 5:1 into pH-adjusted cleavage buffers (100 mM Tris HCl or PIPES at desired pH, 500 mM NaCl, 5% glycerol, 2 mM EDTA, 1 mM DTT) and incubated at the desired temperature. Samples were separated on SDS PAGE and stained with Coomassie Blue for quantification of cleavage products by scanning densitometry.

C-I-TevI purification. Precursor was overexpressed and bound to amylose resin as above. Following the column wash, the column pH was adjusted to 6.0 by rapid introduction of one column volume of pH 6.0 column buffer (20 mM PIPES pH 6.0, 500 mM NaCl, 5% glycerol, 2 mM EDTA, 1 mM DTT). The column flow was then stopped and the column was held at 4° C. for 17 hr. Product was collected in one additional column volume of pH 6 column buffer. Column regeneration and collection of cleaved M$\Delta$I$^\dagger$ was accomplished as directed (New England Biolabs).

Results

Selection of mini-intein mutants with enhanced splicing and cleavage activities. Intein fusions with the enzyme thymidylate synthase (TS) provide a means to monitor and modulate intein function through genetic selection in the absence of thymine. Derbyshire et al. (1997a); Belfort et al. (1994); and Belfort et al. (1984). E. coli deficient in cellular TS, and containing plasmid vector alone (pK, see Table 1 for plasmid nomenclature) is unable to grow without thymine (TS—), but if the plasmid encodes a TS gene (pKT), growth occurs (TS+) (FIG. 1A, constructs 1 and 2). To link intein splicing activity to the TS reporter system, intein-TS fusions were constructed with the td gene of phage T4 so that active TS would be produced only as a result of splicing (FIG. 1A). Derbyshire (1997b).

As expected, internal fusions with the active, full-length M. tuberculosis (Mtu) recA intein (Davis et al. (1992) Cell 71:201–210) (pKT::I) were TS+(FIG. 1A, construct 3), while fusions with an inactive control intein (pKT::I$^{AA}$) were TS— (FIG. 1A, construct 4). For mutagenesis and selection studies, a mini-intein ($\Delta$I) was chosen, comprising the first 110 and the last 58 amino acids of the 441 amino acid Mtu recA intein. Fusions with the $\Delta$I intein were TS$^+$(pKT::$\Delta$I) only at low temperature, indicating low levels of splicing (FIG. 1A, construct 5). Derbyshire et al. (1997a). Selection at elevated temperature therefore provides a method for isolating highly active mini-intein mutants. To this end, a pool of mini-inteins generated by mutagenic PCR was inserted into pKT for selection at 37° C. One of the candidate splicing mutants that promoted growth on selective medium at 37° C., pKT::$\Delta$I-SM (FIG. 1A, construct 6), was sequenced and found to contain a conservative replacement of Val-67 with Leu (V67L).

Because C-terminal cleavage is possible without splicing, it was hypothesized that cleavage could be uncoupled from splicing and enhanced through mutagenesis and selection. Thymidylate synthase in N-terminal fusion is inactive, probably because dimerization is prevented. Therefore, a plasmid expressing a tripartite fusion (pMIT), comprising a maltose binding domain (M), the full length Mtu intein (I), and TS (T) was constructed. An added Cys residue separates the intein and TS, while an intein Cys-1 to Ala mutation (C1A) was introduced (pMI$_+$T) to suppress N-terminal cleavage and extein ligation (FIG. 1B). This fusion is TS+only at low temperatures, indicating rudimentary C-terminal cleavage (FIG. 1B, construct 1), while fusion with an inactive control intein (pMI$^{\dagger-AA}$T) was TS$^-$at all temperatures (FIG. 1B, construct 2).

The $\Delta$I intein in this context was unable to promote appreciable growth at 20° C., implying lower cleavage activity than the full-length intein (FIG. 1B, compare constructs 1 and 3), while the $\Delta$I-SM mutant behaved similarly to the full-length intein (FIG. 1B, compare constructs 1 and 4). A second mini-intein mutant, $\Delta$I-CM, which promotes growth at 37° C. in this context (FIG. 1B, construct 5), was isolated and shown to possess three mutations; the V67L substitution observed independently in the $\Delta$I-SM mutant, as well as two Asp to Gly mutations, D24G and D422G (residues numbered relative to full-length Mtu intein).

Cleavage activity in vivo. Overexpression at 20° C. resulted in accumulation of tripartite precursor for the wild-type intein as well as $\Delta$I, $\Delta$I-SM and $\Delta$I-CM in the MI$^\dagger$T context. Incubation at elevated temperature resulted in disappearance of precursor and appearance of cleavage products on polyacrylamide gels (see for example FIG. 3C). Unlike the other mutants, disappearance of the $\Delta$I mini-intein precursor did not yield significant cleavage products during incubation at 37° C., consistent with instability of this intein. The $\Delta$L-SM mutant behaved similarly to the full-length intein, cleaving to completion in 16 to 30 h (FIG. 3A, left). Strikingly, the $\Delta$I-CM mutant cleaved to completion within 5 h, exhibiting significantly faster cleavage than any of the other inteins (FIG. 3A, right).

pH-sensitive cleavage of mini-intein mutants facilitates protein purification. Two contexts were used to monitor C-terminal cleavage in vitro: pMI$^\dagger$T and pMI$^\dagger$C, which has TS of pMI†T replaced with the C-terminal domain of endonuclease I-TevI (C-I-TevI). Derbyshire et al. (1997b). In both cases, significant precursor accumulated with all inteins through overexpression at 20° C., with the maltose binding domain providing the route to rapid purification of the precursor. Cleavage was more rapid in the MI†C context for all the inteins, although the relative cleavage rate of each paralleled that observed in vivo in the pMI†T context. An additional characteristic shared by the inteins was a strong pH sensitivity (FIG. 3B). In all cases, cleavage rates increased as the pH was reduced, typically increasing by a factor of 8 or more in the pMI†C context as the pH was decreased from 8.0 to 6.0. The strongest pH activation was exhibited by the ΔI-CM mutant, for which the cleavage rate increased by a factor of more than 20 in this pH range. The cleavage inhibition at high pH was reversible in all cases, allowing tripartite precursor to be stored for several days at 4° C. and pH 8.5 without significant cleavage or loss of activity.

The pH-sensitivity of the ΔI-CM intein was used to facilitate purification of C-I-TevI (FIG. 3C). Expression of tripartite precursor (MΔI†C-CM) was induced for 2 h at 20° C. to accumulate uncleaved precursor (FIG. 3C, lane 1), which was then bound to amylose resin via the maltose binding domain at pH 8.5 (FIG. 3C, lane 2). The column pH was shifted by the introduction of pH 6 buffer, and following cleavage at 4° C., C-I-TevI was collected with detectable amounts of the other cleavage product (FIG. 3C, lanes 3–14).

TABLE 1

Plasmids used.

| Plasmid | Description and Reference |
|---|---|
| pK | pKK223-3 vector. Derbyshire et al. (1997a) |
| pKT | Intronless td gene in EcoRI-XbaI sites of pKK223-3 |
| pKT::I | pKT with full-length intein upstream of td Cys238. Derbyshire et al. (1997a) |
| pKT::I$^{AA}$ | pKT::I with inactivated intein (final His-Asn replaced with Ala-Ala). Derbyshire et al. (1997a) |
| pKT::ΔI$^a$ | pKT with the mini-intein (ΔI) upstream of td Cys238. Derbyshire et al. (1997a) |
| pKT::ΔI-SM | pKT::ΔI with SM splicing mutation$^b$ |
| pMIT | Tripartite fusion: Maltose binding domain + full-length intein + TS. Derbyshire et al. (1997a) |
| pMI†T$^c$ | pMIT with initial Cys of intein mutated to Ala (allows only cleavage)$^b$ |
| pMI†-AAT | pMI†T with inactivated intein$^c$ |
| pMΔI†T | pMI†T with ΔI in place of full-length intein$^c$ |
| pMΔI†T-SM | pMΔI†T with SM splicing mutation$^b$ |
| pMΔI†T-CM | pMΔI†T with CM cleaving mutations$^b$ |
| pMI†C | pMI†T with TS replaced by C-I-TevI$^b$ |

$^a$Δ = mini-intein.
$^b$This work.
$^c$† = C1A mutation.

EXAMPLE 2

Purification of Toxic Proteins by Inactivation with Inteins in Specific Regions and pH-Controllable Intein Splicing The fusion gene I-TevI::SM::CBD with the intein N-terminal to Cys164 was cloned into pET28a (Novagen), an expression vector with a strong T7 promoter. A non-spliceable control, I-TevI::SM$^{AA}$, in which the His-Asn dipeptide at the C-terminus of the SM mini-intein was mutated to Ala—Ala, was also cloned into pET28a to test the toxicity of the unspliced precursor. When the plasmids were transformed into BL21 (DE3), an E. coli strain for expression of genes with T7 promoters (Studier et al. (1990), Met. Enzymol. 185:60–89) there were no transformants for pET28-I-TevI::SM::CBD but many transformants for pET28-I-TevI::SM$^{AA}$. Restored toxicity suggested leaky expression of I-TevI. To reduce the leaky expression of 1-TevI::SM::CBD, the strain BL21 (DE3)pLysS was used, which has more stringent control over T7 polymerase by inhibiting its activity with T7 lysozyme expressed from the pLysS plasmid. When the pET28-I-TevI::SM::CBD plasmid was transformed into BL21(DE3)pLysS, many transformants with the correct wild-type sequence were obtained.

These results indicate that I-TevI toxicity has been suppressed to a tolerable level by intein inactivation. Similar constructs at different specific regions in the I-TevI sequence gave varying degrees of relief from toxicity (FIG. 5). Insertions in the N-terminal domain preceding Cys39, Cys 58 and Cys1000 resulted in lowest cell viability. Insertions preceding Cys153 and Cys164 which constitute a zinc finger at the joining segment/C-terminal domain interface resulted in highest cell viability. Insertions preceding Cys214 and Cys207(helix-turn-helix region) were intermediate in their effect on cell viability.

A schematic representation of the intein-based I-TevI purification protocol is shown in FIG. 19. The expression (transcription and translation) of the innocuous unspliced precursor was induced with 1 mM IPTG at 20° C. for 2 hours from a starting OD of 0.4. The cell pellet was sonicated and the cleared lysate was loaded onto a chitin column in pH 8.5 column buffer (20 mM Tris-HCl, 500 mM NaCl, 0.1 mM EDTA, 0.1% TritonX-100). The chitin column was then washed with 10 bed volumes of pH 8.5 column buffer to remove all contaminants. Then the column pH was rapidly shifted to pH 7.7 to induce on-column splicing. The product proteins were eluted after 26 hours of reaction at 4° C. The spliced product was released from the column as a result of the splicing reaction, while the intein-binding domain fusion remained attached. The spliced active product was collected at the column outlet, at the end of the splicing reaction. The invention thus provides a rapid, single step purification of proteins.

FIG. 20A shows the result of a typical I-TevI purification conducted according to the protocol illustrated in FIG. 19. Lanes 6–16 show the purified full-length wild-type I-TevI and the two distinct domains, which are by-products generated by cleavage at both ends of the intein without ligation. Cleavage assays were conducted on the purified fractions (FIG. 20B), in which the substrate DNA was cleaved efficiently. This demonstrates that the cleavage activity of I-TevI has been restored after pH-induced splicing of the fusion precursor. Furthermore, DNA sequencing of the expression plasmid taken from cells after induction indicated that the I-TevI sequence was wild-type. These results show the efficacy of producing wild-type toxic proteins via inactivation with an intein in a specific region followed by pH-induced splicing.

EXAMPLE 3

Trimethoprim to Select for Inteins with Reduced Activity to Generate Controllable Intein Mutants In the presence of trimethoprim and thymine, the effect on growth phenotype of liberated thymidylate synthase is reversed, leading to a loss of cell viability as a result of intein activity. This aspect of the screen has been used to generate full-length Mtu intein mutants with compromised activity at 37° C.

Figure 6:
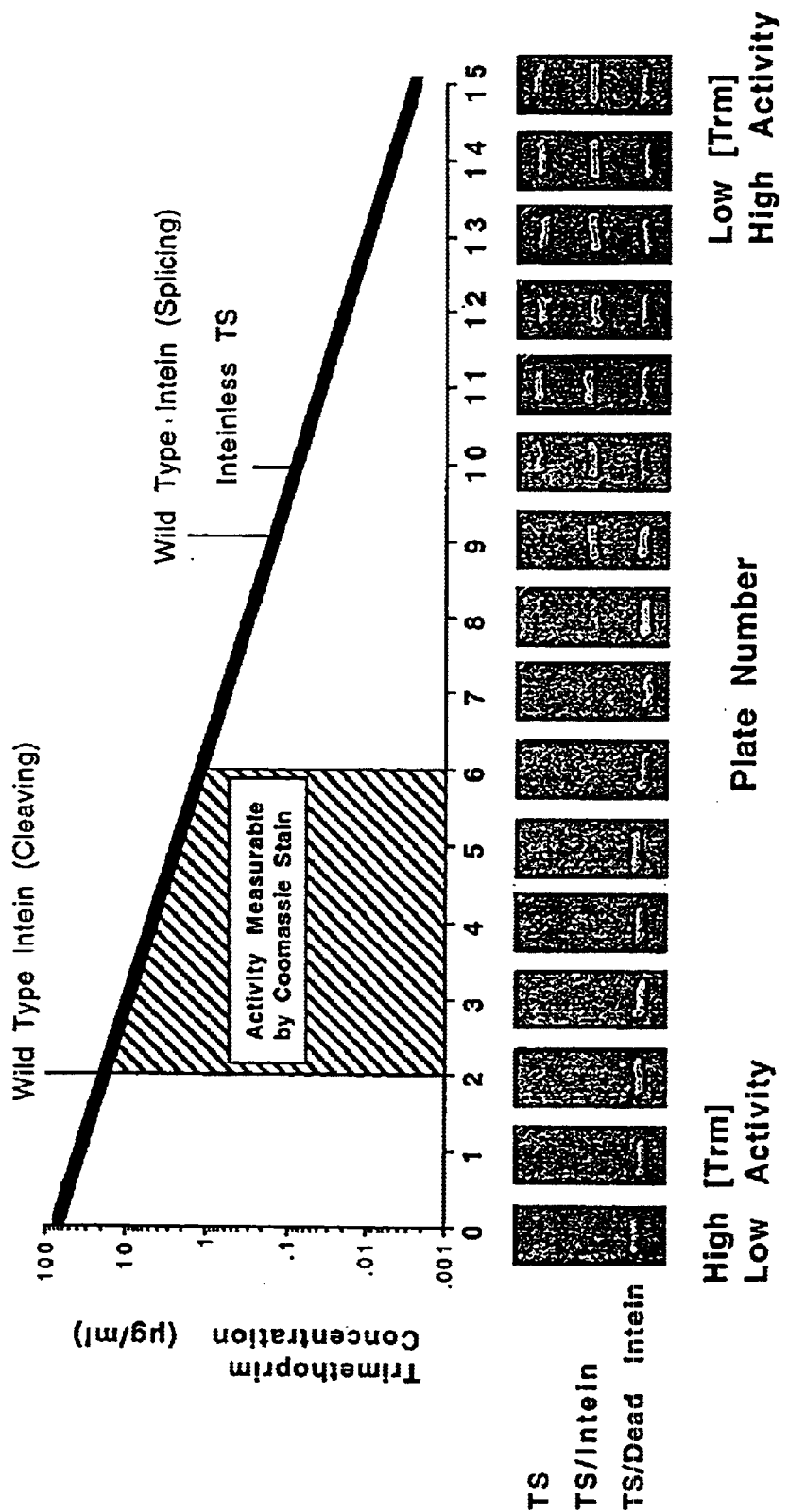
FIG. 6 shows trimethoprim Gradient Assay. A series of plates (1–15) is used to determine the critical trimethoprim (Trm) concentration required to suspend growth of patched clones. Higher TS activities, indicative of higher intein activities, are more sensitive to trimethoprim, resulting in suspended growth at lower concentrations (colonies stop growing further to the right. Clones: TS, uninterrupted thymidylate synthase (highest activity)); TS/intein, thymidylate synthase interrupted by the full length intein (lower activity due to intein insertion); TS/dead intein, TS inactivated by intein insertion (no intein activity).

The use of trimethoprim can further be refined to provide a screen for evaluating variations in intein activity at different temperatures (see FIG. 6). As the activity of the intein and resulting thymidylate synthase increase, so does the cell sensitivity to trimethoprim. A series of agar plates, each containing a different concentration of trimethoprim is used to indicate variations in intein activity based on the drug sensitivity. This screen has been used to indicate relative activities of a number of intein mutants. This screen can also be used to gradually increase selective pressure over several rounds of mutagenesis. Finally, this screen also has the advantage that it can be used at various temperatures, allowing evaluation of intein activity independent of temperature effects on intein activity.

With reference to FIG. 6, a series of plates, numbered 0 to 15 is used to determine the critical trimethoprim (Trm) concentration required to suspend growth of patched clones. Higher TS activities, indicative of higher intein activities, are more sensitive to Trm, resulting in suspended growth at lower concentrations (colonies stop growing further to right). Clones: TS, uninterrupted thymidylate synthase (highest activity); TS/Intein, Thymidylate synthase interrupted by the full length intein (lower activity due to intein insertion); TS/Dead Intein, Ts inactivated by intein insertion (no intein activity).

EXAMPLE 4

Maltose Binding Domain-Intein Fusion

To demonstrate efficacy and versatility of the mini-intein in affinity separations, we have created a maltose binding domain-intein (MI) DNA fusion, which has in turn been joined at its 3' end to the coding sequences of a number of potential product proteins (X). The expression level and solubility of the resulting tripartite precursor proteins (MI:X) were measured, and test purifications were performed on recombinant human acidic fibroblast growth factor (aFGF; Volkin et al. (1996) Pharma Biotech. 9:181–217) using batch and flow purification strategies. For both strategies, low temperature induction allowed a buildup of uncleaved precursor (MI:aFGF) during overexpression, while high pH inhibited premature cleavage during lysis and purification. Cleavage was induced on-column with a shift to low pH in either a batch reaction without flow, or in flow mode to concentrate the purified product (FIG. 10A).

A simple model has been developed to predict the effects of critical operating parameters for process optimization, and numerical simulations have been performed to verify the model. See Example 5. Finally, the accuracy of the cleavage reaction and activity of the protein have been verified. This single-step purification of active aFGF shows that inteins can be used to simplify affinity-fusion based protein separations, thus making this technique an attractive alternative to conventional purification schemes.

Protein Overexpression

The general MI:X plasmid was constructed using the commercially available maltose binding domain fusion vector pMal-c2 (New England Biolabs, Beverly, Mass.). In previous work, the intein was fused to thymidylate synthase (TS) and the fusion was inserted as a cassette between the EcoRI and XbaI sites of the pMal polylinker to form pMI:TS. Derbyshire et al., (1997b). The design was such that a silent BsrG I site was generated at the end of the intein to separate the intein and TS sequences. In work described above, native splicing of the intein was suppressed by mutating the initial Cys residue of the intein to Ala. Wood et al. (1999). In this Example, other DNA sequences have been inserted as cassettes, replacing the TS sequence between the BsrG I and Xba I and Hind III sites to form different precursor proteins. For expression, these precursor-encoding plasmids were transformed into E. Coli strain ER2566 (New England Biolabs) and grown to mid-log phase in 200 ml rich medium (2% tryptone, 1% yeast extract, 1% NaCl, W/V). Precursor was expressed by addition of 1 mM IPTG at 20° C. for 4 hrs. Cells were harvested by centrifugation, resuspended in 10 ml pH 8.5 column buffer (20 mM AMPD, 20 mM PIPES, 200 mM NaCl, 1 mM DTT) and stored at −80° C.

Protein Purification

Cells were lysed by sonication in pH 8.5 column buffer, the lysate was then clarified by centrifugation and diluted into 50 ml pH 8.5 column buffer. Diluted lysate was loaded onto 30 ml (bed volume) of amylose resin (New England Biolabs) in a XK16 column (Amersham Pharmacia Biotech) and washed with 3 to 10 column volumes pH 8.5 column buffer. Lysis, clarification, precursor binding and column wash were carried out at 4° C. For off-column cleavage studies, purified precursor protein was recovered by the addition of pH 8.5 column buffer with 10 mM maltose. For on-column cleavage studies in batch and flow modes, the precursor protein remained bound, while the column temperature was controlled using a column jacket and circulating water bath. For on-column cleavage in batch mode, 2 bed volumes of pH 6.0 column buffer were pumped rapidly through the column, and flow was stopped for sufficient time to allow cleavage at the desired temperature. Following cleavage, released product protein was collected in one additional column volume of pH 6.0 column buffer. For on-column cleavage in flow mode, the column temperature, buffer pH and flow rate were simultaneously adjusted to induce the desired combination of cleavage rate and column residence time. In all cases, cleaved MI and uncleaved precursor were recovered prior to column regeneration through the addition of 10 mM maltose to displace the bound species.

Purification of aFGF

Figure 21:
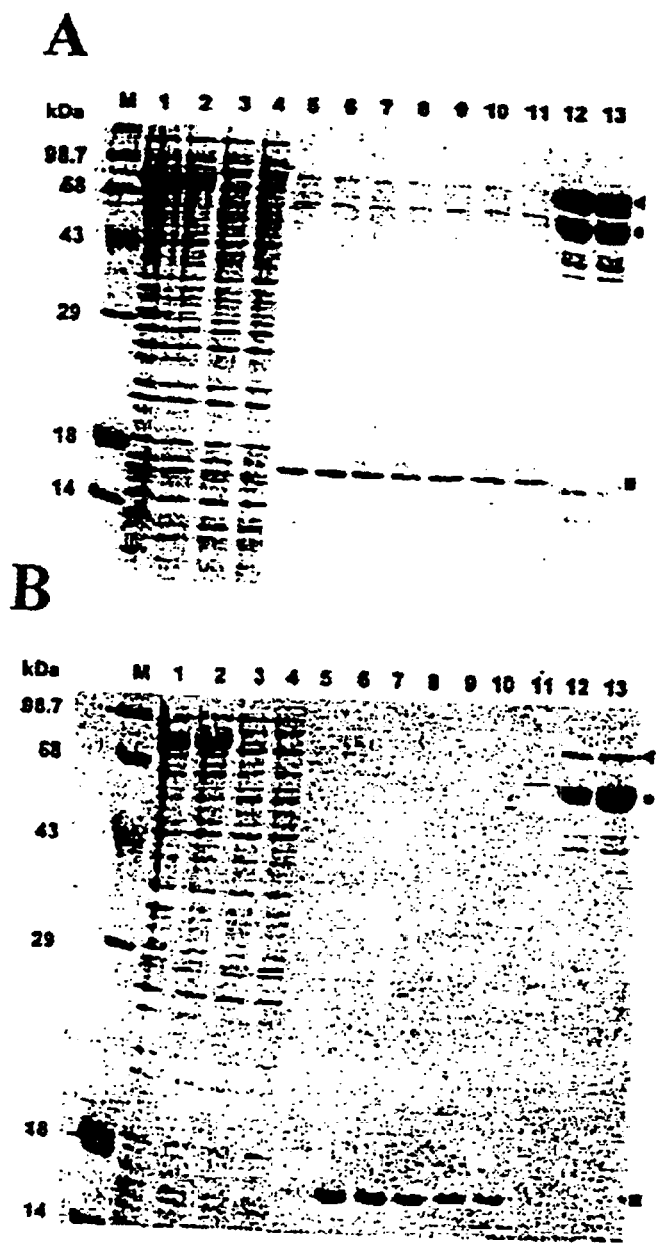
FIG. 21 shows purifications of native aFGF using the intein fusion system. (A) SDS-PAGE gels of batch mode cleavage as described in text. Lanes: M=molecular weight markers; 1=total cell lysate; 2=soluble fraction of cell lysate; 3 and 4=column flowthrough of unbound material; 5–11= purified product protein fractions; 12–13=precursor and cleaved binding domain recovered during column regeneration; ▲=precursor protein; ●=cleaved binding domain; and ■=aFGF protein. (B) Flow mode purification as described in text. Lanes and cleavage products are as in (A).

Cell containing native MI:aFGF precursor protein were harvested at pH 8.5 and 4° C., lysed and clarified by centrifugation. The supernatant was then passed over a 30 ml (bed volume) amylose resin column to allow binding of the uncleaved precursor (FIG. 21A, lanes 1 and 2). The unbound protein was washed out of the column with 10 column bed volumes of pH 8.5 running buffer (FIG. 21A, lanes 3 and 4). For batch cleavage purification, the pH of the column was changed rapidly to pH 6.0 by the introduction of two bed volumes of low pH buffer at a column flow rate of 2.0 ml/min. The column was then sealed for cleavage at 4° C. for 30 hr. Following incubation, the cleaved aFGF protein was collected in approximately one void volume (26 ml) of pH 6.0 buffer (FIG. 21A, lanes 5–11). The cleaved binding domain and remaining uncleaved precursor were then recovered by the addition of buffer containing 10 mM maltose (FIG. 21A, lanes 12 and 13). The material recovered during column regeneration confirmed that the cleavage reaction had proceeded about half-way to completion, in agreement with the calculated MI:aFGF cleavage half-life of approximately 35 hr. At 4° C., approximately 175 hr were required for 97% product protein recovery.

For cleavage in flow mode, the precursor protein was bound and washed as before at a flow rate of 1 ml/min and a temperature of 4° C. (FIG. 21B, lanes 1–4). Following the column wash, the flow rate was slowed to 0.1 ml/min, and the temperature of the column was elevated to 37° C. by circulation of heating water in the column jacket. This combination of temperature and flow was designed to provide significant concentration of the product protein as predicted by the flow mode model. The low flow rate also insured that the column temperature would be uniform during the cleavage reaction. As predicted by the model, the product protein was collected in a relatively small volume (approximately 8 ml) as a pure species (FIG. 21B, lanes 5–11). The peak also exhibited the predicted exponential decay shape, with most of the product protein being concentrated in the first few milliliters of the peak. In this case, analysis of the cleaved binding domain indicated that the cleavage reaction had gone essentially to completion, with more than 97% of the product protein recovered in ca. 12 hr. (FIG. 21B, lanes 12 and 13). Mitogenicity assays of the aFGF products recovered at 4° C. and 37° C. were performed against an internal control which was purified by a conventional method. The EC50 values for the 4° C. and 37° C. cleavage products were 146 and 578 pg aFGF/ml respectively. These values compared well with those of the internal control which usually range from 150 to 500 pg aFGF/ml.

Determination of aFGF Activity

Uptake of labeled thymidine by aFGF-stimulated cells allowed a determination of the potency of the purified protein. Balb/c 3T3 mouse fibroblast cells were plated in a 96 well format in Amersham Pharmacia Biotech's Cytostar T™ Scintillating Microplate. Because a solid-phase scintillant is embedded in the bottom of each well, a signal will be generated only when radiolabel is brought in close proximity to the bottom of the well, such as by cellular uptake. After attachment to the plate, cells were kept in growth arrest media for two days to allow cells to synchronize, and were then treated with aFGF solutions at varying concentrations. After an overnight treatment with aFGF, cells were labeled with [$^{14}$C-methyl] thymidine for one day and then counted in a Wallace MicroBeta™ scintillation counter.

Data were transferred into SigmaPlot® and CPMs vs. aFGF concentration were plotted. A sigmoidal 4-parameter fit was used to estimate the equation of the curve and the $EC_{50}$ for each sample was calculated. The $EC_{50}$ for each sample was calculated. The $EC_{50}$ is an estimation of the effective concentration of aFGF that gives 50% of maximal growth stimulation as measured by radiolabeled thymidine uptake.

EXAMPLE 5

Data Acquisition for Modeling

For determination of cleavage rate constant vs. pH, the pH of the purified precursor was adjusted by HCl addition and timecourses were run at various temperatures. Cleaved products were separated on Coomassie stained SDS-PAGE, and quantified by scanning densitometry. Cleavage was modeled as a first order decay reaction with rate constants calculated at each timepoint, pH and temperature. Dispersive behavior of the column was determined using pH as a non-interacting tracer at various buffer flow rates. For model comparison to real purification data, column fractions were separated on Coomassie stained PAGE and quantified by scanning densitometry as before. The density of each fraction was used as the concentration of the purified product protein.

Modeling

Cleavage Reaction

The intein cleavage reaction was modelled as an irreversible first order decay of the form $$MI{:}X \xrightarrow{k} MI + X \qquad (1)$$

where bound MI:X cleaves with rate constant k to form bound MI and released product (X). Batch operating mode is represented as the trivial case where the pH of the column is changed rapidly, and the column is sealed and incubated for sufficient time to complete the cleavage reaction at the pH and temperature of the stagnant column. The released product protein is recovered in a single column fluid volume at a concentration essentially equivalent to that of the initial bound precursor.

If the intein cleavage rate is sufficiently rapid, the concentration of the released product protein can be increased by allowing cleavage to take place at the pH front as it moves slowly through the column (flow mode). For purposes of predicting column behavior for this strategy, the column is divided into N stacked stationary elements with differential pore volume $\Delta V$ and a uniform initial bound precursor concentration of $[MI{:}X]_0$. The mobile phase is described as a series of elements of differential volume $\Delta V$, each with an associated pH. In the discrete model, the fluid in each mobile volume element undergoes a short batch cleavage reaction while in contact with each stationary volume element as it moves through the column. The pH and resulting rate constant of each reaction is determined by the pH of each mobile volume element, which is dictated by the shape of the pH front traveling through the column. The concentration of bound precursor in each batch reaction of $\Delta V$ can be described by $$[MI{:}X]_{t+\Delta t}=[MI{:}X]_t exp(-k\Delta t) \qquad (2)$$

where is k is a function of pH and temperature. The value $\Delta t$ is the residence time of each mobile volume element in each stationary element, calculated by dividing $\Delta V$ by the column flow rate. A simple mass balance then yields $$[X]_{\Delta t}=[MI{:}X]_t\{1-exp(-k\Delta t)\} \qquad (3)$$

for the concentration of product protein released into the differential fluid element in time $\Delta t$.

In the mode of operation, the product protein released in each time step can be increased by slowing the rate of the pH front moving through the column or by increasing the temperature of the column, effectively increasing $\Delta t$ or k, respectively, in equation (3). If the cleavage reaction goes essentially to completion in a relatively small volume immediately following the pH front, the product can be collected as a concentrated peak. The shape of the peak can easily be predicted for the ideal nondispersive case by summing the total product released into each mobile volume element over the series of batch reactions it undergoes as it moves through the column.

A critical aspect of this model is that pore diffusion of buffer components and product protein in the affinity resin is assumed to be very rapid relative to the overall process and can therefore be ignored. This assumption can be evaluated by calculating the associated Damköhler number ($D_a$),

$$D_a = \frac{kC^{n-1}_{MI{:}X}L^2}{D_x} \qquad (4)$$

that describes the ratio of reaction velocity to diffusive velocity. In this case, k is the cleavage rate constant at optimal pH (0.02 to 1.0 hr$^{-1}$ depending on temperature), $C_{MI{:}X}$ is the concentration of bound precursor (approximately 10$^{-4}$ M), n is the order of the reaction (1 for first order decay), L is the diameter of the resin beads (approximately 10$^{-4}$) and Dx is the diffusion coefficient of the cleaved product protein (1.8×10$^{-7}$ to 4.6×10$^{-7}$ m²/hr for various proteins, Cussler (1984) Cambridge University Press,). Although the Damköhler number for this system varies somewhat with temperature and product protein identity, it is typically less than 0.05, and thus below the region where diffusion is significant. Deen (1998) Oxford University Press. Elimination of pore diffusion from the model is further supported by comparisons between diffusive rates and long column residence times that are required for reasonable product concentration.

EXAMPLE 6

Model Behavior

For the ideal case with a perfectly flat pH front, no column dispersion and no entrance or exit effects, an analytical solution for the shape of the product peak at the column outlet is possible (FIG. 22A). In this case, a rate constant of zero is assumed for the nonpermissive (high) pH, while the permissive (low) pH following the front is adjusted to give the maximum rate constant. The height of the peak is the cleavage rate constant multiplied by the column residence time and total column capacity. All three of these factors can be adjusted during process design and optimization. The cleavage rate constant can be controlled by both pH and temperature within the limits dictated by the intein and product protein. The column residence time is a function of the total column volume and volumetric flow rate, and the total column capacity is a function of the affinity resin and column volume. An important prediction of this model is that column geometry and the related theoretical plate height have no effect on peak size or shape, allowing great flexibility in process design. The cleavage rates were found to be much faster with a N-terminal cysteine than without. These results are shown in Table 2.

For a more realistic system in which the pH front is not ideal (flat), a few notable results are observed (FIG. 22B). In this simulation, the non-ideality of the pH front is assumed to arise from mixing in the pump and tubing as well as a non-ideal flow distribution at the column inlet. Experiments to evaluate dispersion in the absence of a column and with columns of different geometries indicated that the majority of the dispersion arises from flow distribution inequalities at the column inlet and outlet and increases with increasing column radius. Typically, the front would be dispersed over several centimeters of column length for a 16 mm I.D. column, and depends strongly of the diameter of the column used. Furthermore, the shape of the front is assumed to be constant as it moves through the column, exhibiting no additional rate-dependant axial dispersion in the column. This assumption is supported by the low axial diffusion of the mobile phase species and relatively broad front delivered by our experimental system, and has been verified experimentally using non-interacting tracers. The direct effect of a dispersed pH front is relatively broad zone within the column where cleavage rates are intermediate (FIG. 22B) rate constant for high dispersion case), resulting in a broadening of the product peak with a reduction in peak height. However, the time and volume needed to obtain total product recovery is very similar, regardless of the front dispersion (FIG. 22B, high dispersion).

EXAMPLE 7

Results Obtained in Examples 4–6 and Discussion Thereof

To investigate the effect of fusions with different product proteins on precursor expression level and solubility, two test proteins (aFGF and TS) were cloned into the system and overexpressed in a variety of host cells (FIG. 23A). Initial work was carried out with a cysteine residue added to the beginning of each product protein to mimic the native C-terminal splice junction. In each case, the precursor protein was fully soluble and well expressed in the E. coli strain ER2566, as is typical of maltose binding domain fusions. Kapust et al. (1999) Prot. Sci. 8:1668–1694. The level of expression was typically about 5% of the total cellular protein under optimal conditions. However, premature cleavage in vivo during induction often led to losses of uncleaved material (FIG. 23A, right side with cysteine). These losses were reduced by the elimination of the added cysteine residue, which decreased the cleavage rate by a factor of ~10 while at the same time providing a native methionine residue at the N-terminus of the product protein. The removal of the cysteine reside did not affect the solubility or the overall expression efficiency of the precursor protein, and further resulted in a much higher recovery of uncleaved precursor (FIG. 23A, left side without cysteine). It was also noted in both fusions that the intein exhibited full

TABLE 2

Proteins inserted into the intein fusion system.

| Product | Description | Mol. Wt (kDa) | Name | Cys ? | Half Life(min)[a] | Active? | Comments |
|---|---|---|---|---|---|---|---|
| Protein | | | | | | | |
| Thymidylate Synthase (TS) | Methylase for DNA synthesis | 31.5 | pMI(c)T | Yes | 35 | Yes | Used for initial screening of intein function |
| TS | | 31.5 | pMIT | No | 420 | Yes | Used for initial screening of intein function |
| C-domain of I-TevI | DNA binding domain | 14 | pMI(c)C | Yes | 7.3 | Yes | Assayed through DNA binding gel-shifts. |
| Hfq Protein | RNA chaperon protein | 18 | pMI(c)Hfq | Yes | 30 | n.t.[b] | Forms multimeric assemblies on column(?) |
| Hfq Protein | | 18 | pMIHfq | No | 150 | n.t. | Forms multimeric assemblies on column(?) |
| rh aFGF | Human fibroblast growth factor | 14 | pMI(c)aFGF | Yes | 7 | n.t. | Cleaves too rapidly for efficient purification |
| rh aFGF | | 14 | pMIaFGF | No | 55 | Yes | |
| I-TevIII | Homing Endonuclease | 32 | pMIITevIII | No | 60 | Yes* | Loss of activity may be buffer related |
| Alpha | α subunit RNA polymerase | 37 | pMI(c)α | Yes | 15 | Yes** | Recruits β, β and σ subunits when expressed |
| Sigma | σ⁷⁰ subunit RNA polymerase | 69 | pMI(c)σ | Yes | 15 | Yes** | Recruits β and β subunits when expressed |
| CAP protein | Catabolite Activator | 24 | pMI(c)CAP | Yes | 15 | Yes** | |
| I-TevI | Homing Endonuclease I-TevI | 29 | pMI(c)ItevI | Yes | n.t. | Yes*** | Too toxic to clone into E. coli. |

[a]Half life measured at pH 6.0 and 37° C.
[b]n.t. = not tested.
*Low level of activity consistent with highly labile protein.
**Activity not tested although fusion proteins associate specifically with other RNA polymerase subunits and the protein is therefore properly folded.
***Toxicity can be reduced to practical levels through intein insertional inactivation (see FIGS. 2, 4, 5 19 and 20).

activity under optimal conditions, and cleaved to completion in tests on purified precursors. Similar results have been achieved with intein fusions in purifying six other proteins: the homing endonuclease I-TevIII; the RNA chaperone Hfq; the alpha, sigma and CAP subunits of *E. coli* RNA polyymerase; and the C-terminal DNA binding domain of the homing endonuclease I-TevI.

Process optimization requires that any pre-purification cleavage of tripartite fusion precursor be minimized, not only to maximize product recovery, but also to reduce competition for affinity resin binding sites between uncleaved precursor protein and prematurely cleaved binding domains. To optimize aFGF recovery, the precursor was induced at a number of temperatures to investigate MI:aFGF overexpression and premature cleavage in vivo. The ratio of precursor to cleavage products at the end of the induction varied strongly with temperature. Although overall expression was most efficient at 30° C. to 37° C., the cleavage reaction was also accelerated, leading to substantial precursor cleavage during induction (FIG. 23B). Furthermore, extended induction times, particularly high temperatures, also led to high levels of precursor cleavage.

To maximize production of the MI:aFGF precursor for purification studies, conditions were selected to provide a compromise between overall yield and minimal premature cleavage. Cultures were grown in shake flasks to late log phase ($OD_{650}$ of 0.8 or approximately $8 \times 10^8$ cells/ml). An induction temperature of 20° C. was used to decrease the cleavage rate (0.1 $h^{-1}$ at 37° C. vs. 0.02 $h^{-1}$ at 20° C.) while still allowing reasonable expression efficiency (approximately 5% of the total cell protein at end of induction). Finally, the induction time was limited to four hours, limiting premature precursor cleavage to <5% of the expressed protein (FIG. 23B).

Effect of Temperature on Cleavage Rate In vivo

To further aid in process optimization, the dependence of rate constant on temperature was determined at the optimal cleavage pH. Uncleaved precursor protein was purified using a standard maltose affinity protocol, adjusted to pH 6.0 by addition of HCl, and incubated at different temperatures. Samples separated by SDS-PAGE were analyzed by scanning densitometry of Coomassie stained gels (FIG. 24A), yielding rate constants over a range of temperatures. A strong dependence of rate on temperature was observed, with the cleavage rate of MI:aFGF typically accelerating by a factor of greater than 40 between 4° C. and 37° C. (FIG. 24B). A plot of ln(k) vs. reciprocal temperature for this precursor further indicated that the cleavage reaction fits an Arrhenius equation with a cleavage activation energy of 20.6 kcal/mol (FIG. 23C). This value is substantially higher than the 3 to 5 kcal/mol typically reported for enzyme catalyzed reactions (Bailey and Ollis (1986) Biochemical Engineering Fundamentals. McGraw-Hill Book Co.), and accounts for the relatively strong temperature dependence displayed by the intein.

Notably, the reaction rate was greatly reduced at 42° C. over the long term, although initially it was much faster than the reaction at 37° C. (FIG. 23). The loss of activity in this fusion at 42° C. indicates that the intein is initially active and follows the Arrhenius form, but is rapidly inactivated by structural instability of either the intein, the product protein or both. Reported activation energies for protein denaturation are typically 40 to 70 kcal/mol, only 2- to 3-fold higher than the cleavage activation energy for this precursor. Bailey et al. (1986). The high cleavage activation energy and the observed rapid inactivation of the intein at 42° C. suggest that the intein structure must be significantly perturbed in order for the cleavage reaction to take place. This hypothesis is consistent with the conformational changes that are required by the intein in undergoing splicing or cleavage. Xu et al. (1996).

Effect of pH on Cleavage Rate In vitro

Figure 25:
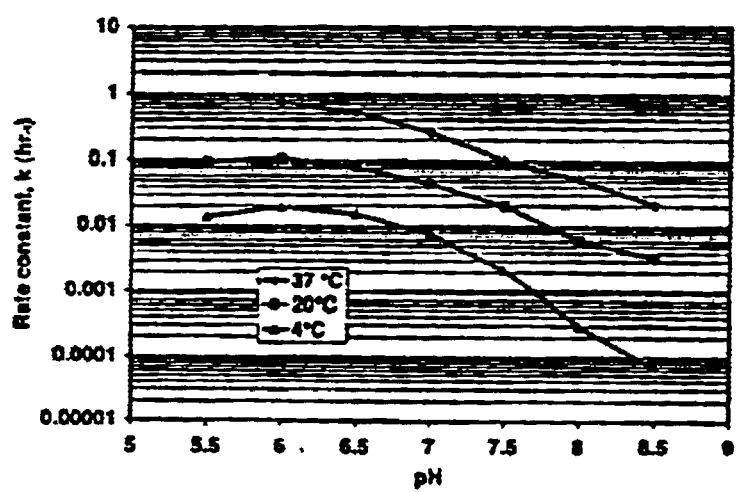
FIG. 25 shows cleavage rate constant for cysteineless MI:aFGF vs. temperature and pH for purification strategy conditions.

To provide accurate process modeling and optimization, the intein cleavage rate as a function of pH is required. Samples collected during precursor cleavage reactions under various conditions of pH and temperature were analyzed by SDS-PAGE. Rate constants for native MI:aFGF were determined at 4° C., 20° C. and 37° C. with pH values ranging from 5.5 to 8.5 (FIG. 25). As the pH was shifted from 8.5 to 6.0, the cleavage rate at 4° C. increased by well over two orders of magnitude, decreasing the cleavage half-life from thousands of hours to 35 hours. The cleavage acceleration was less pronounced at higher temperatures, increasing by a factor of only 40 to 37° C. However, the optimal pH half life decreased to less than one hour at 37° C., making this temperature worthy of consideration for the cleavage step of the purification process. The addition of a cysteine residue to the beginning of the product protein was again observed to increase the overall cleavage rate by a factor of 10 or more, with persistence of the pH sensitivity of the intein. Other precursor proteins tested exhibited similar rates of cleavage to MI:aFGF, with a 20 to 40-fold increase in activity between the pH range of 8.5 to 6.0 typically observed. Ultimately, cleavage of cysteineless precursor protein was sufficiently slow at 4° C. and pH 8.5 that precursor could be stored for several days without significant loss of precursor or intein activity. In contrast, precursors that included a cysteine residue cleaved more quickly, such that they could not be stored for more than 24 hours without significant cleavage.

Remarkably, ln(k) was linearly related to pH at all temperatures for pH>7, thus exhibiting characteristics of a simple proton-catalyzed reaction (FIG. 25). Based on structural and pH-kinetic data, it has been speculated that the pH sensitivity of the intein arises from protonation of the highly conserved penultimate histidine residue of the intein C-terminus (FIG. 1A) (Wood et al., 1999). The close correspondence of the half-maximum rate constant pH in MI:aFGF (6.7 to 6.9) and the histidine sidechain pKa (approximately 6.5) provide further support for this hypothesis. It is also possible that the existence of a proton "binding pocket" may exist in the precursor, slightly increasing the precursor attraction for free protons and thus accounting for the slight increase in half-maximum rate pH over the pKa of histidine.

The relative independence of the hypothesized roles of structural perturbation and histidine protonation suggest that the cleavage rate constant can be represented with the split form:

$$k=k'(T)[H^+](pH>7.0) \qquad (5)$$

where k'(T) is a structural perturbation-dependent rate constant, which follows an Arrhenius form, and [$H^+$] is the solution proton concentration. Although this equation is only valid for the pH range where the histidine sidechain is unsaturated (pH>7.0), it does provide an explanation for the profound effects of pH and temperature on cleavage rate. An increase in temperature sensitivity at low pH also suggests that k'(T) has a slight dependence on pH (FIG. 25), although this effect is difficult to quantify due to the extremely low rates of cleavage at high pH and low temperature.

Model Verification

Verification of the flow-mode model was carried out by determining the product concentration of each fraction exiting the column and comparing it to the model predictions (FIG. 26). Two purification experiments in flow mode were carried out, one at 37° C. as above, and the other at 25° C. to slightly decrease the cleavage rate on the column. An online pH detector used to determine the shape of the pH front exiting the column during purification indicated that the shape of the pH front was independent of flow within the limitations required for reasonable product concentration (1 ml/min to 0.01 ml/min). The 37° C. cleavage purification showed a tight correlation to the model prediction, with the peak exhibiting the exponential decay shape predicted by the analytical solution as well as the numerical simulation FIG. 26A). The 25° C. cleavage also showed typical characteristics, although the peak was much broader, also in agreement with simulation and analytical expectation (FIG. 26B). In both of these experiments, the best fitted rate constant was significantly higher (about 20%) than that measured using free precursor in a test tube, it is likely that the binding of the precursor to the column somewhat accelerated the cleavage reaction due to steric effects, effectively lowering the reaction energy. The high degree of predictive accuracy displayed by the model will allow rapid process simulation and optimization of large scale with minimal pilot scale experimentation.

Having thus described in detail preferred embodiments of the invention, it is to be understood that the invention defined by the appended claims is not to be limited to particular details set forth in the above description as many apparent variations thereof are possible without departing from the spirit or scope of the invention.

Reference listing

| Author | Year | Title | Journal | Volume:pp |
|---|---|---|---|---|
| | 1985 | Nucleic Acid Hybridization, A Practical Approach | Hames and Higgins eds IRL Press, Oxford | |
| Altschul et al. | | | Nucl. Acids Res. | 25:3389–3402 |
| Amitai et al. | 1999 | Fine-tuning an engineered intein | Nature Biotech. | 17:854–855 |
| Bailey et al. | 1986 | Biochemical engineering fundamentals | McGraw-Hill Book Company | |
| Beachy et al. | 1997 | Multiple roles of cholesterol in hedgehog proteins biogenesis and signaling | Cold Spring Harbor Symposium of Quantitative Biology | 62:191–204 |
| Belfort et al. | 1984 | A genetic system for analyzing *E. coli* thymidylate synthase | J. Bacteriol. | 160:371–378 |
| Chen et al. | 2000 | Dissecting the chemistry of protein splicing and its applications | Angew. Chem. Int. Ed. | 39:450–466 |
| Chen et al. | 2000 | Protein splicing in the absence of an intein penultimate histidine | J. Biol. Chem. | 275:20431–20435 |
| Chong et al. | 1996 | Protein splicing involving the *Saccharomyces cerevisiae* VMA intein: the steps in the splicing pathway, side reactions leading to protein cleavage and establishment of an in vitro splicing system | J. Biol. Chem. | 271:22159–22168 |
| Chong et al. | 1997 | Protein splicing of the *Saccharomyces cerevisiae* VMA intein without the endonuclease motifs | J. Biol. Chem. | 272:15587–15590 |
| Chong et al. | 1997 | Single-column purification of free recombinant proteins using a self-cleavage affinity tag derived from a protein splicing element | Gene | 192:271–281 |
| Chong et al. | 1998 | Modulation of protein splicing of the *Saccharomyces cerevisiae* vacuolar membrane ATPase intein | J. Biol. Chem. | 273:10567–10577 |
| Chong et al. | 1998 | Utilizing the C-terminal cleavage activity of a protein splicing element to purify recombinant proteins in a single chromatographic step. | Nucl. Acids Res. | 26:5109–5115 |
| Clarke | 1994 | A proposed mechanism for the self-splicing of proteins | Proc. Natl. Acad. Sci. USA | 91:11084–8 |
| Colston et al. | 1994 | The ins and outs of protein splicing elements | Mol. Microbiol. | 12:359–363 |
| Cooper et al. | 1993 | Protein splicing: excision of intervening sequences at the protein level | Bioessays | 15:667–674 |
| Cooper et al. | 1995 | Protein splicing: self-splicing of genetically mobile elements at the protein level | TIBS | 20:351–356 |
| Cussler | 1984 | Diffusion: Mass transfer in fluid systems | Cambridge University Press | |

-continued

Reference listing

| Author | Year | Title | Journal | Volume:pp |
|---|---|---|---|---|
| Dalgaard et al. | 1997 | Statistical modeling and analysis of the LAGLIDADG family of site-specific endonucleases and identification of an intein that encodes a site-specific endonuclease of the H—N—H family | Nucl. Acids Res. | 25:4626–4638 |
| Dalgaard et al. | 1997 | Statistical modeling, phylogenetic analysis and structure prediction of a protein splicing domain common to inteins and hedgehog proteins | J. Comput. Biol. | 4:193–214 |
| Daugelat et al. | 1999 | The *Mycobacterium tuberculosis* recA intein can be used in an ORFTRAP to select for open reading frames | Prot. Sci. | 8:644–653 |
| Davis et al. | 1991 | Novel structure of the recA locus of *Mycobacterium tuberculosis* implies processing of the gene product | J. Bact. | 173:5653–5662 |
| Davis et al. | 1992 | Protein splicing in the maturation of the *M. tuberculosis* recA protein: A mechanism for tolerating a novel class of intervening sequence | Cell | 71:201–210 |
| Deen | 1998 | Analysis of transport phenomena | Oxford University Press | |
| Derbyshire et al. | 1997a | Two-domain structure of the td intron-encoded endonuclease I-TevI correlates with the two-domain configuration of the homing site | J. Mol. Biol | 265:494–506 |
| Derbyshire et al. | 1997b | Genetic definition of a protein-splicing domain: functional mini-inteins support structure predictions and a model for intein evolution | Proc. Natl. Acad. Sci. USA | 94:11466–11471 |
| Devereux et al. | 1984 | A comprehensive set of sequence analysis program for the VAX | Nucl. Acids Res. | 12:387–395 |
| Duan et al. | 1997 | Crystal structure of PI-SceI, a homing endonuclease with protein splicing activity | Cell | 89:555–564 |
| Evans et al. | 1998 | Semisynthesis of cytotoxic proteins using a modified protein splicing element | Prot. Sci. | 7:2256–2264 |
| Evans et al. | 1999 | The cyclization and polymerization of bacterially expressed proteins using modified self-splicing inteins | J. Biol. Chem. | 274:18359–18363 |
| Evans et al. | 1999 | The in vitro ligation of bacterially expressed proteins using an intein from *Methanobacterium thermoautotrophicum* | J. Biol. Chem. | 274:3923–3926 |
| Evans et al. | 2000 | Protein trans-splicing and cyclization by a naturally split intein of the dnaE gene of *Synechocystis* species PCC6803 | J. Biol. Chem. | 275:9091–9094 |
| Feng et al. | 1987 | Progressive sequence alignment as a prerequisite to correct phylogenetic trees | J. Molec. Evol. | 25:351–360 |
| Fish et al. | 1984 | The interaction between fermentation and protein recovery | BioTech. | 2:263 |
| Ghim et al. | 1998 | An 8 kb nucleotide sequence at the 3' flanking region of the sspC gene (184 degrees) on the *Bacillus subtilis* 168 chromosome containing an intein and an intron | DNA Res. | 30:121–6 |
| Gimble | 1998 | Putting protein splicing to work | Chemistry & Biology | 5:R251–R256 |
| Gorbalenya | 1998 | Non-canonical inteins | Nucl. Acids Res. | 26:1741–8 |

-continued

Reference listing

| Author | Year | Title | Journal | Volume:pp |
|---|---|---|---|---|
| Hahn et al. | 1996 | Mutational analysis of the encephalomyocarditis virus primary cleavage | J. Virol. | 6870–6875 |
| Higgins et al. | 1989 | Fast and sensitive multiple sequence alignment on a microcomputer | CABIOS | 5:151–153 |
| Hirata et al. | 1990 | Molecular structure of a gene, VMA1, encoding the catalytic subunit of $H^+$-translocating adenosine triphosphatase from vacuolar membranes of *Saccharomyces cerevisiae* | J. Biol. Chem. | 265:6726–6733 |
| Horton et al. | 1990 | Gene splicing by overlap extension: Tailor-made genes using the polymerase chain reaction | BioTech. | 8:528–536 |
| Jackson et al. | 1986 | A detailed kinetic analysis of the in vitro synthesis and processing of encephalomyocarditis virus products | Virol. | 149:114–127 |
| Kane et al. | 1990 | Protein splicing converts the yeast TFP1 gene product to the 69-kD subunit of the vacuolar $H^+$-adenosine triphosphatase | Science | 250:651–657 |
| Kapust et al. | 1999 | *Escherichia coli* maltose-binding protein uncommonly effective at promoting the solubility of polypeptides to which it is fused | Prot. Sci. | 8:1668–1674 |
| Klabunde et al. | 1998 | Crystal structure of gyrA intein from *Mycobacterium xenopi* reveals structural basis of protein splicing | Nature Struct. Biol. | 5:31–36 |
| LaVallie et al. | 1995 | Gene fusion expression systems in *Escherichia coli* | Curr. Opin. Biotechnol. | 6:501–506 |
| Lew et al. | 1998 | Protein splicing in vitro with a semi-synthetic two-component minimal intein | J Biol. Chem. | 273:15887–90 |
| Linder et al. | 1998 | Improved immobilization of fusion proteins via cellulose-binding domains | Biotech. & Bioeng. | 60:642–647 |
| Liu and Hu | 1997 | DnaB intein in *Rhodothermus marinus*: indication of recent intein homing across remotely related organisms | Proc. Natl. Acad. Sci. USA. | 94:7851–6 |
| Mathys et al. | 1999 | Characterization of a self-splicing mini-intein and its conversion into autocatalytic N- and C-terminal cleavage elements: facile production of protein binding blocks for protein ligation | Gene | 231:1–13 |
| Mills et al. | 1998 | Protein splicing in trans by purified N- and C-terminal fragments of the *Mycobacterium tuberculosis* RecA intein | Proc. Natl. Acad. Sci. USA. | 95:3543–8 |
| Myers et al. | 1988 | Optimal Alignments in Linear Space | CABIOS | 4:11–17 |
| Needleman et al. | 1970 | A general method applicable to the search for similarities in the amino acid sequences of two proteins | J. Mol. Biol. | 48:444–453 |
| Noren et al. | 2000 | Dissecting the chemistry of protein splicing and its applications | Angewandte Chemie Int. Ed. | 39:450–466 |
| Perler et al. | 1994 | Protein splicing elements: inteins and exteins - a definition of terms and recommended nomenclature | Nucl. Acids Res. | 22:1125–1127 |
| Pietrokovski et al. | 1994 | Conserved sequence features of inteins (protein introns) and their use in identifying new inteins and related proteins | Protein Sci. | 3:2340–2350 |
| Poland et al. | 2000 | Structural insights into the protein splicing mechanism of PI-SceI | J. Biol. Chem. | 275:16408–16413 |

-continued

Reference listing

| Author | Year | Title | Journal | Volume:pp |
|---|---|---|---|---|
| Pradhan et al. | 1999 | Recombinant human DNA (Cystosine-5) methyltransferase I. Expression, purification, and comparison of de novo and maintenance methylation | J. Biol. Chem. | 274:33002–33010 |
| Ryan et al. | 1991 | Cleavage of foot-and-mouth disease virus polyprotein is mediated by residues located within 19 amino acid sequence | J. Gen. Virol. | 72:2727–2732 |
| Ryan et al. | 1994 | Foot-and-mouth disease virus 2A oligopeptide mediated cleavage of an artificial polyprotein | EMBO J. | 13:928–933 |
| Sambrook | 1989 | Molecular Cloning, A Laboratory Manual | Second ed., CSH Press, Cold Spring Harbor | |
| Shao et al. | 1995 | Protein splicing: characterization of the aminosuccinimide residue at the carboxyl terminus of the excised intervening sequence | Biochem. | 34:10844–50 |
| Shao et al. | 1996 | Engineering new functions and altering existing functions | Curr. Opin. Struct. Biol. | 6:513–518 |
| Shingledecker et al. | 1998 | Molecular dissection of the *Mycobacterium tuberculosis* RecA intein: design of a minimal intein and of a trans-splicing system involving two intein fragments | Gene | 207:187–195 |
| Shingledecker et al. | 2000 | Reactivity of the cysteine residues in the protein splicing active center of the *Mycobacterium tuberculosis* RecA intein | Ach. Biochem. Biophys. | 375:138–144 |
| Smith et al. | 1981 | Comparison of Bio-sequences | Adv. App. Math. | 2:482–489 |
| Smith et al. | 1983 | Statistical characterization of nucleic acid sequence functional domains | Nucl. Acids Res. | 11:2205–2220 |
| Southworth et al. | 1999 | Purification of proteins fused to either the amino or carboxy terminus of the *Mycobacterium xenopi* gyrase A intein | BioTech. | 27:110–120 |
| Southworth et al. | 1998 | Control of protein splicing by intein fragment reassembly | EMBO J. | 17:918–26 |
| Stoddard et al. | 1998 | Breaking up is hard to do | Nat. Struct. Biol. | 5:3–5 |
| Studier et al. | 1990 | Use of T7 RNA polymerase to direct expression of cloned genes. | Met. Enzymol. | 185:60–89 |
| Telenti et al. | 1997 | The *Mycobacterium xenopi* GyrA protein splicing element: characterization of a minimal intein | J. Bacteriol. | 179:6378–82 |
| Thompson et al. | 1994 | Cluster W: improving the sensitivity of progressive multiple sequenee alignment through sequence weighing, positions-specific gap penalties and weight matrix choice | Nuc. Acid Res. | 22:4673–480 |
| Uhlens et al. | 1990 | | | |
| U.S. Pat. No. 5,496,714 | | | | |
| U.S. Pat. No. 5,795,731 | | | | |
| U.S. Pat. No. 5,834,247 | | | | |
| Volkin et al. | 1996 | The characterization, stabilization, and formulation of acidic fibroblast growth factor | Pharma Biotech. | 9:181–217 |
| Wang and Liu | 1997 | Identification of an unusual intein in chloroplast ClpP protease of *Chlamydomonas eugametos* | J. Biol. Chem. | 272:11869–73 |
| Wilbur et al. | 1983 | | Proc. Natl. Acad. Sci. USA | 80:726 |
| Wood et al. | 1997 | Controllable Protein Splicing For Use In Biochemistry | AIChE (American Institute of | |

-continued

Reference listing

| Author | Year | Title | Journal | Volume:pp |
|---|---|---|---|---|
| Wood et al. | 1998 | Fusion Based Affinity Separations Using Self-Cleaving Affinity Groups | Chemical Engineers) National Meeting, ACS (American Chemistry Society) National Meeting | |
| Wood et al. | 1998 | Genetic Screens Based On Folate Consumption In Engineered Pathways | ACS (American Chemistry Society) National Meeting | |
| Wood et al. | 1998 | Characterization and Manipulation of the Folate Cycle For The Creation Of In Vivo Genetic Screens | AIChE (American Institute of Chemical Engineers) National Meeting | |
| Wood et al. | 1998 | Generation And Application Of Self-Cleaving Peptide Linkers For Use In Affinity Separations | AIChE (American Institute of Chemical Engineers) National Meeting | |
| Wood et al. | 1999 | A genetic system yields self-cleaving inteins for bioseparations | Nature Biotech. | 17:889–892 |
| Wood et al. | 1999 | Protein engineering of inteins: genetic system yields self-cleaving element for bioseparations | Nature Biotech. | |
| Wu et al. | 1998 | | Biochim. Biophys. Acta | 1387:422–32 |
| Xu et al. | 1996 | The mechanism of protein splicing and its modulation by mutation | EMBO J. | 15:5146–5153 |

What is claimed is:

1. A non-naturally occurring intein or cleavage or cleavage and splicing moiety having splicing activity and/or controllable cleavage activity, wherein the intein is a truncated Mtu recA intein with the endonuclease domain deleted, and V67L and/or D422G mutation(s), wherein the truncated Mtu recA intein is ΔI-CM or ΔI-SM, or any full-length Mtu recA intein having a V67L and/or a D422G mutation(s).

2. The intein of claim 1 comprising a truncated intein.

3. The intein of claim 1 wherein the cleavage activity is controllable by varying at least one physical condition or by varying at least one chemical condition or by varying both at least one physical condition and at least one chemical condition.

4. The intein of claim 3 wherein the cleavage activity is controllable by varying pH.

5. The intein of claim 3 wherein the cleavage activity is controllable by varying temperature.

6. The intein of claim 3 wherein the cleavage activity is controllable by varying ion concentration, presence or absence.

7. The intein of claim 3 wherein the cleavage activity is controllable by at least two of: varying pH, varying temperature, and varying ion concentration, presence or absence.

8. The intein of claim 3 wherein the cleavage activity is controllable by varying temperature and pH.

9. The intein of claim 1 wherein the intein is obtained from random mutagenesis of a truncated intein, followed by selection based on growth phenotype.

10. The intein of claim 1 wherein the intein has C-terminal cleavage.

11. The intein of claim 1 wherein the intein is a truncated Mtu intein.

12. The intein of claim 1 wherein cleavage rate is determined by an enzymatic reaction and not a chemical reaction.

13. The intein of claim 1 wherein the intein has the endonuclease domain deleted.

14. The intein of claim 1 containing the C-terminal histidine.

15. A protein including an intein of claim 1.

16. The protein of claim 15 comprising a polypeptide of interest and the intein.

17. The protein of claim 16 wherein the intein is in an inter-domain region of the polypeptide of interest.

18. The protein of claim 15 wherein the protein comprises a binding protein portion, the intein, and a reporter protein portion.

19. The protein of claim 18 wherein the intein separates the binding protein portion and the reporter protein portion.

20. The protein of claim 18 wherein the reporter protein is an enzymatic assay protein, a protein conferring antibiotic resistance, or a protein providing a direct colorimetric assay.

21. The protein of claim 18 wherein the reporter protein is selected from the group consisting of: thymidylate synthase, β-galactosidase, galactokinase, alkaline phosphatase, β-lactamase, luciferase, and green fluorescent protein.

22. The protein of claim 15 wherein the protein comprises a binding protein portion, the intein, and a protein of interest portion.

23. The protein of claim 18 wherein the intein separates the binding protein portion and the protein of interest portion.

24. The protein of claim 15 comprising an external fusion of a polypeptide and the intein.

25. The protein of claim 15 comprising an internal fusion of a polypeptide and the intein.

26. The protein of claim 15 comprising a desired polypeptide and the intein, as either an internal fusion or an external fusion, wherein the intein is located before a serine, threonine or cysteine residue of the desired polypeptide.

27. The protein of claim 15 comprising a desired polypeptide and the intein, wherein the intein and the desired polypeptide are separated by a serine, threonine or cysteine residue.

28. The protein of claim 15 comprising a desired polypeptide and the intein, wherein the C-terminal histidine or asparagine or histidine-asparagine of the intein is immediately followed by the initial methionine of the desired polypeptide.

29. The protein of claim 15 comprising a desired polypeptide and the intein, wherein the initial methionine of the desired polypeptide has been eliminated.

30. The protein of claim 14 comprising a desired polypeptide and the intein, wherein the C-terminal histidine or asparagine or histidine-asparagine of the intein is immediately followed by the second amino acid of the desired polypeptide.

31. The protein of claim 20 wherein the second amino acid of the desired polypeptide is lysine.

* * * * *

UNITED STATES PATENT AND TRADEMARK OFFICE
CERTIFICATE OF CORRECTION

PATENT NO.         : 6,933,362 B1
APPLICATION NO. : 09/641808
DATED                 : August 23, 2005
INVENTOR(S)       : Marlene Belfort et al.

It is certified that error appears in the above-identified patent and that said Letters Patent is hereby corrected as shown below:

On Title Page (73)

--Health Research Incorporated, Rensselaer, New York (US)-- should be added as an Assignee Column 56, line 19, please replace "claim 20" with --claim 30--.

Signed and Sealed this

Twelfth Day of September, 2006

JON W. DUDAS
*Director of the United States Patent and Trademark Office*

UNITED STATES PATENT AND TRADEMARK OFFICE
CERTIFICATE OF CORRECTION

PATENT NO. : 6,933,362 B1  
APPLICATION NO. : 09/641808  
DATED : August 23, 2005  
INVENTOR(S) : Marlene Belfort et al.

Page 1 of 1

It is certified that error appears in the above-identified patent and that said Letters Patent is hereby corrected as shown below:

Column 1, line 14, replace the paragraph with the following:

"SUPPORT

Without any admission, prejudice, intention of creating any estoppels, and the like, especially without any admission as to ownership or rights and without any prejudice to or estoppels against any ownership or rights position, it is stated that this work was supported by NIH grants GM39422 and GM44844, a Howard P. Isermrann fellowship through the Department of Chemical Engineering, Rensselaer Polytechnic Institute and a gift from Baxter Healthcare."

--STATEMENT REGARDING FEDERALLY SPONSORED RESEARCH OR DEVELOPMENT

This invention was made with government support under GM39422 and GM44844 awarded by the National Institutes of Health. The government has certain rights in the invention. Additional support was provided by a Howard P. Isermann fellowship through the Department of Chemical Engineering, Rensselaer Polytechnic Institute and a gift from Baxter Healthcare.--

Signed and Sealed this  
First Day of May, 2012

David J. Kappos  
*Director of the United States Patent and Trademark Office*

SEQUENCE LISTING

```
<160> NUMBER OF SEQ ID NOS: 26

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 1

Cys Gly Glu Gln Pro Thr Gly
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 2

Ser Ile Glu Gln Asp
 1               5

<210> SEQ ID NO 3
<211> LENGTH: 5
<212> TYPE: PRT
<213> ORGANISM: Artificial Sequence
<220> FEATURE:
```

-continued

<223> OTHER INFORMATION: Description of Artificial Sequence:
      Illustrative peptide

<400> SEQUENCE: 3

Cys Arg Ala Met Gly
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 4

Met Ile Glu Gln Asp
 1               5

<210> SEQ ID NO 5
<211> LENGTH: 19
<212> TYPE: PRT
<213> ORGANISM: Foot-and-mouth disease virus

<400> SEQUENCE: 5

Leu Leu Asn Phe Asp Leu Leu Lys Leu Ala Gly Asp Val Glu Ser Asn
 1               5                  10                  15

Pro Gly Pro

<210> SEQ ID NO 6
<211> LENGTH: 8
<212> TYPE: DNA
<213> ORGANISM: Artificial Sequence
<220> FEATURE:
<223> OTHER INFORMATION: Description of Artificial Sequence:
      Illustrative polynucleotide sequernce

<400> SEQUENCE: 6 agtcagtc                                                               8

<210> SEQ ID NO 7
<211> LENGTH: 8
<212> TYPE: DNA
<213> ORGANISM: Artificial Sequence
<220> FEATURE:
<223> OTHER INFORMATION: Description of Artificial Sequence:
      Illustrative polynucleotide sequernce

<400> SEQUENCE: 7 aatcaatc                                                               8

<210> SEQ ID NO 8
<211> LENGTH: 19
<212> TYPE: PRT
<213> ORGANISM: Foot-and-mouth disease virus

<400> SEQUENCE: 8

Leu Leu Asn Phe Asp Leu Leu Lys Leu Ala Gly Asp Val Glu Ser Asn
 1               5                  10                  15

Pro Gly Pro

<210> SEQ ID NO 9
<211> LENGTH: 9
<212> TYPE: PRT
<213> ORGANISM: Saccharomyces cerevisiae

```
<400> SEQUENCE: 9

Phe Thr Cys Asn Ala Thr His Glu Leu
 1               5

<210> SEQ ID NO 10
<211> LENGTH: 9
<212> TYPE: PRT
<213> ORGANISM: Mycobacterium leprae

<400> SEQUENCE: 10

Phe Ala Ala Thr Pro Asn His Leu Ile
 1               5

<210> SEQ ID NO 11
<211> LENGTH: 9
<212> TYPE: PRT
<213> ORGANISM: Mycobacterium xenopi

<400> SEQUENCE: 11

Val Thr Gly Thr Ala Asn His Pro Leu
 1               5

<210> SEQ ID NO 12
<211> LENGTH: 9
<212> TYPE: PRT
<213> ORGANISM: Pyrococcus sp.

<400> SEQUENCE: 12

Ile Thr Ile Thr Glu Gly His Ser Leu
 1               5

<210> SEQ ID NO 13
<211> LENGTH: 9
<212> TYPE: PRT
<213> ORGANISM: Porphyra purpurea

<400> SEQUENCE: 13

Leu Glu Leu Thr Ser Asn His Lys Ile
 1               5

<210> SEQ ID NO 14
<211> LENGTH: 9
<212> TYPE: PRT
<213> ORGANISM: Mycobacterium tuberculosis

<400> SEQUENCE: 14

Val Trp Ala Thr Pro Asp His Lys Val
 1               5

<210> SEQ ID NO 15
<211> LENGTH: 9
<212> TYPE: PRT
<213> ORGANISM: Caenorhabditis elegans

<400> SEQUENCE: 15

Leu Arg Ile Thr Ser Arg His Phe Met
 1               5

<210> SEQ ID NO 16
<211> LENGTH: 9
<212> TYPE: PRT
<213> ORGANISM: Drosophila melanogaster

<400> SEQUENCE: 16
```

```
Leu Thr Val Thr Pro Ala His Leu Val
 1               5
```

<210> SEQ ID NO 17
<211> LENGTH: 9
<212> TYPE: PRT
<213> ORGANISM: Xenopus laevis

<400> SEQUENCE: 17

```
Ile Arg Leu Thr Ala Ala His Leu Leu
 1               5
```

<210> SEQ ID NO 18
<211> LENGTH: 19
<212> TYPE: PRT
<213> ORGANISM: Saccharomyces cerevisiae

<400> SEQUENCE: 18

```
Asp Tyr Tyr Gly Ile Thr Leu Ser Asp Asp Ser Asp His Gln Phe Leu
 1               5                  10                  15

Leu Ala Asn
```

<210> SEQ ID NO 19
<211> LENGTH: 18
<212> TYPE: PRT
<213> ORGANISM: Mycobacterium leprae

<400> SEQUENCE: 19

```
Ser Met Asn Arg Phe Asp Ile Glu Val Glu Gly Asn His Asn Tyr Phe
 1               5                  10                  15

Val Asp
```

<210> SEQ ID NO 20
<211> LENGTH: 19
<212> TYPE: PRT
<213> ORGANISM: Mycobacterium xenopi

<400> SEQUENCE: 20

```
Val Gln Pro Val Tyr Ser Leu Arg Val Asp Thr Ala Asp His Ala Phe
 1               5                  10                  15

Ile Thr Asn
```

<210> SEQ ID NO 21
<211> LENGTH: 18
<212> TYPE: PRT
<213> ORGANISM: Pyrococcus sp.

<400> SEQUENCE: 21

```
Asp Gly Tyr Val Tyr Asp Leu Ser Val Asp Glu Asp Glu Asn Phe Leu
 1               5                  10                  15

Ala Gly
```

<210> SEQ ID NO 22
<211> LENGTH: 18
<212> TYPE: PRT
<213> ORGANISM: Porphyra purpurea

<400> SEQUENCE: 22

```
Phe Gln Asn Val Phe Asp Phe Ala Ala Asn Pro Ile Pro Asn Phe Ile
 1               5                  10                  15

Ala Asn
```

<210> SEQ ID NO 23
<211> LENGTH: 18
<212> TYPE: PRT
<213> ORGANISM: Mycobacterium tuberculosis

<400> SEQUENCE: 23

Arg Ala Arg Thr Phe Asp Leu Glu Val Glu Glu Leu His Thr Leu Val
 1               5                  10                  15

Ala Glu

<210> SEQ ID NO 24
<211> LENGTH: 16
<212> TYPE: PRT
<213> ORGANISM: Caenorhabditis elegans

<400> SEQUENCE: 24

Thr Gly Ile Tyr Ser Pro Leu Thr Asn Asn Gly Arg Ile Ile Val Asn
 1               5                  10                  15

<210> SEQ ID NO 25
<211> LENGTH: 16
<212> TYPE: PRT
<213> ORGANISM: Drosophila melanogaster

<400> SEQUENCE: 25

Lys Gly Val Val Ala Pro Leu Thr Arg Glu Gly Thr Ile Val Val Asn
 1               5                  10                  15

<210> SEQ ID NO 26
<211> LENGTH: 16
<212> TYPE: PRT
<213> ORGANISM: Xenopus laevis

<400> SEQUENCE: 26

Thr Gly Ala Tyr Ala Pro Leu Thr Ala His Gly Thr Val Val Ile Asp
 1               5                  10                  15